United States Patent
Kubo et al.

(10) Patent No.: US 7,700,771 B2
(45) Date of Patent: Apr. 20, 2010

(54) HETEROCYCLIC COMPOUND WHICH MAY BE USED AS A MEDICINE HAVING P38 MAP KINASE INHIBITORY ACTIVITY

(75) Inventors: Akira Kubo, Osaka (JP); Tetsu Nakane, Osaka (JP); Tatsuo Nakajima, Osaka (JP); Takanori Murakami, Osaka (JP); Hidetaka Miyoshi, Osaka (JP); Akihito Ogasawara, Osaka (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 103 days.

(21) Appl. No.: 11/587,498

(22) PCT Filed: Apr. 28, 2005

(86) PCT No.: PCT/JP2005/008564

§ 371 (c)(1),
(2), (4) Date: Oct. 26, 2006

(87) PCT Pub. No.: WO2005/105790

PCT Pub. Date: Nov. 10, 2005

(65) Prior Publication Data

US 2007/0185326 A1   Aug. 9, 2007

Related U.S. Application Data

(60) Provisional application No. 60/566,089, filed on Apr. 29, 2004.

(30) Foreign Application Priority Data

Apr. 28, 2004   (JP)   ............... 2004-133204
Jan. 14, 2005   (JP)   ............... 2005-007832

(51) Int. Cl.
   *C07D 239/02*   (2006.01)
(52) U.S. Cl. .................. 544/297; 544/315; 544/330
(58) Field of Classification Search ............ None
See application file for complete search history.

(56) References Cited

U.S. PATENT DOCUMENTS

2002/0032183 A1   3/2002   LoGrasso et al.

FOREIGN PATENT DOCUMENTS

| EP | 1 439 174 A1 | 7/2004 |
|---|---|---|
| WO | WO-96/40143 A1 | 12/1996 |
| WO | WO-99/01131 A | 1/1999 |
| WO | WO-99/18942 A1 | 4/1999 |
| WO | WO-01/12621 A1 | 2/2001 |
| WO | WO-03/035638 A | 5/2003 |
| WO | WO-03/105223 A | 12/2003 |
| WO | WO-2004/110990 A2 | 12/2004 |

OTHER PUBLICATIONS

Annals of the New York Academy of Sciences (2004), 1028(Signal Transduction and Communication in Cancer Cells), 423-431.*

* cited by examiner

*Primary Examiner*—James O Wilson
*Assistant Examiner*—Jeffrey H Murray
(74) *Attorney, Agent, or Firm*—Birch, Stewart, Kolasch & Birch, LLP

(57) ABSTRACT

The present invention is to provide a novel heterocyclic compound of the formula [I]:

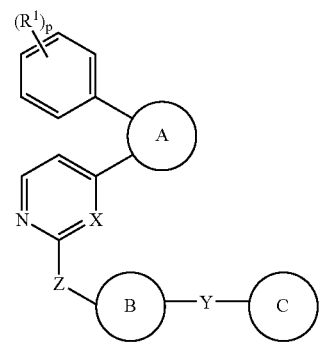

wherein $R^1$ is a halogen, nitro, an alkyl, etc.; $R^2$ is hydrogen, an alkyl, etc.; Ring A is 2-oxo-4-imidazolin-3,4-diyl, etc.; Ring B is a cycloalkyl, monocyclic saturated heterocyclic group; X is CH, N; Y is a single bond, CO, $SO_2$; Z is O, NH, etc.; and Ring C is an aryl, a heterocyclic group,
or a pharmaceutically acceptable salt thereof, which is useful as a p38 MAP kinase inhibitor.

11 Claims, No Drawings

HETEROCYCLIC COMPOUND WHICH MAY BE USED AS A MEDICINE HAVING P38 MAP KINASE INHIBITORY ACTIVITY

This application is the national phase of PCT application PCT/JP2005/008564 filed on Apr. 28, 2005 and claims priority under 35 U.S.C. 119(e) on U.S. Provisional Application No(s). 60/566,089 filed on Apr. 29, 2004 and under 35 U.S.C. 119(a) on Patent Application No(s). 2004-133204 and 2005-007832 filed in Japan on Apr. 28, 2004 and Jan. 14, 2005; respectively, all of which are hereby incorporated by reference.

TECHNICAL FIELD

The present invention relates to a novel heterocyclic compound having an excellent p38 MAP kinase-inhibitory activity and useful as a medicine.

BACKGROUND ART

Mitogen-activated protein (MAP) kinases is a kind of serine-threonine kinase which transfers a γ-phosphate group of adenosine triphosphoric acid (ATP) to a hydroxyl of specific serine or threonine constituting a protein, and participates in various cell responses against extra-cellular signals. The p38 MAP kinase is a protein with about 38 kDa which is subjected to cloning as a homologue of a MAP kinase.

The p38 MAP kinase is activated by an inflammatory cytokines such as tumor necrosis factor α (TNF-α), interleukin 1 (IL-1), etc., or by stress stimulation such as ultraviolet ray irradiation, etc. Also, it has been clarified that the p38 MAP kinase phosphorylates various transcription factor groups and kinase groups as substrates, these transcription factor groups and kinase groups are activated by the p38 MAP kinase, so that they contribute to progress in transcription, control after the transcription (stabilization of mRNA and progress of translation of protein) and stabilization of proteins, etc. with regard to various proteins which participate in inflammatory reaction such as inflammatory cytokines, etc. From these facts, it has been considered that the p38 MAP kinase deeply involves in various inflammatory reactions, etc. through control of production and/or signal transduction of inflammatory cytokines so that there is a high probability that an inhibitor of the p38 MAP kinase is to be an agent for treatment of inflammatory diseases and the like.

As an inhibitor of p38 MAP kinases, imidazole derivatives are known in (Patent Literature 1), 1,3-thiazole derivatives in (Patent Literature 2), 1,3-thiazole derivatives and 1,3-oxazole derivatives in (Patent Literature 3), imidazole derivatives, pyrrole derivatives, furan derivatives, 3-pyrazolin-5-one derivatives, pyrazole derivatives and thiophene derivatives, etc. in (Non-patent Literature 1), and 4-imidazolin-2-one compound in (Patent Literature 4), respectively.

[Patent Literature 1] JP 2000-503304-A
[Patent Literature 2] JP 2001-114690-A
[Patent Literature 3] JP 2001-114779-A
[Patent Literature 4] WO 03/035638
[Non-patent Literature 1] Expert Opinion on Therapeutic Patents, 2000, 10(1), p. 25-37

DISCLOSURE OF THE INVENTION

Problems to be Solved by the Invention

The problem to be solved by the present invention is to provide a novel compound having excellent p38 MAP kinase inhibitory activity and useful as a medicine.

Means to Solve the Problems

To solve the above-mentioned problems, the present inventors have earnestly studied, and as a result, they have found that the compound of the following formula has excellent p38 inhibitory activity whereby the present invention has been accomplished.

That is, the present invention is as follows.

1. A compound of the formula [I]:

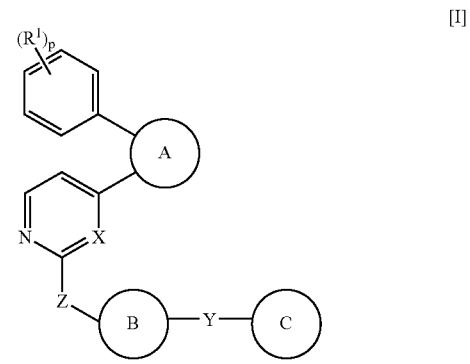

wherein $R^1$ is hydrogen, a halogen, nitro, an optionally substituted alkyl, an optionally substituted alkoxy, an optionally substituted amino, an optionally substituted carbamoyl, hydroxy or cyano, p is 1 or 2, provided that when p is 2, two $R^1$s may be the same or different from each other, Z is oxygen atom or —$N(R^2)$—, $R^2$ is hydrogen, an alkyl or an alkanoyl, Ring A is a ring selected from the following formulae:

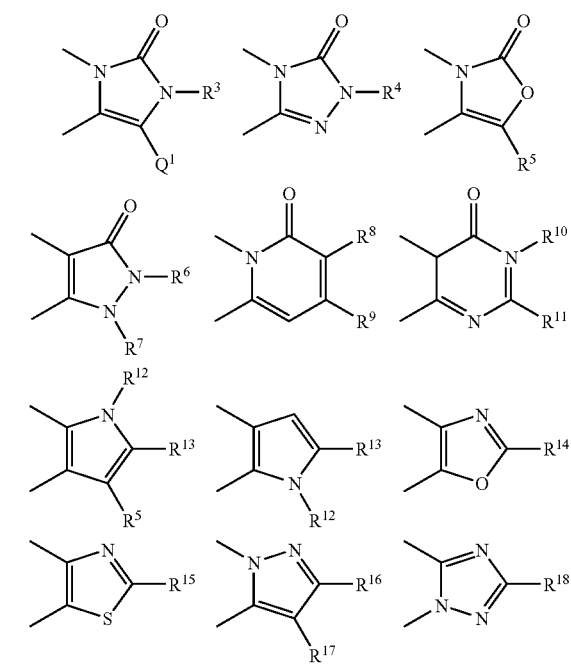

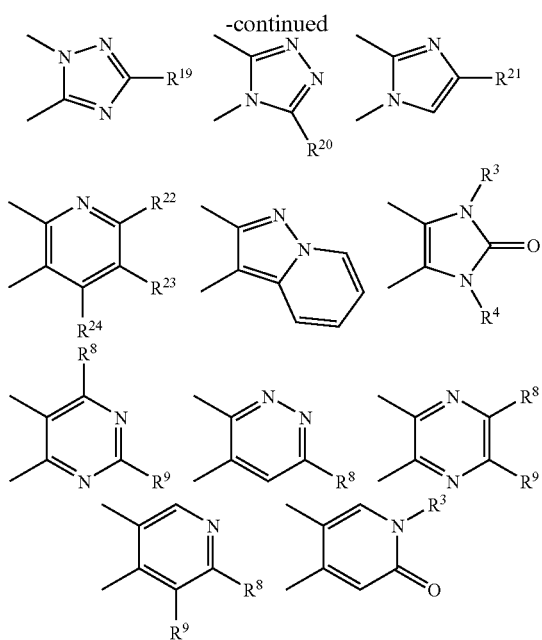

R³, R⁴, R⁶, R⁷, R¹⁰ and R¹² may be the same or different from each other, and each is $(CH_2)_n$—R^A, R^A is hydrogen, an optionally substituted alkyl, an optionally substituted alkoxyalkyl, an optionally substituted cycloalkyl, an optionally substituted phenyl or an optionally substituted heterocyclic group, n is 0 or an integer of 1 to 4, R⁵, R⁸, R⁹, R¹¹ and R¹³ to R²⁴ may be the same or different from each other, and each is hydrogen, a halogen, an optionally substituted alkyl, alkoxy, alkanoyl, an alkoxycarbonyl, an optionally substituted amino, an optionally substituted carbamoyl, an optionally substituted cycloalkyl, an optionally substituted aryl or an optionally substituted heterocyclic group, Q¹ is hydrogen, a halogen, cyano, an optionally substituted alkyl or an optionally substituted heterocyclic group, Ring B is a cycloalkane or a monocyclic saturated nitrogen-containing heterocyclic ring, X is CH or N, Y is a single bond, $SO_2$ or CO, Ring C is an aromatic hydrocarbon ring or an optionally substituted heterocyclic ring, or a pharmaceutically acceptable salt thereof.

2. The compound or a pharmaceutically acceptable salt thereof as mentioned in the above 1, wherein Ring A is

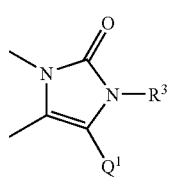

wherein R³ and Q¹ have the same meanings as the above.

3. The compound or a pharmaceutically acceptable salt thereof as mentioned in the above 1 or 2, wherein Z is —N(R²)— and R² has the same meaning as the above.

4. The compound or a pharmaceutically acceptable salt thereof as mentioned in any one of the above 1 to 3, wherein R² is hydrogen.

5. The compound or a pharmaceutically acceptable salt thereof as mentioned in any one of the above 1 to 4, wherein Ring B is a $C_{5-7}$ cycloalkane.

6. The compound or a pharmaceutically acceptable salt thereof as mentioned in any one of the above 1 to 5, wherein Ring B is cyclohexane.

7. The compound or a pharmaceutically acceptable salt thereof as mentioned in the above 5 or 6, wherein Y is a single bond.

8. The compound or a pharmaceutically acceptable salt thereof as mentioned in any one of the above 5 to 7, wherein Ring C is a heterocyclic ring which may be substituted by 1 to 3 groups independently selected from oxo, an alkyl, alkanoyl, alkylsulfonyl, alkoxycarbonyl, hydroxy and an optionally substituted amino.

9. The compound or a pharmaceutically acceptable salt thereof as mentioned in any one of the above 5 to 8, wherein Ring C is a ring selected from the following formulae:

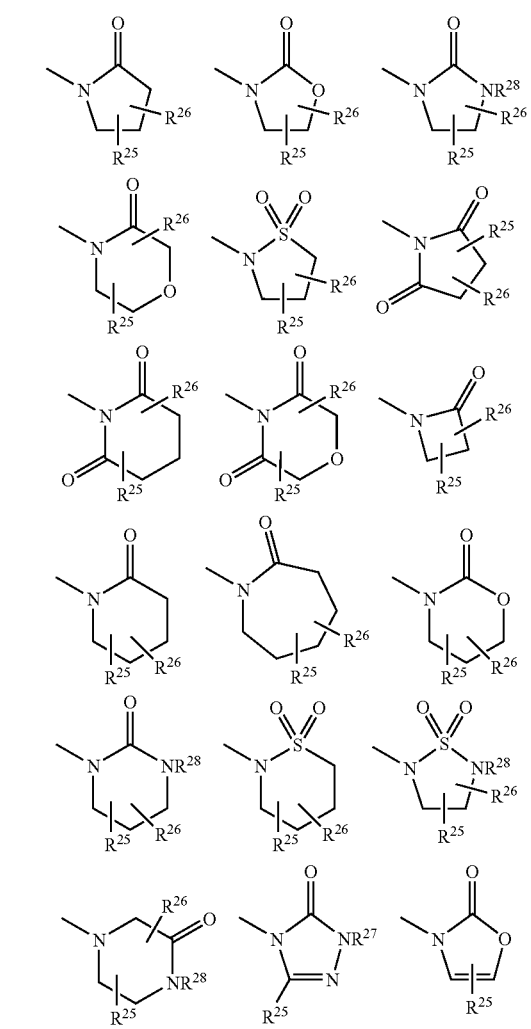

-continued

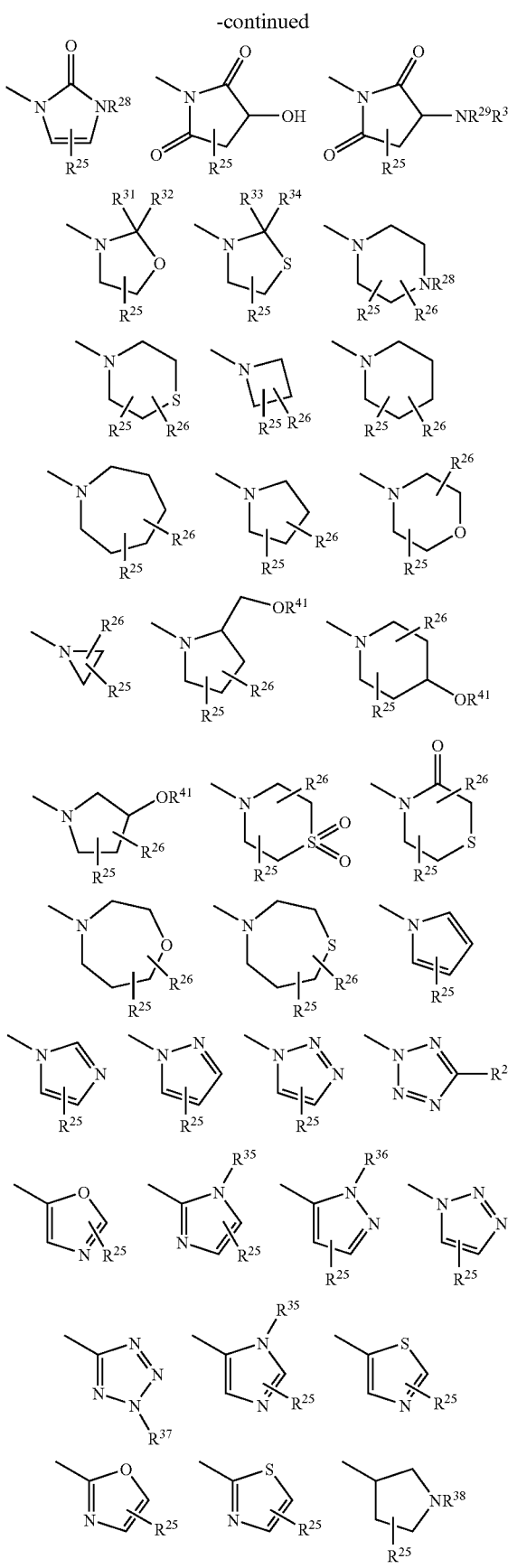

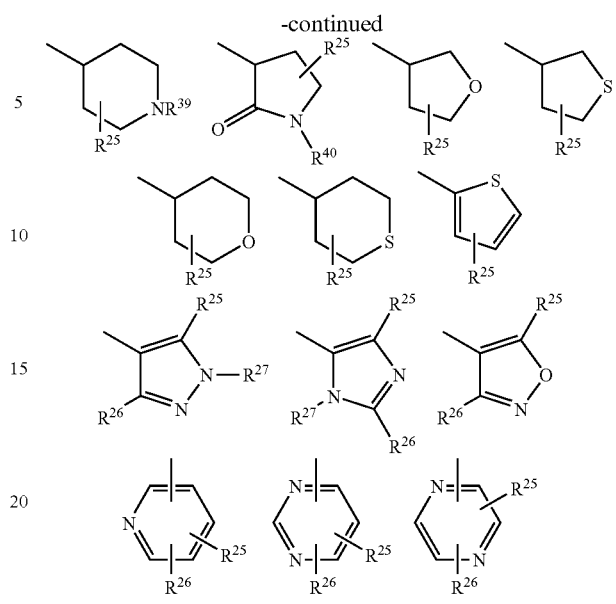

wherein $R^{25}$, $R^{26}$, $R^{31}$ to $R^{37}$ and $R^{41}$ may be the same or different from each other, and each is hydrogen, an alkyl, hydroxy, an alkoxy or an alkoxyalkyl, $R^{27}$ to $R^{30}$, $R^{38}$ and $R^{39}$ may be the same or different from each other, and each is hydrogen, an alkyl or an amino-protective group.

10. The compound or a pharmaceutically acceptable salt thereof as mentioned in any one of the above 5 to 9, wherein Ring C is the following groups

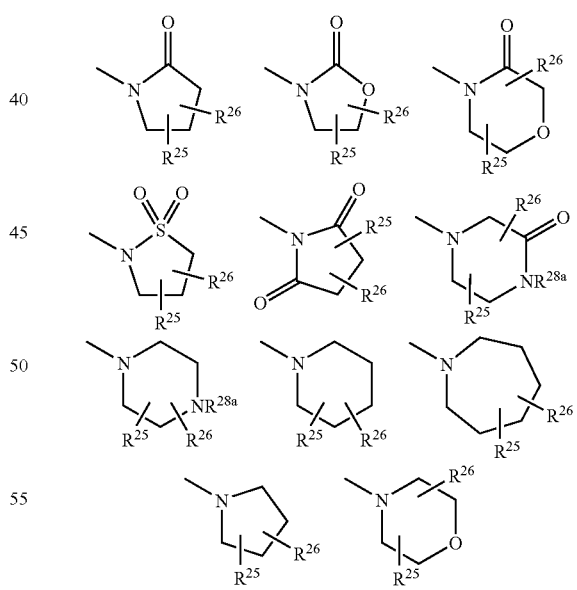

wherein $R^{28a}$ is hydrogen, an alkyl, an alkanoyl, an alkoxycarbonyl or an alkylsulfonyl, and other symbols have the same meanings as the above.

11. The compound or a pharmaceutically acceptable salt thereof as mentioned in any one of the above 1 to 3, wherein Ring B is a 5 to 7-membered monocyclic saturated nitrogen-containing heterocyclic ring.

12. The compound or a pharmaceutically acceptable salt thereof as mentioned in any one of the above 1 to 3, wherein Ring B is piperidine.

13. The compound or a pharmaceutically acceptable salt thereof as mentioned in the above 11 or 12, wherein Y is $SO_2$ or CO.

14. The compound or a pharmaceutically acceptable salt thereof as mentioned in any one of the above 11 to 13, wherein Ring C is an aromatic hydrocarbon ring, or a ring selected from the following formulae:

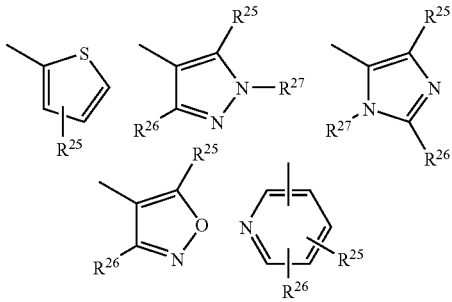

wherein $R^{25}$, $R^{26}$ and $R^{27}$ have the same meanings as the above.

15. The compound or a pharmaceutically acceptable salt thereof as mentioned in any one of the above 1 to 14, wherein $R^1$ is a halogen or an optionally substituted alkyl.

16. The compound or a pharmaceutically acceptable salt thereof as mentioned in any one of the above 1, to 15, wherein $R^1$ is chlorine, fluorine, methyl or trifluoromethyl.

17. The compound or a pharmaceutically acceptable salt thereof as mentioned in the above 15 or 16, wherein p is 1, and the binding position of $R^1$ is 4-position or 3-position.

18. The compound or a pharmaceutically acceptable salt thereof as mentioned in any one of the above 15 to 17, wherein p is 1, and the binding position of $R^1$ is 3-position.

19. The compound or a pharmaceutically acceptable salt thereof as mentioned in any one of the above 1 to 18, wherein $R^4$ is an optionally substituted alkyl, an optionally substituted heterocyclic group, phenyl or a cycloalkyl, and n is 0 or 1.

20. The compound or a pharmaceutically acceptable salt thereof as mentioned in any one of the above 1 to 19, wherein $R^4$ is 4-tetrahydropyranyl and n is 0.

21. A compound of the formula:

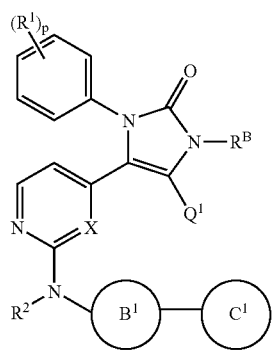

[Ia]

wherein $R^{1a}$ is a halogen or an optionally substituted alkyl, p is 1 or 2, provided that when p is 2, two $R^{1a}$s may be the same or different from each other, $R^2$ is hydrogen, an alkyl or an alkanoyl, $R^B$ is an optionally substituted alkyl or an optionally substituted heterocyclic group, $Q^1$ is hydrogen, a halogen, cyano, an optionally substituted alkyl or an optionally substituted heterocyclic group, Ring $B^1$ is a cycloalkane X is CH or N, Ring $C^1$ is an optionally substituted heterocyclic ring, or a pharmaceutically acceptable salt thereof.

22. The compound or a pharmaceutically acceptable salt thereof as mentioned in the above 21, wherein p is 1, and $R^{1a}$ is chlorine, fluorine, methyl or trifluoromethyl.

23. The compound or a pharmaceutically acceptable salt thereof as mentioned in the above 21 or 22, wherein p is 1, and the binding position of $R^{1a}$ is 4-position or 3-position.

24. The compound or a pharmaceutically acceptable salt thereof as mentioned in any one of the above 21 to 23, wherein p is 1, and the binding position of $R^{1a}$ is 3-position.

25. The compound or a pharmaceutically acceptable salt thereof as mentioned in any one of the above 21 to 24, wherein $R^2$ is hydrogen.

26. The compound or a pharmaceutically acceptable salt thereof as mentioned in any one of the above 21 to 25, wherein $R^B$ is an optionally substituted heterocyclic group.

27. The compound or a pharmaceutically acceptable salt thereof as mentioned in any one of the above 21 to 26, wherein $R^B$ is 4-tetrahydropyranyl.

28. The compound or a pharmaceutically acceptable salt thereof as mentioned in any one of the above 21 to 27, wherein $Q^1$ is hydrogen, bromine, chlorine, cyano or aminomethyl.

29. The compound or a pharmaceutically acceptable salt thereof as mentioned in any one of the above 21 to 28, wherein Ring $B^1$ is cyclohexane.

30. The compound or a pharmaceutically acceptable salt thereof as mentioned in any one of the above 21 to 29, wherein X is N.

31. The compound or a pharmaceutically acceptable salt thereof as mentioned in any one of the above 21 to 30, wherein Ring $C^1$ is a 5- to 7-membered saturated heterocyclic ring which contains 1 or 2 hetero atoms independently selected from nitrogen atom, oxygen atom and sulfur atom, and which may be substituted by the group selected from the group consisting of oxo(s), alkyl(s), hydroxy(s), alkoxy(s), alkanoyl(s), alkoxycarbonyl(s) and alkylsulfonyl(s).

32. The compound or a pharmaceutically acceptable salt thereof as mentioned in the above 31, wherein the heterocyclic ring is pyrrolidine, isothiazolidine, oxazolidine, piperidine, piperazine, morpholine or homopiperidine.

33. The compound or a pharmaceutically acceptable salt thereof as mentioned in any one of the above 21 to 32, wherein Ring $C^1$ is the following groups

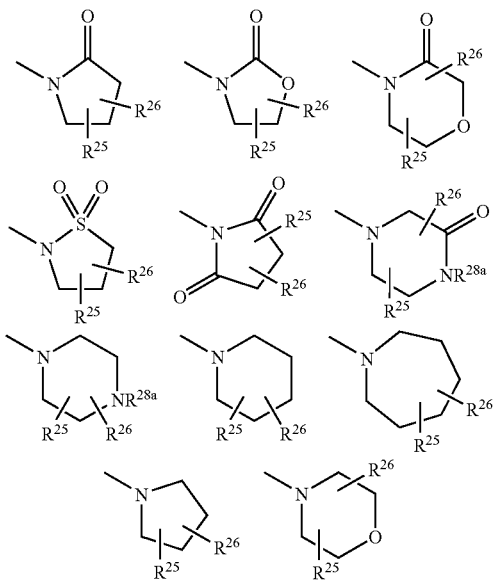

wherein $R^{28a}$ is hydrogen, an alkyl, an alkanoyl, an alkoxycarbonyl or an alkylsulfonyl, and other symbols have the same meanings as defined above.

34. A medicine comprising the compound or a pharmaceutically acceptable salt thereof as mentioned in any one of the above 1 to 33.

35. A p38 MAP kinase inhibitor containing the compound or a pharmaceutically acceptable salt thereof as mentioned in any one of the above 1 to 33.

36. A prophylaxis or treatment agent for diseases to which excessive production of inflammatory mediator pertains to which p38 MAP kinase pertains which comprises the compound or a pharmaceutically acceptable salt thereof as mentioned in any one of the above 1 to 33 as an effective ingredient.

37. The prophylaxis or treatment agent according to the above-mentioned 36, wherein the disease to which excessive production of inflammatory mediator pertains is arthritis.

BEST MODE FOR CARRYING OUT THE INVENTION

In the following, the respective groups represented by the respective symbols in the present specification will be explained.

"Halogen" includes fluorine, chlorine, bromine and iodine, preferably fluorine and chlorine.

"Alkyl" and the alkyl in the "alkoxyalkyl", "alkylthio", "alkylsulfinyl" and "alkylsulfonyl" is exemplified by, for example, a straight or branched chain $C_{1-6}$ alkyl, preferably $C_{1-4}$ alkyl, and specifically by methyl, ethyl, propyl, isopropyl, butyl, isobutyl, tert-butyl, pentyl, hexyl, etc.

"Alkoxy" and the alkoxy in the "alkoxyalkyl" and "alkoxycarbonyl" is exemplified by, for example, a straight or branched chain $C_{1-6}$ alkoxy, preferably $C_{1-4}$ alkoxy, and specifically by methoxy, ethoxy, propoxy, isopropoxy, butoxy, tert-butoxy, pentyloxy, hexyloxy, etc.

"Alkanoyl" is exemplified by, for example, a straight or branched chain $C_{2-7}$ alkanoyl, preferably $C_{2-5}$ alkanoyl, and specifically by acetyl, propionyl, butyryl, pentanoyl, etc.

"Cycloalkyl" is exemplified by, for example, $C_{3-8}$, preferably $C_{3-6}$ cycloalkyl, and specifically by cyclopropyl, cyclobutyl, cyclopentyl, cyclohexyl, cycloheptyl, etc.

"Cycloalkane" is exemplified by, for example, $C_{3-8}$, preferably $C_{3-6}$ cycloalkane, and specifically by cyclopropane, cyclobutane, cyclopentane, cyclohexane, cycloheptane, etc.

"Aryl" and the aryl in the "arylsulfonyl" is exemplified by, for example, $C_{6-14}$, preferably $C_{6-10}$ monocyclic, dicyclic or tricyclic aryl, and specifically by phenyl, naphthyl, phenanthryl, anthryl, etc., particularly phenyl and naphthyl are preferred.

"Aromatic hydrocarbon ring" is exemplified by, for example, $C_{6-14}$, preferably $C_{6-10}$ monocyclic, dicyclic or tricyclic aromatic hydrocarbon ring, and specifically by benzene, naphthalene, phenanthrene, anthracene, etc., particularly benzene and naphthalene are preferred.

"Heterocyclic group" is exemplified by, for example, a monocyclic, dicyclic or tricyclic heterocyclic group which contains 1 to 4 hetero atoms independently selected from nitrogen atom, oxygen atom and sulfur atom, and a part or whole portion of which may be saturated. There may be preferably mentioned a 5 or 6-membered monocyclic heterocyclic group, specifically mentioned are furyl, tetrahydrofuryl, tetrahydropyranyl, tetrahydrothiapyranyl, thienyl, tetrahydrothienyl, thiazolyl, isothiazolyl, tetrahydroisothiazolyl, oxazolyl, isoxazolyl, oxadiazolyl, tetrazolyl, pyrrolyl, pyrrolidinyl, pyrrolinyl, imidazolidinyl, imidazolinyl, pyrazolidinyl, pyridyl, pyridazinyl, pyrimidinyl, hexahydropyrimidinyl, pyrazinyl, triazinyl, piperidyl, pyrazolyl, piperazinyl, morpholinyl, dioxanyl, imidazolyl, triazolyl, pyrazolinyl, thiazinyl, tetrahydro-thiazinyl, etc.

"Heterocyclic ring" is exemplified by, for example, a monocyclic, dicyclic or tricyclic heterocyclic ring containing 1 to 4 hetero atoms independently selected from nitrogen atom, oxygen atom and sulfur atom, a part or whole portion of which may be saturated. There may be preferably mentioned a 5 or 6-membered monocyclic heterocyclic ring, specifically mentioned are furan, tetrahydrofuran, tetrahydropyran, tetrahydrothiapyran, thiophene, tetrahydro-thiophene, thiazole, isothiazole, tetrahydroisothiazole, oxazole, isoxazole, oxadiazole, tetrazole, pyrrole, pyrrolidine, pyrroline, imidazolidine, imidazoline, pyrazolidine, pyridine, pyridazine, pyrimidine, hexahydro-pyrimidine, pyrazine, triazine, piperidine, pyrazole, piperazine, morpholine, dioxane, imidazole, triazole, pyrazoline, thiazine, tetrahydrothiazine, etc.

"Monocyclic saturated nitrogen-containing heterocyclic ring" is exemplified by, for example, a 4 to 7-membered monocyclic saturated heterocyclic ring having 1 to 2 nitrogen atoms, and further may have 1 to 2 oxygen atom(s) or sulfur atom(s), and specifically by pyrrolidine, piperidine, homopiperidine, etc.

The substituent(s) for "the optionally substituted alkyl" of $R^1$ is exemplified by, for example, a halogen, hydroxy, amino, etc. The alkyl may be substituted by 1 to 3 substituents mentioned above, and when a number of the substituent(s) is two or more, the respective substituents may be the same or different from each other. Specific examples of the substituted alkyl include hydroxymethyl, trifluoromethyl, aminomethyl, chloroethyl, etc.

The substituent(s) for "the optionally substituted alkoxy" of $R^1$ is exemplified by, for example, hydroxy, amino, etc. The alkoxy may have X to 3 substituents mentioned above, and when a number of the substituent(s) is two or more, the respective substituents may be the same or different from each other.

The substituent(s) for "the optionally substituted amino" of $R^1$ is exemplified by, for example, an alkyl (the alkyl may be substituted by 1 to 3 groups independently selected from the group consisting of an alkoxy, amino and carboxy), alkanoyl, etc. The amino may be, for example, substituted by 1 or 2 substituent(s), and when a number of the substituent(s) is two, the respective substituents may be the same or different from each other.

The substituent(s) for "the optionally substituted carbamoyl" of $R^1$ is exemplified by, for example, an alkyl, etc. The carbamoyl may be substituted by 1 or 2 substituent(s) mentioned above, and when a number of the substituent(s) is two, the respective substituents may be the same or different from each other.

$R^1$ is preferably a halogen, nitro, optionally substituted alkyl; optionally substituted alkoxy, optionally substituted amino and cyano. Particularly preferred are a halogen, $C_1$ to $C_4$ alkyl which may be substituted by halogen(s), $C_1$ to $C_4$ alkoxy, etc., and specific examples thereof include a fluorine, chlorine, methyl, trifluoromethyl, methoxy, etc.

The substituent(s) for "the optionally substituted alkyl" of $R^4$ is exemplified by, for example, an alkynyl, cyano, alkoxy, hydroxy, amino (the amino may be substituted by 1 or 2 substituent(s) independently selected from the group consisting of an alkyl, alkanoyl and alkylsulfonyl), carboxy, alkoxycarbonyl, carbamoyl (the carbamoyl may be substituted by 1 or 2 alkyl(s)), phenyl, naphthyl, etc. The alkyl may be, for example, substituted by 1 to 3 substituent(s) mentioned above, and when a number of the substituent(s) is two or more, the respective substituents may be the same or different from each other. Preferred examples of the substituent include cyano, alkoxy, hydroxy, amino, carboxy, carbamoyl which may be substituted by alkyl, phenyl, etc.

The substituent(s) for "the optionally substituted cycloalkyl" of $R^4$ is exemplified by, for example, (1) hydroxy, (2) alkoxy (the alkoxy may be substituted by 1 to 3 alkoxy(s)), (3) amino [the amino may be substituted by the same or different 1 or 2 group(s) independently selected from the groups of the following (i) to (v): (i) alkyl, (ii) alkanoyl, (iii) alkoxycarbonyl, (iv) carbamoyl (the carbamoyl may be substituted by 1 or 2 alkyl(s)), and (v) alkylsulfonyl], (4) carboxy, (5) alkyl [the alkyl may be substituted by a group selected from the group consisting of hydroxy, alkoxy and amino], (6) carbamoyl which may be substituted by alkyl(s), etc. The cycloalkyl may be, for example, substituted by 1 to 3 substituent(s) mentioned above, and when a number of the substituent(s) is two or more, the respective substituents may be the same or different from each other.

The substituent(s) for "the optionally substituted phenyl" of $R^4$ is exemplified by, for example, (1) a halogen, (2) nitro, (3) alkyl (the alkyl may be substituted by the same or different 1 to 3 group(s) selected from the group consisting of a halogen, hydroxy, amino, carboxy and phenylsulfonyl), (4) alkenyl, (5) cyano, (6) hydroxy, (7) alkoxy (the alkoxy may be substituted by the same or different 1 to 3 group(s) independently selected from the group consisting of a halogen, carboxy, alkoxycarbonyl, carbamoyl, phenyl and morpholinylcarbonyl), (8) amino [the amino may be substituted by the same or different 1 or 2 group(s) independently selected from the groups of the following (i) to (iv): (i) alkyl, (ii) alkanoyl, (iii) carbamoyl (the carbamoyl may be substituted by the same or different 1 or 2 group(s) independently selected from the group consisting of alkyl and cycloalkyl), and (iv) alkylsulfonyl], (9) alkanoyl, (10) carboxy, (11) alkoxycarbonyl, (12) carbamoyl [the carbamoyl may be substituted by one or two group(s) which may be the same or different from each other independently selected from the groups consisting of the following (i) and (ii): (i) alkyl (the alkyl may be substituted by 1 to 3 hydroxy(s)), and (ii) cycloalkyl], (13) alkylthio, (14) alkylsulfinyl, (15) alkylsulfonyl, (16) phenyl, (17) tetrazolyl, (18) heterocyclic group-substituted carbonyl (the heterocyclic group may be substituted by the same or different 1 to 3 group(s) independently selected from the group consisting of alkyl and alkoxycarbonyl), etc. When $R^1$ is an optionally substituted phenyl, the phenyl may be, for example, substituted by 1 to 3 group(s) mentioned above, and when a number of the substituent(s) is two or more, the respective substituents may be the same or different from each other. Preferred examples of the substituent include (1) a halogen, (2) alkyl (the alkyl may be substituted by the same or different 1 to 3 group(s) selected from the group consisting of a halogen, hydroxy, amino, carboxy and phenylsulfonyl), (3) cyano, (4) alkoxy (the alkoxy may be substituted by the same or different 1 to 3 group(s) selected from the group consisting of a halogen, carboxy, alkoxycarbonyl, carbamoyl, phenyl and morpholinylcarbonyl), etc. As a substituted position(s) of the substituent(s), it is not limited so long as it is a substitutable position, and particularly preferred position may be mentioned 2-position.

When $R^4$ is "the optionally, substituted heterocyclic group", the heterocyclic group is exemplified by the abovementioned heterocyclic group, preferably a 5 or 6-membered monocyclic heterocyclic group. Specific examples thereof include furyl, tetrahydrofuryl, thienyl, thiazolyl, isoxazolyl, oxadiazolyl, pyridyl, pyrimidinyl, pyrazinyl, piperidyl, pyrrolidinyl, pyrazolyl, tetrazolyl, tetrahydro-pyranyl, tetrahydrothiapyranyl, etc., particularly preferably piperidyl, tetrahydropyranyl, etc. Also, a substituent(s) on the heterocyclic group is exemplified by, for example, a halogen, nitro, alkyl (the alkyl may be substituted by a group selected from the group consisting of hydroxy, alkoxy, carbamoyl optionally substituted by alkyl, and carboxy), cyano, hydroxy, amino, alkanoyl, carboxy, alkoxycarbonyl, carbamoyl (the carbamoyl may be substituted by 1 or 2 alkyl(s)), alkylsulfonyl, phenyl, oxo, etc. The heterocyclic group may be, for example, substituted by 1 to 3 substituent(s) mentioned above, and, when a number of the substituent(s) is two or more, the respective substituents may be the same or different from each other.

The preferred combination of n and $R^4$ in Compound [I] is exemplified by, for example, (1) those in which n is 0, and $R^4$ is an optionally substituted alkyl, (2) those in which n is 1, and $R^4$ is an optionally substituted cycloalkyl, (3) those in which n is 1, and $R^4$ is an optionally substituted phenyl, (4) those in which n is 1, and $R^4$ is an optionally substituted heterocyclic group, (5) those in which n is 0, and $R^4$ is an optionally substituted cycloalkyl, and (6) those in which n is 0, and $R^4$ is an optionally substituted heterocyclic group, etc. Particularly preferred are (1) those in which n is 0, and $R^4$ is an optionally substituted alkyl, (2) those in which n is 1, and $R^4$ is an optionally substituted phenyl, (3) those in which n is 0, and $R^4$ is optionally substituted cycloalkyl, and (4) those in which n is 0, and $R^4$ is an optionally substituted heterocyclic group, etc. Further preferred are (1) those in which h is 0, and $R^4$ is a $C_1$ to $C_4$ alkyl which may be substituted by hydroxy, (2) those in which n is 1, and $R^4$ is a phenyl (the phenyl may be substituted by a group(s) selected from the group consisting of a cyano, fluorine, chlorine and methyl), (3) those in which n is 0, and $R^4$ is a $C_3$ to $C_4$ cycloalkyl, and (4) those in which n is 0, and $R^4$ is a tetrahydropyranyl, etc.

The substituent(s) for "the optionally substituted alkyl" of $R^5$, $R^8$, $R^9$, $R^{11}$ and $R^{13}$ to $R^{24}$ is exemplified by, for example, a halogen, hydroxy, amino (the amino may be mono or disubstituted by a group selected from the group consisting of an alkyl, alkanoyl, alkoxycarbonyl and alkylsulfonyl), etc., and the alkyl may by substituted by 1 to 3 substituents mentioned above, and when a number of the substituent(s) is two or more, the respective substituents may be the same or different from each other.

The substituent(s) for "the optionally substituted amino" of $R^5$, $R^8$, $R^9$, $R^{11}$ and $R^{13}$ to $R^{24}$ and Ring C is exemplified by, for example, an alkyl, alkanoyl, alkoxycarbonyl, alkylsulfonyl, etc., the amino may be substituted by 1 or 2 substituents mentioned above, and when a number of the substituent(s) is two, the respective substituents may be the same or different from each other.

The substituent(s) for "the optionally substituted carbamoyl" of $R^5$, $R^8$, $R^9$, $R^{11}$ and $R^{13}$ to $R^{24}$ is exemplified by, for example, an alkyl, etc., the carbamoyl may be substituted by 1 or 2 substituents mentioned above, and when a number of the substituent(s) is two, the respective substituents may be the same or different from each other.

The substituent(s) for "the optionally substituted cycloalkyl" of $R^5$, $R^8$, $R^9$, $R^{11}$ and $R^{13}$ to $R^{24}$ is exemplified by, for example, a halogen, hydroxy, alkyl, alkoxy, amino (which may be mono- or di-substituted by alkyl or alkanoyl), etc., the cycloalkyl may be substituted by 1 or 2 substituents mentioned above, and when a number of the substituent(s) is two, the respective substituents may be the same or different from each other.

The substituent(s) for "the optionally substituted-aryl" of $R^5$, $R^8$, $R^9$, $R^{11}$ and $R^{13}$ to $R^{24}$ is exemplified by, for example, a halogen, hydroxy, alkyl optionally substituted by halogen, alkoxy, amino (which may be mono- or di-substituted by an alkyl or alkanoyl), etc., the aryl may be substituted by 1 or 2 substituents mentioned above, and when a number of the substituent(s) is two, the respective substituents may be the same or different from each other.

The substituent(s) for "the optionally substituted heterocyclic group" of $R^5$, $R^8$, $R^9$, $R^{11}$ and $R^{13}$ to $R^{24}$ is exemplified by, for example, a halogen, hydroxy, alkyl, alkoxy, amino (which may be mono- or di-substituted by alkyl or alkanoyl), etc., the heterocyclic group may be substituted by 1 or 2 substituents mentioned above, and when a number of the substituent(s) is two, the respective substituents may be the same or different from each other.

"The amino-protective group" of $R^{27}$ to $R^{30}$, $R^{38}$ and $R^{39}$ is exemplified by, for example, an amino-protective group described in T. W. Green, Protective Groups in Organic Synthesis, John Wiley & Sons Inc. (1981), specifically by alkanoyl, alkoxycarbonyl, alkylsulfonyl, optionally substituted arylsulfonyl (nitro, etc., are preferred as the substituent(s)), etc.

The substituent(s) for "the optionally substituted alkyl" of $Q^1$ is exemplified by an amino which may be substituted by an alkyl, an alkanoyl, and the like. Specific examples of the substituted alkyl include aminomethyl, N-methylaminomethyl, N,N-dimethylaminomethyl, N-acetylaminomethyl, and the like, and preferred is aminomethyl.

"The optionally substituted heterocyclic group" of $Q^1$ is preferably monocyclic saturated nitrogen-containing heterocyclic group, more preferably a 4 to 7-membered monocyclic saturated heterocyclic group having 1 to 2 nitrogen atoms, and further may have 1 to 2 oxygen atom(s) or sulfur atom(s). Examples of such heterocyclic group include pyrrolidine, piperidine, homopiperidine, and the like, preferred are pyrrolidine or piperidine.

The substituent(s) for "the optionally substituted heterocyclic group" of $Q^1$ is exemplified by an alkyl, an alkanoyl, an alkoxycarbonyl, an alkylsulfonyl and the like.

"Heterocyclic ring" of Ring C is exemplified by, for example, a 3 to 7-membered, preferably 5 or 6-membered heterocyclic ring containing 1 to 4 hetero atoms independently selected from nitrogen atom, oxygen atom and sulfur atom, a part or whole of which may be saturated. The heterocyclic ring may be substituted by 1 to 3 group(s) independently selected from oxo, alkyl, alkoxyalkyl, alkylsulfonyl, optionally substituted arylsulfonyl, hydroxy, alkoxy, alkanoyl, alkoxycarbonyl and optionally substituted amino as a substituent(s). Specific examples of the optionally substituted heterocyclic ring include the following groups.

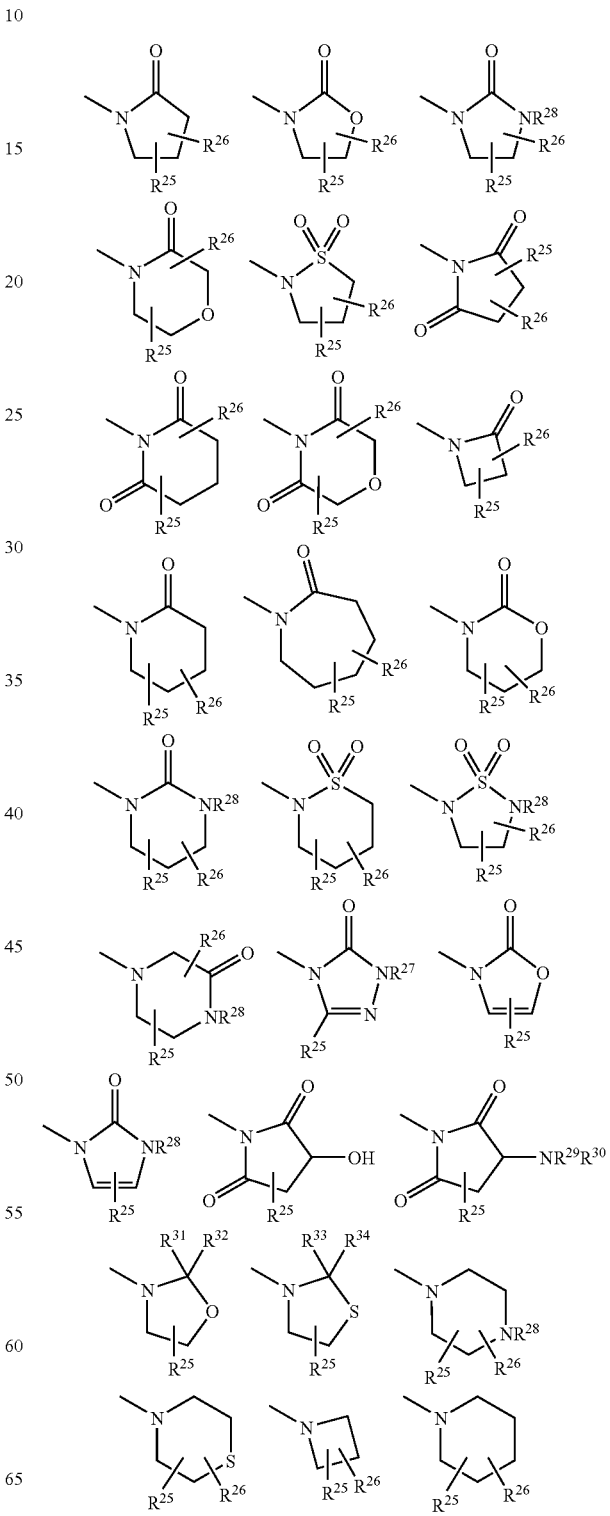

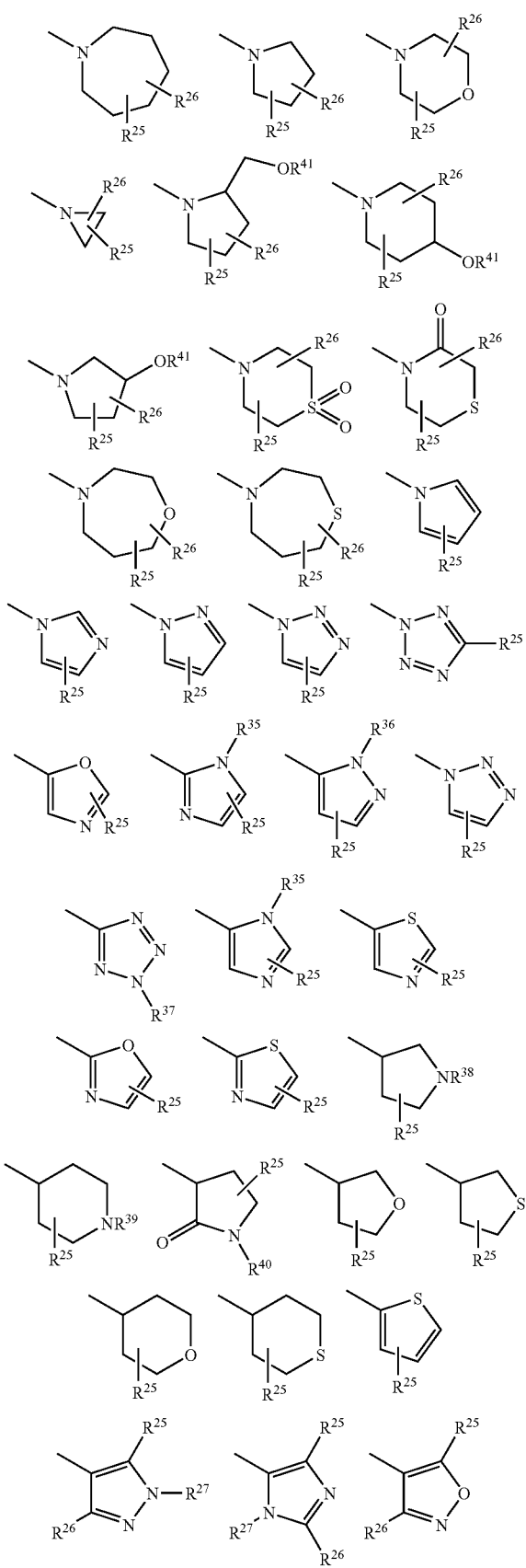

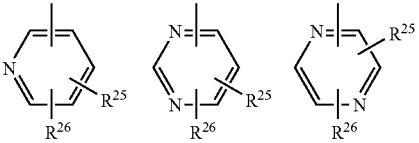

wherein the respective symbols have the same meanings as defined above.

Preferred examples of the above-mentioned heterocyclic ring include the following groups.

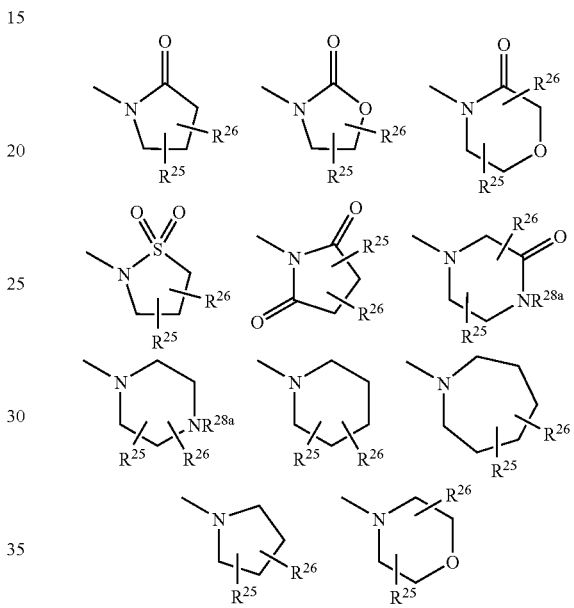

wherein respective symbols have the same meanings as defined above.

A binding position of —Y-Ring C at Ring B is preferably a 3-position, 4-position, 5-position, etc., when the binding position of —Z— is 1-position. When Ring B is a 6-membered ring, a 4-position is particularly preferred.

When Y is $SO_2$ or CO, Ring B is preferably a monocyclic saturated nitrogen-containing heterocyclic ring containing NH, particularly preferred is a heterocyclic ring in which Y binds to a nitrogen atom of the NH.

When Y is a single bond, Ring C is preferably a heterocyclic ring containing NH in which a part or whole of which is saturated, particularly preferred is a heterocyclic ring in which Y binds to a nitrogen atom of the NH.

A binding position of $R^1$ is preferably a 3-position or 4-position of phenyl, more preferably 3-position.

In Compound [I] of the present invention, there exists an optical isomer based on an asymmetric carbon(s), and the present invention includes any of these optical isomers and a mixture thereof. Compound. [I] can be used for a pharmaceutical use, either in a free form or in a form of a pharmaceutically acceptable salt. The pharmaceutically acceptable salt of Compound [I] is exemplified by, for example, inorganic acid salts such as hydrochloride, sulfate, phosphate or hydrobromide, organic acid salts such as acetate, fumarate, oxalate, citrate, methane-sulfonate, benzenesulfonate, tosylate or maleate. Further, when the compound has a substituent such as carboxy, etc., there may be mentioned a salt with a base (for example, alkali metal salts such as a sodium salt, a potassium salt, etc., or alkaline earth metal salts such as a calcium salt, etc.).

Compound [I] of the present invention or a salt thereof also includes an internal salt thereof, and a solvate thereof such as a hydrate, and the like.

Compound [I] of the present invention can be produced by the following method.

[Method A]

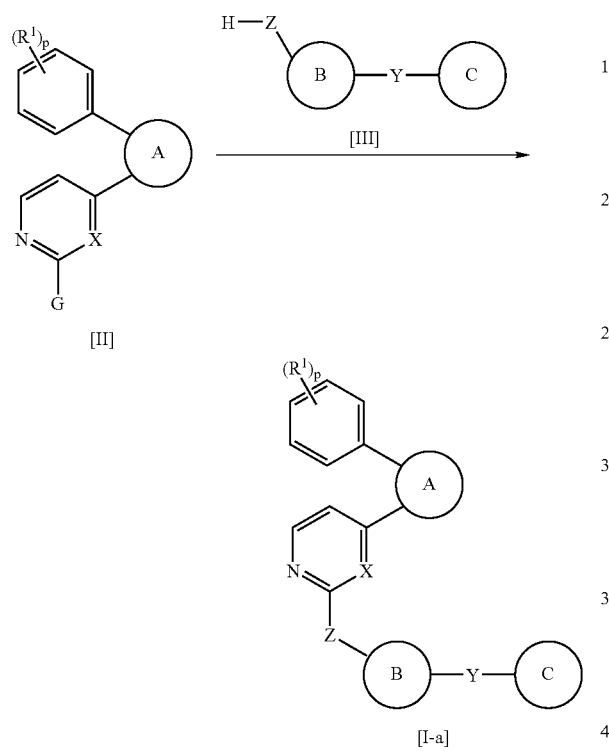

wherein G is a halogen, methylthio, methylsulfinyl or methylsulfonyl, other symbols have the same meanings as defined above.

When G in Compound [II] is a halogen, the reaction of Compound [II] and Compound [III] can be carried out in the presence of a catalyst, a base and an additive in a solvent (Journal of Organic Chemistry, 61, 7240(1996)). Any solvent may be used so long as it has no adverse effect on the reaction, and examples of such solvent include, for example, toluene, xylene, dimethoxyethane, dioxane, etc. Examples of the catalyst include, for example, palladium acetate, dipalladium bis(dibenzylideneacetone), etc. Examples of the base include, for example, sodium tert-butoxide, potassium tert-butoxide, lithium tert-butoxide, triethylamine, etc. Examples of the additive include 2,2'-bis(diphenylphosphino)-1,1'-binaphthyl, etc. The present reaction suitably proceeds at 30 to 150° C., particularly at 60 to 80° C.

When G in Compound [II] is methylthio, methylsulfinyl or methylsulfonyl, the reaction of Compound [II] and Compound [III] can be carried out in a solvent. Any solvent may be used so long as it has no adverse effect on the reaction, and examples of such solvent include, for example, dioxane, THF, DMF, DMSO, etc. The present reaction suitably proceeds at 0 to 150° C., particularly at 50 to 100° C.

[Method B]

The compound of the following formula, [I-b] included in Compound [I] of the present invention can be produced by the following method.

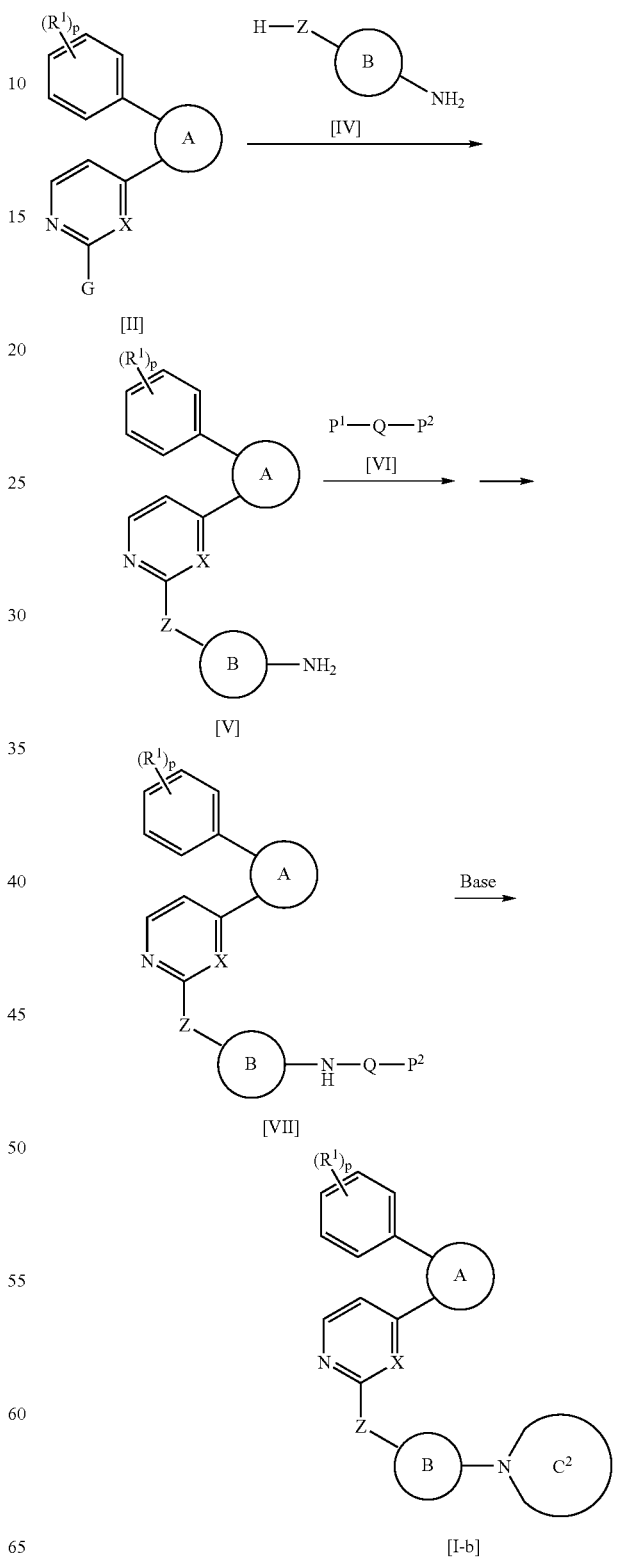

wherein P¹ and P² may be the same or different from each other, and each is a halogen, chloroformyl, carboxy, alkylsulfonyloxy or isocyanate, Q is an alkyl (the alkyl may be interposed by 1 to 2 oxygen atom, nitrogen atom, sulfur atom, etc. in the alkyl chain) which may have 1 to 4 groups selected from oxo, alkyl, hydroxy, an optionally substituted amino and double bond, Ring C² is a group selected from the following formulae,

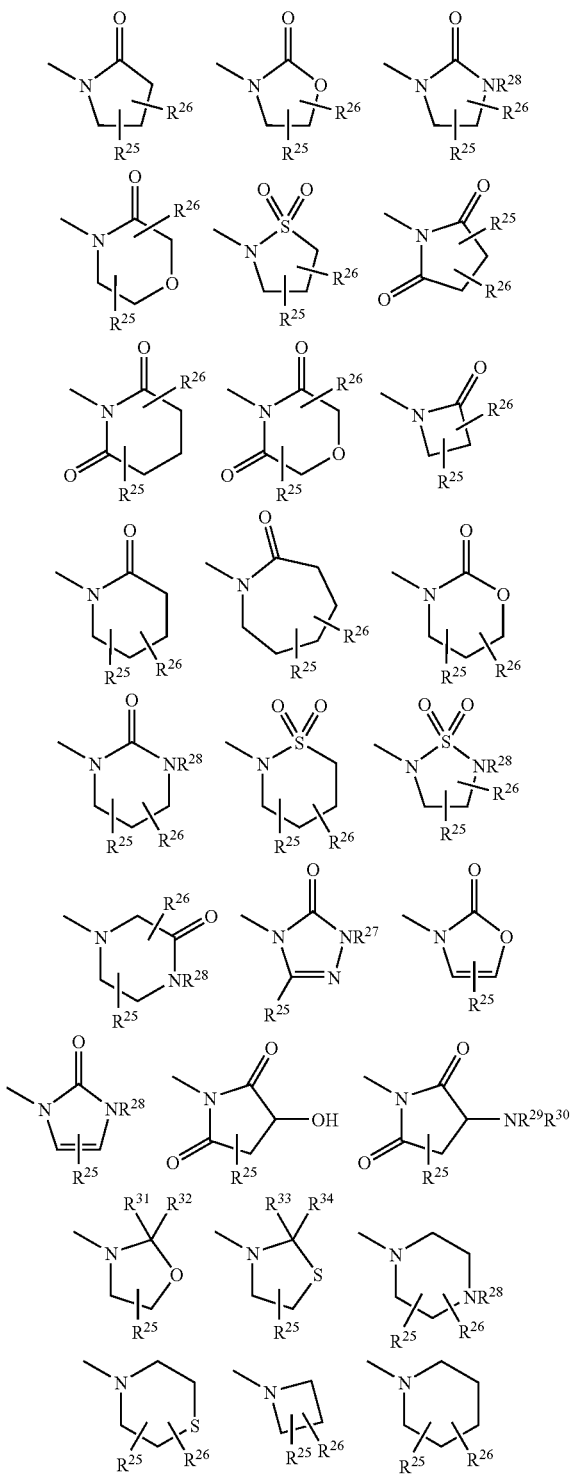

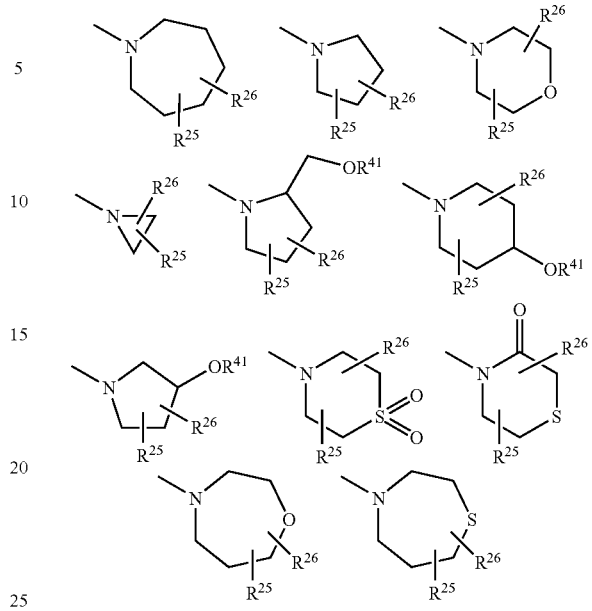

other symbols have the same meanings as defined above.

The reaction of Compound [II] and Compound [IV] can be carried out in the same manner as in Method A.

When P¹ of Compound [VI] is a halogen or alkylsulfonyloxy, the reaction of Compound [V] and Compound [VI] can be carried out in the presence of a base in a solvent. Examples of the solvent include chloroform, dichloromethane, DMF, DMSO, dioxane, THF, etc. Examples of the base include triethylamine, diisopropylethylamine, 4-methylmorpholine, pyridine, etc. The present reaction suitably proceeds at −40 to 100° C., particularly at −10 to 30° C.

When P¹ of Compound [VI] is isocyanate, the reaction can be carried out in a solvent. Examples of the solvent include chloroform, dichloromethane, DMF, DMSO, dioxane, THF, etc. The present reaction suitably proceeds at −40 to 100° C., particularly at −10 to 30° C.

When P¹ of Compound [VI] is carboxy, the reaction of Compound [V] and Compound [VI] can be carried out by treating with a condensing agent in a solvent. Any solvent may be used so long as it has no adverse effect on the reaction, and examples of such solvent include, for example, methylene chloride, chloroform, THF, DMF, etc. Examples of the condensing agent include, for example, 1,1'-carbonyldiimidazole, 1,3-dicyclohexylcarbodiimide, 1-(3-dimethylaminopropyl)-3-ethylcarbodiimide-hydrochloride, etc. The present reaction suitably proceeds at −40 to 100° C., particularly at −10 to 30° C.

Compound [VII] is treated with a base in a solvent to give Compound [I-b]. Examples of the solvent include DMF, DMSO, N,N-dimethylacetamide, etc. Examples of the base include sodium hydride, potassium tert-butoxide, etc. The present reaction suitably proceeds at 0 to 100° C., particularly at 30 to 80° C.

[Method C]

The compound of the following formula [I-c] included in Compound [I] of the present invention can be produced by the following method.

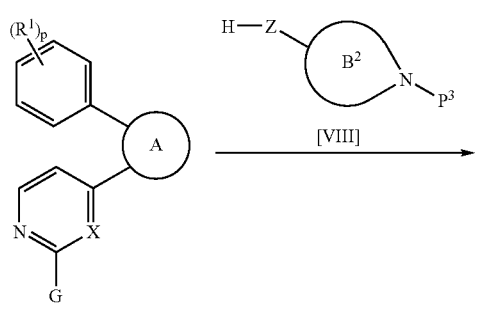

[II]

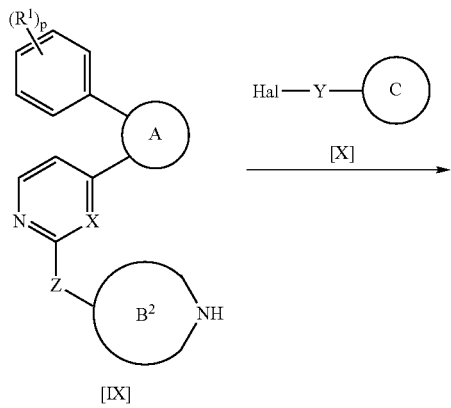

[IX]

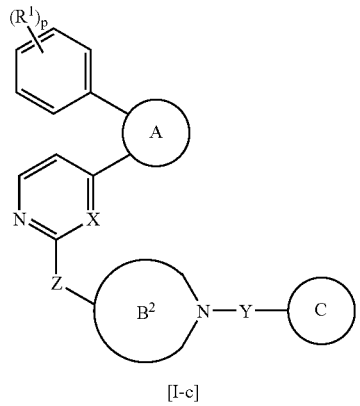

[I-c]

wherein Ring $B^2$ is a monocyclic saturated nitrogen-containing heterocyclic ring, Hal is a halogen, $P^3$ is an amino-protective group, and other symbols have the same meanings as defined above.

The reaction of Compound [II] and Compound [VIII] can be carried out in the same manner as in Method A, and the obtained compound is deprotected according to the conventional manner to give Compound [IX].

The reaction of Compound [IX] and Compound [X] can be carried out in the presence of a base in a solvent. Examples of the solvent include THF, dioxane, dichloromethane, chloroform, toluene, xylene, DMF, DMSO, etc. Examples of the base include sodium hydride, triethylamine, diisopropylethylamine, pyridine, 4-dimethylaminopyridine, etc. The present reaction suitably proceeds at −20 to 100° C., particularly at 0° C. to room temperature.

[Method D]

The Compound (I) in which Ring A is

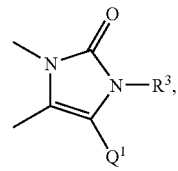

and $Q^1$ is an optionally substituted aminomethyl can be produced by the following method.

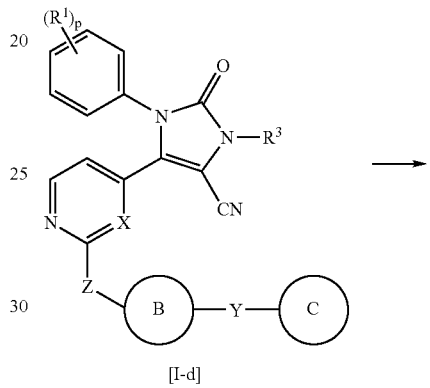

[I-d]

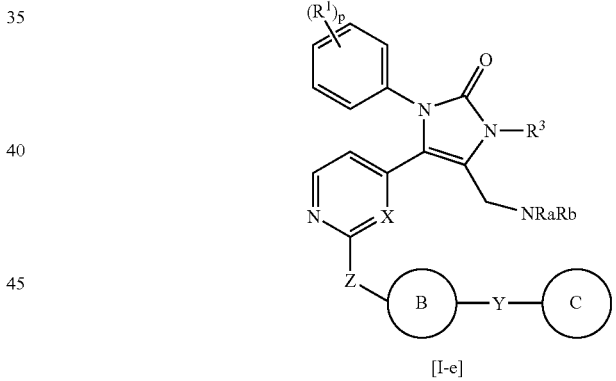

[I-e]

wherein Ra and Rb are the same or different from each other and each is hydrogen, an alkyl or an alkanoyl, and other symbols have the same meaning as defined above.

Compound [I-d], which is prepared in the same method as in Method A, is subjected to catalytic hydrogenation reaction or treated with reducing agent according to the conventional manner, and subjected to N-alkylation or N-alkanoylation if necessary to give Compound [I-e]. Examples of the catalyst of catalytic hydrogenation reaction include Raney nickel, and the like. Examples of the reducing agent include lithium aluminum hydride, sodium borohydride, and the like.

Compound [III] can be generally prepared by a known method. For example, the compound of the following formula [XIV] can be produced by the following method.

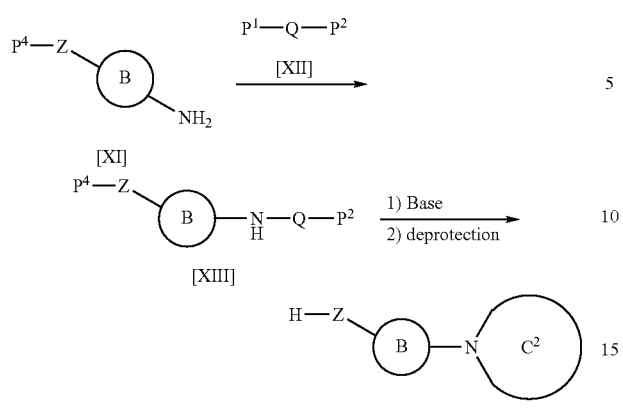

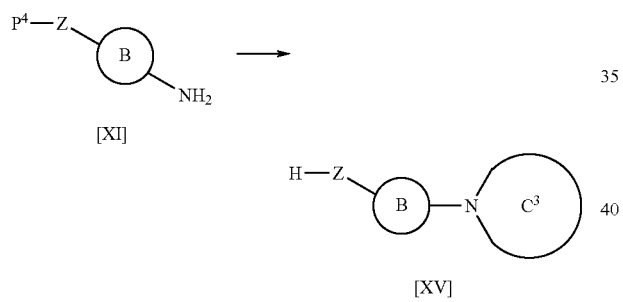

wherein $P^4$ is an amino-protective group or a protective group for hydroxy, and other symbols have the same meanings as defined above.

The present reaction can be carried out in the same manner as in Method B, and the obtained compound is deprotected according to the conventional manner to give Compound [XIV].

The compound of the following formula [XV] can be produced by the following method.

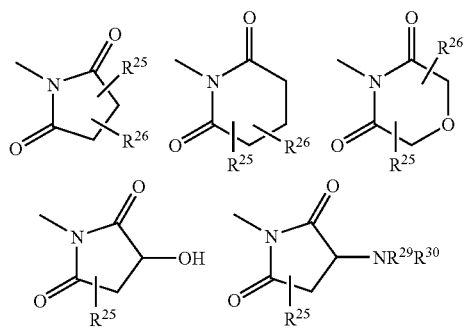

wherein Ring $C^3$ is a group selected from the following formulae, and other symbols have the same meanings as defined above.

The present reaction can be carried out by reacting Compound [XI] and the corresponding cyclic acid anhydride in the same manner as in the condensation reaction of Method B, and the obtained compound is deprotected to give Compound [XV].

The compound of the following formula [XIX] can be produced by the following method.

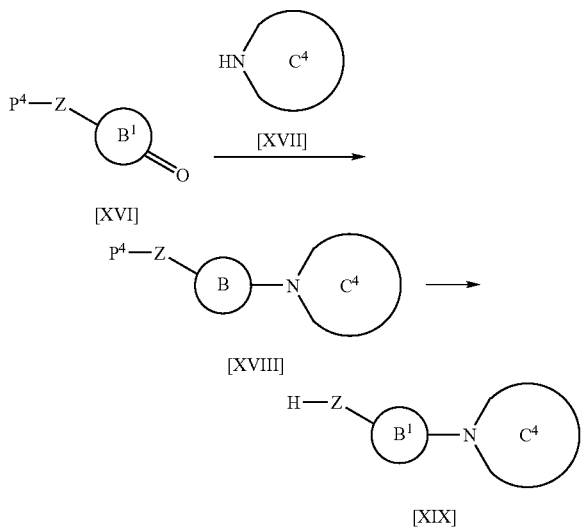

wherein Ring $C^4$ is

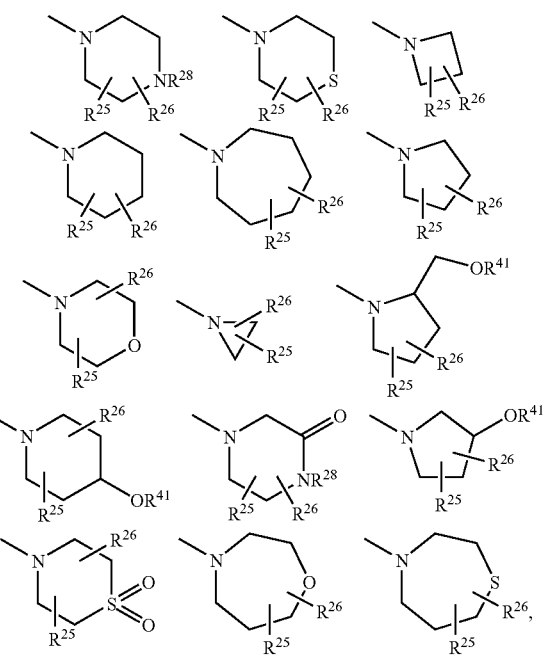

and other symbols have the same meanings as defined above.

Compound [XVI] is subjected to reductive amination reaction with Compound [XVII] in the presence of a reducing agent in a solvent to give Compound [XVIII]. Examples of the solvent include water, methanol, ethanol, chloroform, dichloroethane, ethyl acetate, acetic acid, benzene, toluene, xylene, DMF, DMSO or a mixture thereof. Examples of the reducing agent include sodium borohydride, sodium cyanoborohydride, sodium triacetoxyborohydride, etc. The present reaction suitably proceeds at −20° C. to 150° C. for 1 to 24 hours.

The obtained Compound [XVIII] is deprotected according to the conventional manner to give Compound [XIX].

Also, the compound of the following [XXII] can be produced by the following method.

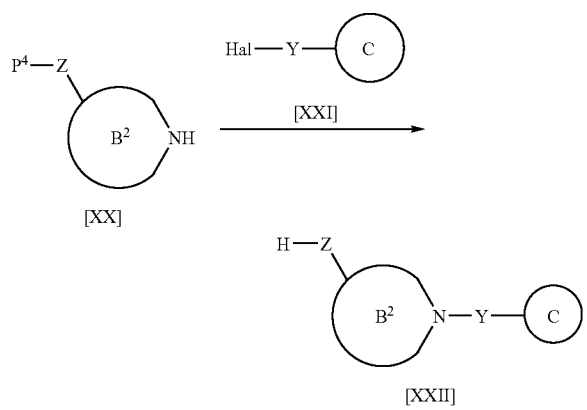

wherein the respective symbols have the same meanings as defined above.

The present reaction can be carried out in the same manner as in Method C, and the obtained compound is deprotected to give Compound [XXII].

Compound [II-b], which is the intermediate of Compound [I-d], can be produced by the following method.

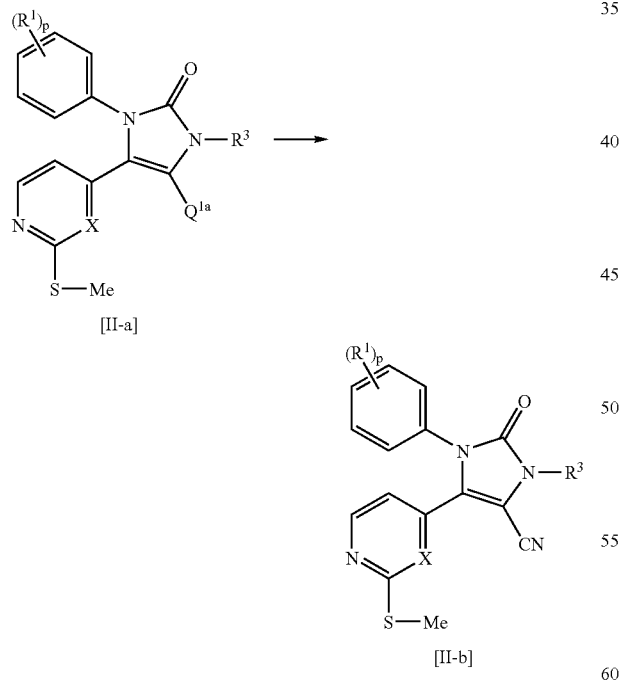

wherein $Q^{1a}$ is a halogen and other symbols have the same meaning as defined above.

Compound [II-a] is reacted with a cyanizing agent in a solvent to give Compound [II-b]. Examples of the cyanizing agent include sodium cyanide, cuprous cyanide, and the like. Examples of the solvent include acetonitrile, DMSO, DMF, a mixture thereof, and the like. The present reaction suitably proceeds at room temperature to 100° C. from 1 to 24 hours. Compound [II-d] may also be prepared using a palladium catalyst such as tetrakis(triphenylphosphine)palladium and a cyanizing agent such as zinc cyanide and potassium cyanide.

Compound [II] in which G is methylthio, methylsulfinyl or methylsulfonyl, Ring A is

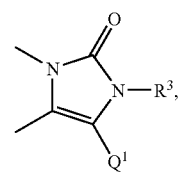

and $Q^1$ is a halogen, an alkyl or an optionally substituted heterocyclic group, can be produced by the following method.

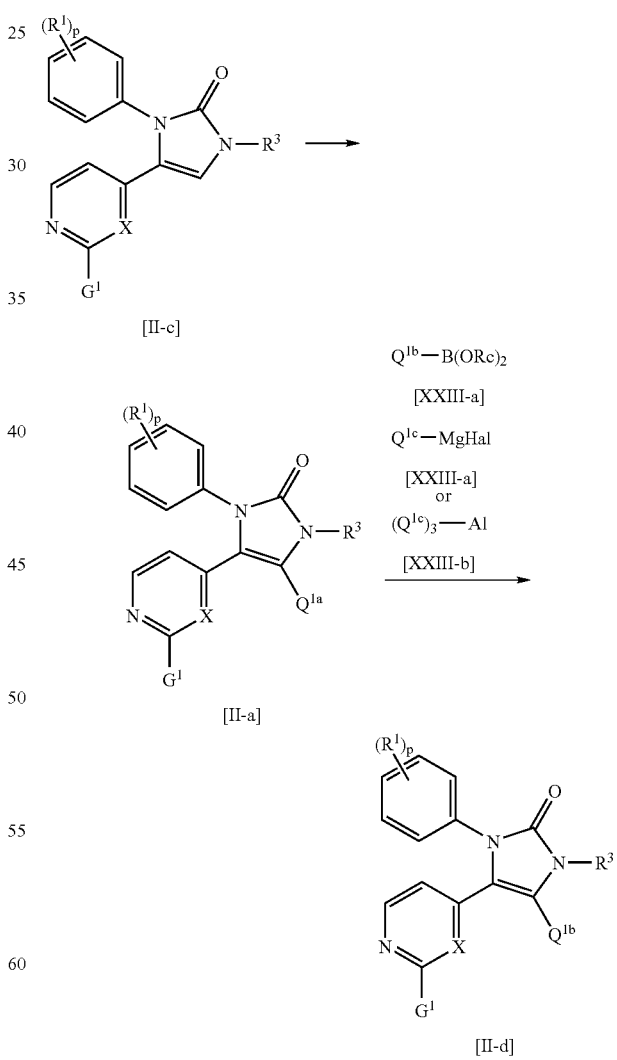

wherein $G^1$ is methylthio, methylsulfinyl or methylsulfonyl, $Q^{1b}$ is an alkyl or an optionally substituted heterocyclic group, $Q^{1c}$ is an alkyl, Rc is hydrogen or an alkyl, and other symbols have the same meaning as defined above.

Compound [II-c] is subjected to halogenation with a halogenating agent according to the conventional manner to give Compound [II-a]. Examples of the halogenating agent include bromine, chlorine, iodine, N-bromosuccinimide, N-chlorosuccinimide, and the like.

Compound [II-d] can be prepared by the following methods.

(1) According to the method described in Chem. Rev. 1995, 95, 2457-2483, Compound [II-a] is reacted with Compound [XXIII-a] in the presence of a palladium catalyst and a base to give Compound [II-d]. Example of the palladium catalyst include a zero-valent or divalent palladium catalyst such as [1,1-bis(diphenylphosphino)ferrocene]dichloropalladium, tetrakis(triphenylphosphine)palladium(0), bis(triphenylphosphine)palladium(II) dichloride, bis(tri-t-butylphosphine)palladium(0), bis(tricyclohexylphosphine)-palladium (0), tris(dibenzylideneacetone)dipalladium(0) and palladium (II) acetate. Examples of the base include an inorganic base such as alkali metal carbonate (potassium carbonate, cesium carbonate etc.), alkali metal hydroxide (potassium hydroxide, sodium hydroxide etc.), alkali metal phosphate (potassium phosphate etc.), alkali metal acetate (potassium acetate etc.), alkali metal fluoride (sodium fluoride etc.) and sodium t-butoxide, or an organic base such as triethylamine. Any solvent may be used as long as it has no adverse effect on the reactions. Examples of such solvent include DME, THF, dioxane, DMF, dimethylacetamide, toluene, benzene, methanol, ethanol, water and a mixture thereof. The present reaction suitably proceeds at 60 to 150° C., preferably 80 to 120° C., for generally from 1 to 24 hours.

(2) Compound [II-a] is reacted with Compound [XXIII-b] or Compound [XXIII-c] in the presence of a nickel catalyst or a copper catalyst in a solvent to give Compound [II-d] in which $Q^{1b}$ is an alkyl. Examples of the nickel catalyst include dichloro[1,1'-bis(diphenylphosphino)ferrocene]-nickel(II), bis(triphenylphosphine)nickel(II) chloride, 1,3-bis(diphenylphosphino)propane nickel chloride. Examples of the copper catalyst include cuprous bromide, cuprous chloride, cuprous cyanide, and the like. Any solvent may be used as long as it has no adverse effect on the reactions, and examples of such solvent include DME, THF, dioxane, toluene, benzene, and a mixture thereof. The present reaction generally proceeds at −78 to 150° C., suitably at 0 to 100° C., for generally from 1 to 24 hours.

Compound [II-a], Compound [II-b], Compound [II-c], or Compound [II-d] are reacted with Compound [III] in the same manner as in Method A to give the corresponding Compound [I].

As Compound [III], the known compound may be used directly, or, for example, it may be produced by the preparation process described in the following publications.
2(3H)-imidazolone: WO 03/35638
2-Oxo-3H-1,2,4-triazole: J. Heterocyclic Chem., 23(8), 881 (1986)
2-Oxodihydroxazole: JP 10-291982-A
3-Pyrazolone: Bioorg. Med. Chem. Lett., 1998, 8, 2689
2-Oxodihydropyridine: WO 99/32448
4-Oxodihydropyrimidine: WO 98/24780, WO 99/28303
Pyrrole: WO 97/05877, WO 97/05878, WO 97/16442
Imidazole: WO 00/63204
Pyrazole: WO 98/56377, WO 99/58523, WO 95/72571
Oxazole: WO 95/13067, WO 00/63204
Thiazole: JP 2001-114779-A, JP 2001-114690-A
1,2,4-triazole: WO 00/10563
Pyridine: WO 00/40243, WO 99/32448
Pyrazolo[1,5-a]pyridine: WO 02/16359
Pyrimidine: WO 97/33883
Pyridazine: Bioorg. Med. Chem. Lett., 2002, 12, 689
Pyrazine: WO 00/25791

EFFECTS OF THE INVENTION

Compound [I] of the present invention or a pharmaceutically acceptable salt thereof has an excellent p38 MAP kinase inhibitory activity, so that it is useful for prophylaxis or treatment of diseases related to the activation of p38 MAP kinase and the excess production of inflammatory mediators concerned with p38 MAP kinase such as TNF-α, IL-1, etc. Accordingly, Compound [I] of the present invention or a pharmaceutically acceptable salt thereof is useful for prophylaxis or treatment of diseases such as inflammatory diseases, etc., for example, arthritis (rheumatoid arthritis, osteoarthritis, infectious arthritis, gouty arthritis, traumatic arthritis, synovitis, periarthritis, etc.), inflammatory bowel diseases (ulcerative colitis, Crohn's disease, etc.), inflammatory dermal diseases [psoriasis, dermatitis (atopic dermatitis, contact dermatitis, urticaria, eczema, etc.), etc.], inflammatory respiratory diseases (asthma, bronchitis, pneumonia, pleurisy, pharyngitis, rhinitis, etc.), inflammatory eye diseases (conjunctivitis, keratitis, uveitis, etc.), nephritis, hepatitis, systemic inflammatory diseases (Behct's syndrome, systemic lupus erythematosus, etc.), shock (septic shock, endotoxin shock, etc.), cerebrovascular diseases (cerebral hemorrhage, cerebral infarction, cerebral edema, etc.), ischemic heart diseases (angina, cardiac infarction, congestive heart failure, etc.), osteoporosis, multiple sclerosis, diabetes, malignant tumor, cachexia, Alzheimer's disease, Parkinson's disease, acquired immunodeficiency syndrome, arteriosclerosis, disseminated intravascular coagulation syndrome, rejection by organ transplantation and graft versus host disease (GvHD), etc.

The preferred compound of the present invention or a pharmaceutically acceptable salt thereof shows superior p38 MAP kinase inhibitory activity and has a strong therapeutic effect on inflammatory diseases such as arthritis, and also shows superior pharmacokinetic profile (e.g. good stability of metabolism, low side-effects, weak inhibitory effect of cytochrome P450).

The compound of the present invention or a pharmaceutically acceptable salt thereof can be formulated into a pharmaceutical composition comprising a therapeutically effective amount of the compound and a pharmaceutically acceptable carrier. The pharmaceutically acceptable carrier is exemplified by a diluent, a binder (syrup, Gum Arabic, gelatin, sorbitol, tragacanth, polyvinylpyrrolidone), an excipient (lactose, sucrose, corn starch, potassium phosphate, sorbitol, glycine), a lubricant (magnesium stearate, talc, polyethylene glycol, silica), a disintegrator (potato starch) and a wetting agent (sodium lauryl-sulfate), and the like.

Compound [I] of the present invention or a pharmaceutically acceptable salt thereof can be administrated orally or parenterally, and can be used as a suitable medicinal preparation. Examples of a suitable medicinal preparation for oral administration include, for example, a solid preparation such as tablet, granule, capsule, powder, etc., or a liquid preparation, a suspension preparation or an emulsion preparation. Examples of a suitable medicinal preparation for parenteral administration include, for example, a sapository, an injection or an infusion preparation each of which using distilled water for injection, physiological saline or an aqueous glucose solution, or an inhalant, etc.

A dose of Compound [I] of the present invention or a pharmaceutically acceptable salt thereof may vary depending on an administration method, or an age, body weight or conditions of a patient, and generally preferably about 0.003 to 30 mg/kg per day, particularly preferably about 0.01 to 10 mg/kg per day.

EXAMPLES

In the following, the present invention is explained in more detail by referring to Examples and Reference examples, but the present invention is not limited by these.

The following abbreviations used in the present specification mean the following, respectively.

Me: methyl

Et: ethyl

THF: tetrahydrofuran

DMF: N,N-dimethylformamide

DMSO: dimethylsulfoxide

Bn: benzyl

Ns: 2-nitrobenzenesulfonyl

Example 1

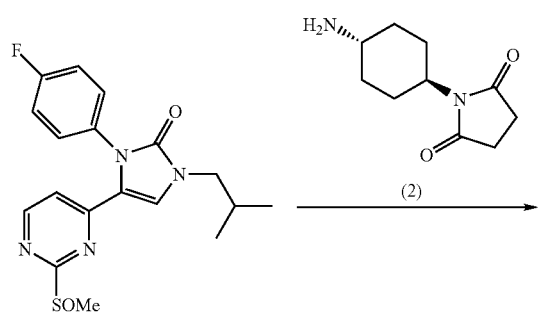

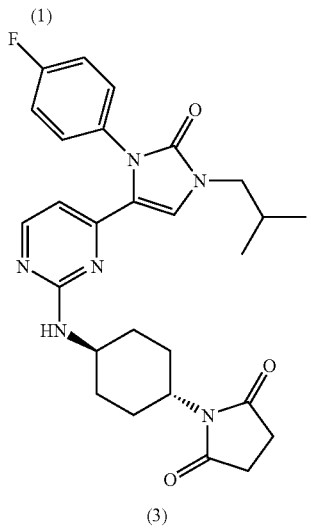

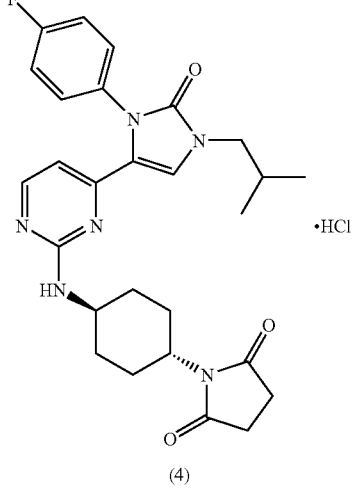

(1) A mixture comprising 112 mg of Compound (1) which can be prepared by the same method as described in WO 03/035638, 110 mg of Compound (2) and 3 ml of dioxane was stirred at 90° C. for 5 days. Water was added to the reaction mixture, and the mixture was extracted with ethyl acetate, and dried over anhydrous magnesium sulfate. After concentration under reduced pressure, the residue was purified by silica gel column chromatography (chloroform:methanol=19:1) to give 49 mg of Compound (3) as colorless crystals.

MS: 507 ([M+H]$^+$)

(2) To 47 mg of Compound (3) were added 2 ml of methanol and 26 μl of 4N hydrogen chloride-ethyl acetate solution; and the mixture was stirred at room temperature for 5 minutes. The reaction mixture was concentrated under reduced pressure, ethyl acetate was added to the mixture and powder was collected by filtration to give 47 mg of Compound (4).

MS: 507 ([M+H]$^+$)

Example 2

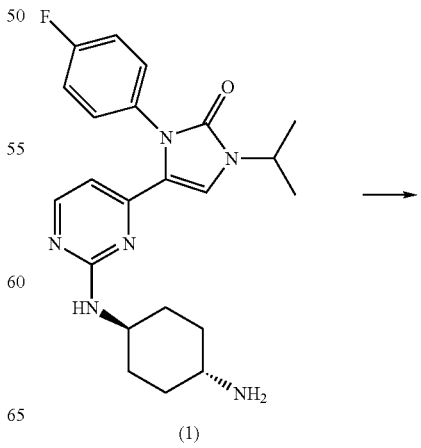

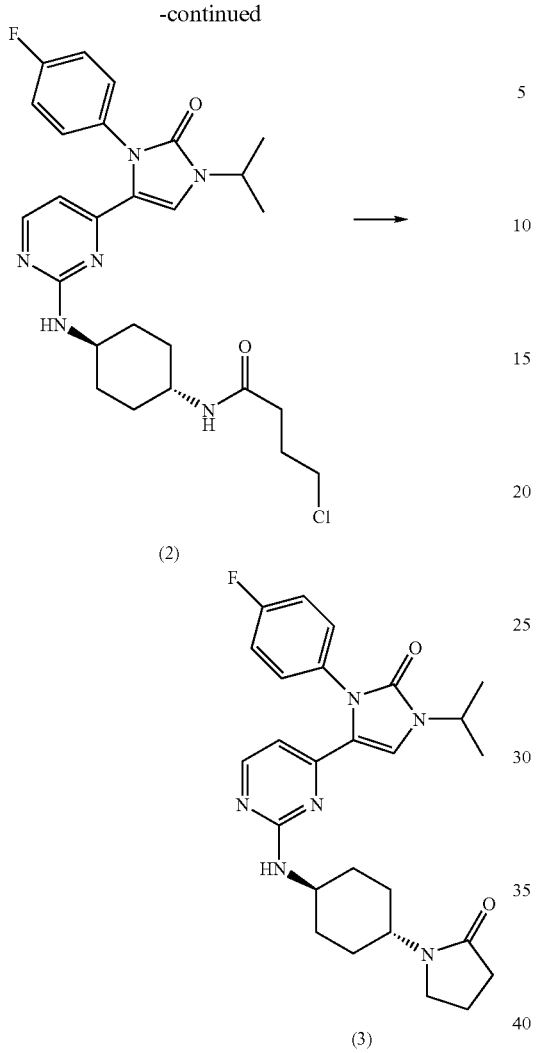

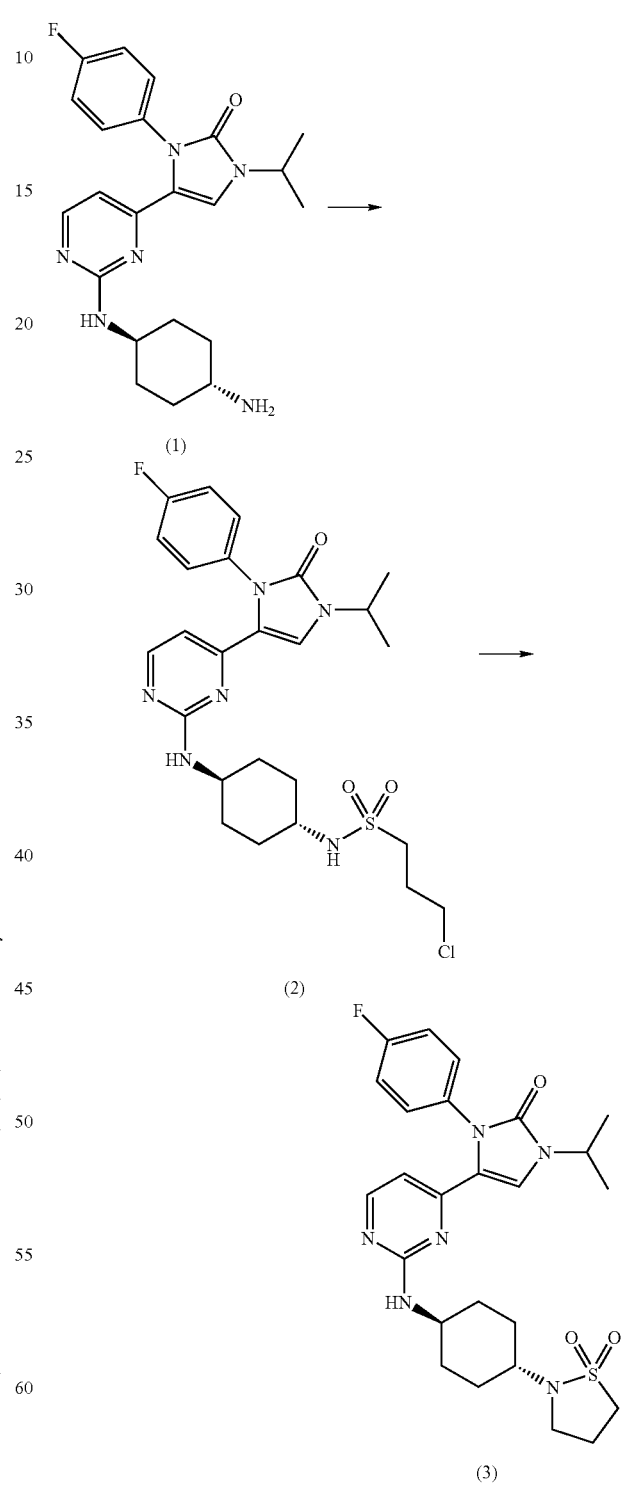

(1) To 10 ml of chloroform solution containing 500 mg of Compound (1) and 204 µl of triethylamine was added dropwise 172 mg of 4-chlorobutyryl chloride under ice-cooling, and the mixture was stirred under ice-cooling for an hour. The reaction mixture was washed successively with saturated aqueous sodium bicarbonate solution and saturated brine, and dried over anhydrous magnesium sulfate. After concentration under reduced pressure, the residue was crystallized from ethyl acetate to give 370 mg of Compound (2) as colorless crystals.

MS: 515 ([M+H]$^+$)

(2) In 10 ml of N,N-dimethylacetamide was dissolved 360 mg of Compound (2), and after adding 28.1 mg of sodium hydride (62.7% in oil) to the mixture, the resulting mixture was stirred at room temperature for an hour. Water was added to the reaction mixture and the resulting mixture was extracted with ethyl acetate. The extract was washed successively with water and saturated brine, and dried over anhydrous magnesium sulfate. After concentration under reduced pressure, the residue was purified by silica gel column chromatography (chloroform:methanol=19:1) to give 263 mg of Compound (3) as colorless crystals. MS: 479 ([M+H]$^+$)

(3) In the same manner as in Example 1(2), 253 mg of Compound (3) was treated to give 265 mg of hydrochloride of Compound (3). MS: 479 ([M+H]$^+$)

Example 3

(1) To 3 ml of chloroform solution containing 200 mg of Compound (1) and 102 µl of triethylamine was added dropwise 86.3 mg of 3-chloropropanesulfonyl chloride, and the mixture was stirred at room temperature for an hour. The reaction mixture was washed with water, and dried over anhydrous magnesium sulfate. After concentration under reduced pressure, the residue was crystallized from ethyl acetate to give 180 mg of Compound (2) as colorless crystals. MS: 551 ([M+H]⁺)

(2) In 20 ml of THF was dissolved 173 mg of Compound (2), 47.5 mg of potassium tert-butoxide was added to the solution, and the mixture was stirred at room temperature overnight. Water was added to the reaction mixture and the resulting mixture was extracted with ethyl acetate. The extract was washed successively with water and saturated brine, and dried over anhydrous magnesium sulfate. After concentration under reduced pressure, the residue was purified by silica gel column chromatography (chloroform:methanol=19:1) to give 77.9 mg of Compound (3) as colorless crystals. MS: 515 ([M+H]⁺)

(3) In the same manner as in Example 1(2), 75 mg of Compound (3) was treated to give 65 mg of hydrochloride of Compound (3). MS: 515 ([M+H]⁺)

Example 4

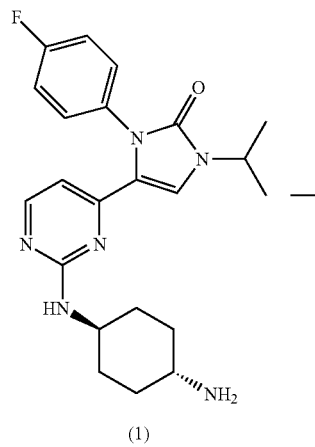
(1)

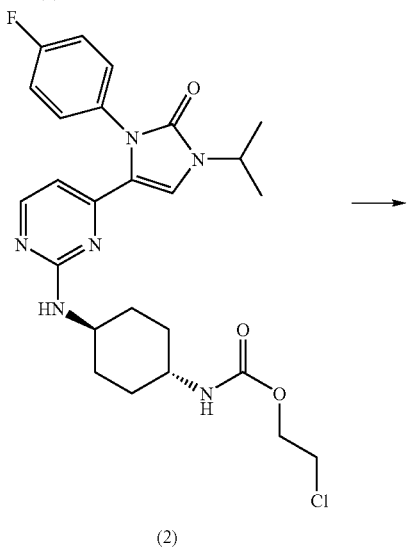
(2)

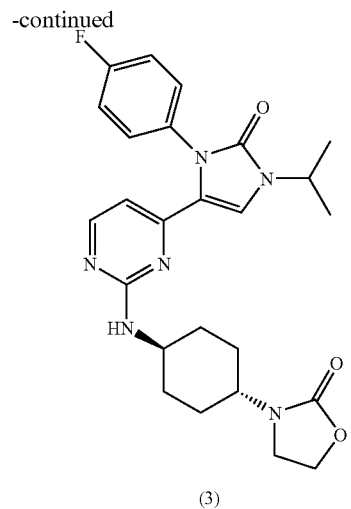
(3)

(1) To 3 ml of chloroform solution containing 150 mg of Compound (1) and 76.4 μl of triethylamine was added dropwise 52.2 mg of 2-chloroethyl chloroformate under ice-cooling, and the mixture was stirred under ice-cooling for 30 minutes. The mixture was washed with water, and dried over anhydrous magnesium sulfate. After concentration under reduced pressure, the residue was crystallized from ethyl acetate to give 130 mg of Compound (2) as colorless crystals. MS: 517 ([M+H]⁺)

(2) In 3 ml of THF was dissolved 125 mg of Compound (2), 47.5 mg of potassium tert-butoxide was added to the solution, and the mixture was stirred at room temperature overnight. Water was added to the reaction mixture and the resulting mixture was extracted with ethyl acetate. The extract was washed successively with water and saturated brine, and dried over anhydrous magnesium sulfate. After concentration under reduced pressure, the residue was purified by silica gel column chromatography (chloroform:methanol=19:1) to give 80.1 mg of Compound (3) as colorless crystals. MS: 481 ([M+H]⁺)

(3) In the same manner as in Example 1(2), 76 mg of Compound (3) was treated to give 64 mg of a hydrochloride of Compound (3). MS: 481 ([M+H]⁺)

Example 5

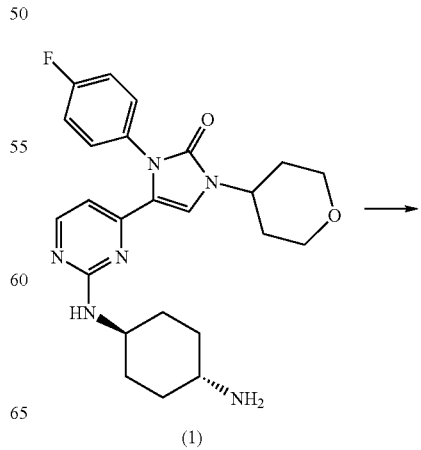
(1)

-continued

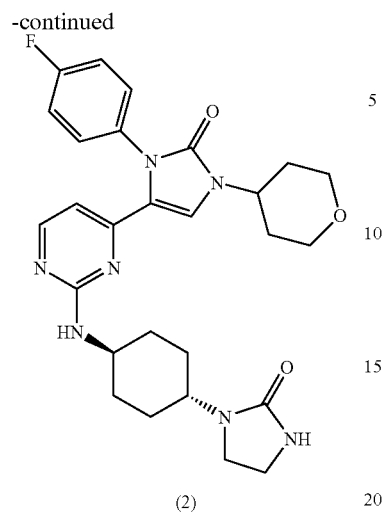

(2)

-continued

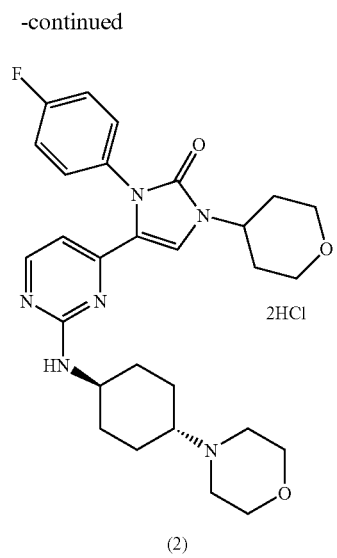

(2)

To 6.0 ml of dichloromethane solution containing 300 mg of Compound (1) which can be prepared by the same method as described in WO 03/035638, and 0.185 ml of triethylamine was added dropwise under ice-cooling 1.0 ml of dichloromethane solution containing 105 mg of 2-chloroethylisocyanate, and the mixture was stirred under ice-cooling for 15 minutes. Saturated aqueous sodium bicarbonate solution was added to the reaction mixture, and the mixture was extracted with chloroform. The extract was washed with saturated brine, and dried over anhydrous sodium sulfate. After concentration under reduced pressure, the obtained crude product was dissolved in 6.0 ml of DMF, 84 mg of sodium hydride (62.7% in oil) was added to the solution, and the resulting mixture was stirred at 60° C. for 20 hours. Saturated aqueous sodium bicarbonate solution was added to the reaction mixture, and the mixture was extracted with chloroform. The extract was washed with saturated aqueous sodium bicarbonate solution, and dried over anhydrous sodium sulfate. After concentration under reduced pressure, the residue was purified by NH silica gel column chromatography (ethyl acetate:methanol=24:1), and crystallized from chloroform-ethyl acetate to give 70.0 mg of Compound (2) as colorless crystals. MS: 522 ([M+H]$^+$)

Example 6

In a mixed solvent of 1.0 ml of THF and 0.25 ml of water were dissolved 136 mg of Compound (1), 47.2 mg of bis(2-chloroethyl)ether, 104 mg of potassium carbonate and 45 mg of sodium iodide, and the mixture was refluxed for 7 days. After cooling by allowing to stand, the reaction mixture was concentrated under reduced pressure. Water was added to the residue, the mixture was extracted with chloroform, and dried over anhydrous sodium sulfate. After concentration under reduced pressure, the residue was purified by silica gel column chromatography (chloroform:methanol=19:1), and then, treated by using hydrochloric acid in the same manner as in Example 1(2) to give 68.0 mg of Compound (2) as pale yellow crystals. MS: 523 ([M+H]$^+$)

Example 7

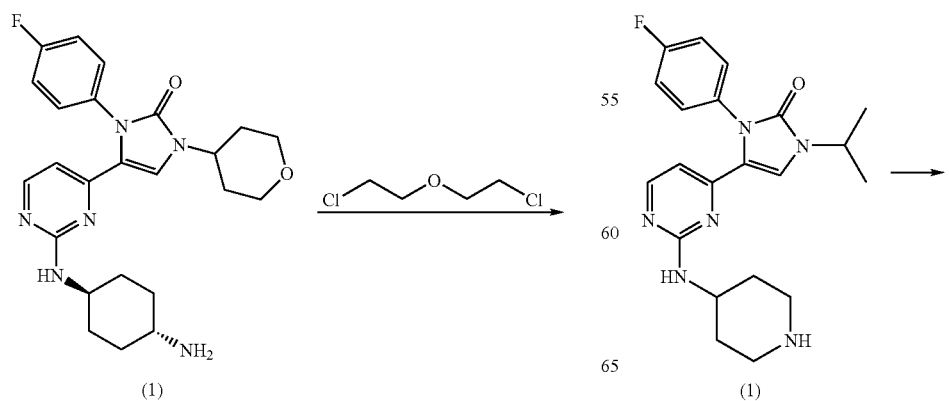

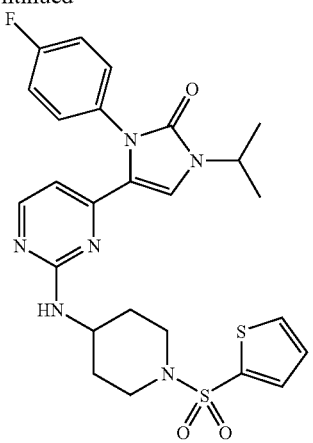

(2)

(1) To 3 ml of chloroform solution containing 100 mg of Compound (1) which can be prepared by the same method as described in WO 03/035638 and 52.7 μl of triethylamine was added dropwise 50.7 mg of thiophene 2-sulfonyl chloride, and the mixture was stirred at room temperature overnight. The mixture was washed with water, and dried over anhydrous magnesium sulfate. After concentration under reduced pressure, the residue was crystallized from ethyl acetate to give 110 mg of Compound (2) as colorless crystals.

(2) In the same manner as in Example 1(2), 107 mg of Compound (2) was treated to give 108 mg of a hydrochloride of Compound (2). MS: 543 ([M+H]$^+$)

Examples 8 to 54

In the same manner as mention in the above Examples, the following compounds were prepared.

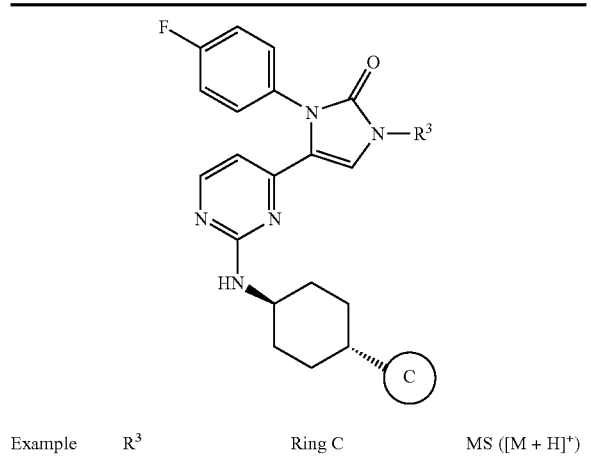

| Example | R$^3$ | Ring C | MS ([M + H]$^+$) |
|---|---|---|---|
| 8* | 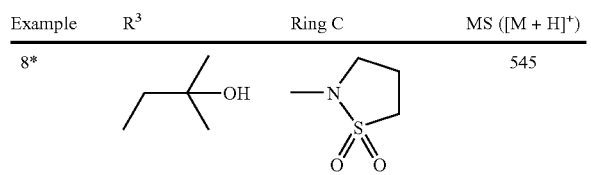 | | 545 |
| 9* | 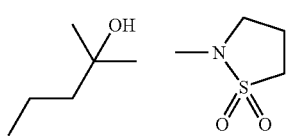 | | 559 |
| 10* | 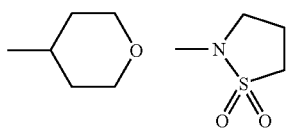 | | 557 |
| 11* | 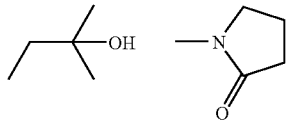 | | 509 |
| 12* | 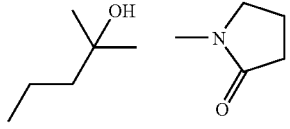 | | 523 |
| 13* | 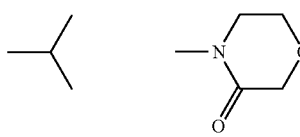 | | 495 |
| 14** | 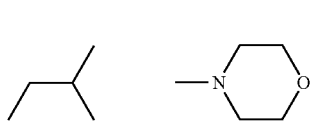 | | 495 |
| 15** | 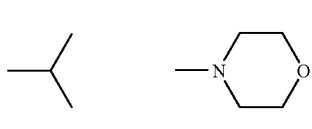 | | 481 |

-continued
| Example | R³ | Ring C | MS ([M + H]⁺) |
|---|---|---|---|
| 16* | 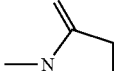 |  | 493 |
| 17* | 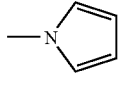 |  | 521 |
| 18* | 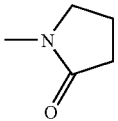 |  | 523 |
| 19** | 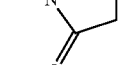 |  | 465 |
| 20** | 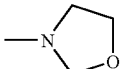 |  | 479 |
| 21* | 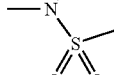 |  | 461 |
*monohydrochloride,
**dihydrochloride
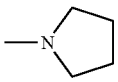
| Example | R³ | Ring C | MS ([M + H]⁺) |
|---|---|---|---|
| 22* |  | 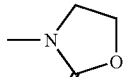 | 475 |
| 23* |  | 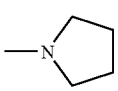 | 493 |
| 24* |  | 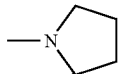 | 529 |
| 25* |  | 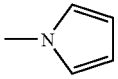 | 495 |
| 26* |  | 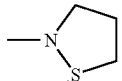 | 491 |
| 27* | | | 527 |
| 28* | | | 493 |
| 29* | | | 535 |

-continued

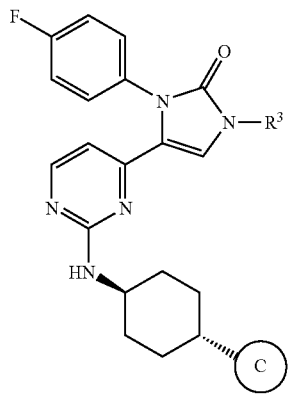

| Example | R³ | Ring C | MS ([M + H]⁺) |
|---|---|---|---|
| 30** | tetrahydropyran-4-yl | pyrrolidin-1-yl | 507 |
| 31** | cyclobutyl | pyrrolidin-1-yl | 477 |
| 32** | cyclobutyl | morpholin-4-yl | 493 |
| 33* | cyclobutyl | 2,5-dioxopyrrolidin-1-yl | 505 |

*monohydrochloride,
**dihydrochloride

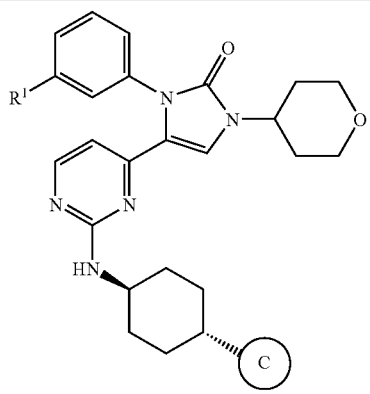

| Example | R¹ | Ring C | MS ([M + H]⁺) |
|---|---|---|---|
| 34* | Me | 1,1-dioxoisothiazolidin-2-yl | 553 |

-continued

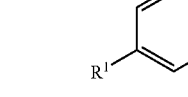

| Example | R¹ | Ring C | MS ([M + H]⁺) |
|---|---|---|---|
| 35* | Cl | 1,1-dioxoisothiazolidin-2-yl | 573 |
| 36* | Me | 2-oxooxazolidin-3-yl | 519 |
| 37* | Cl | 2-oxooxazolidin-3-yl | 539 |
| 38* | Me | 2-oxopyrrolidin-1-yl | 517 |
| 39* | Cl | 2-oxopyrrolidin-1-yl | 537 |
| 40** | Me | morpholin-4-yl | 519 |
| 41** | Cl | morpholin-4-yl | 539 |

*monohydrochloride,
**dihydrochloride

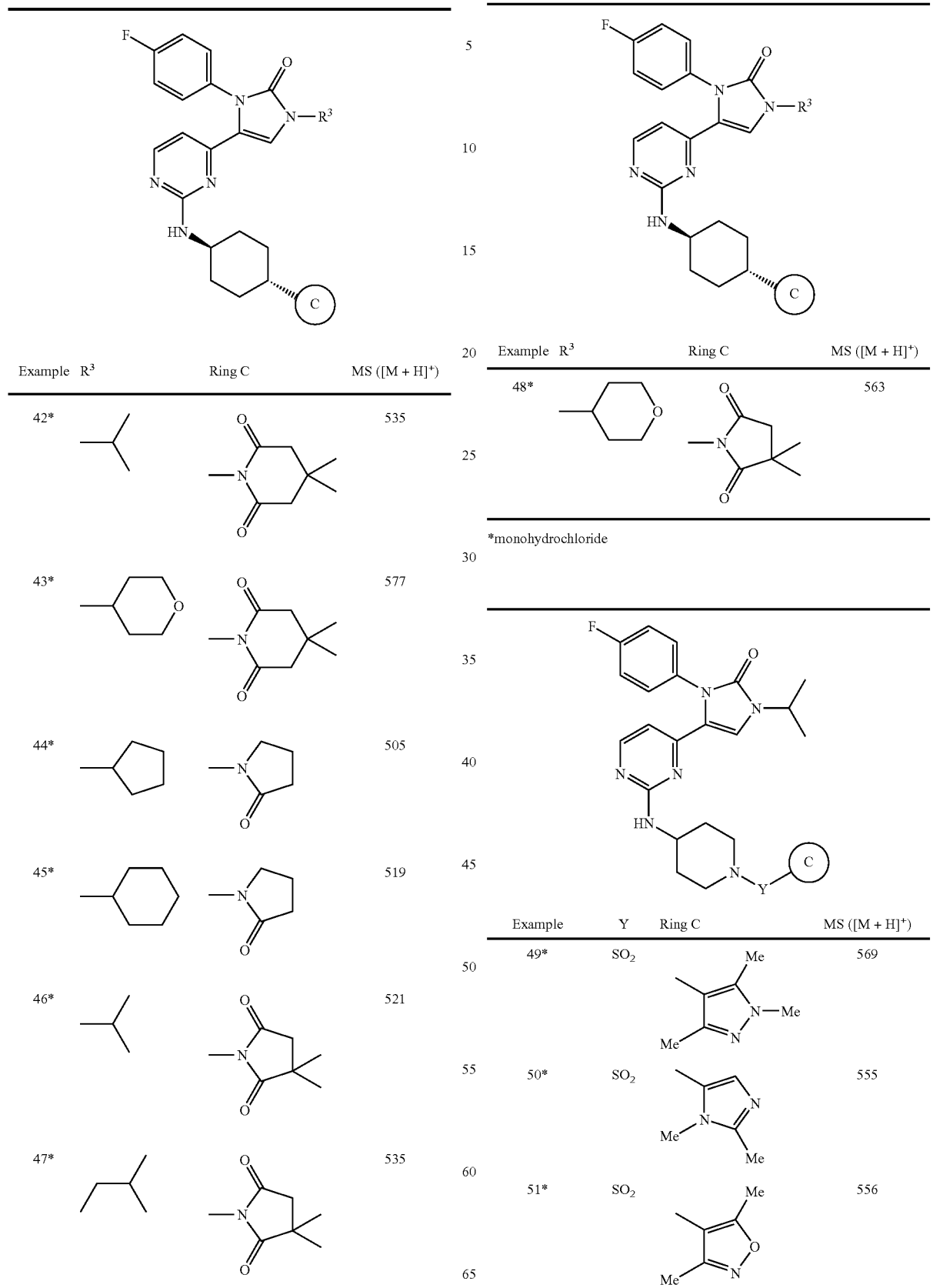

-continued

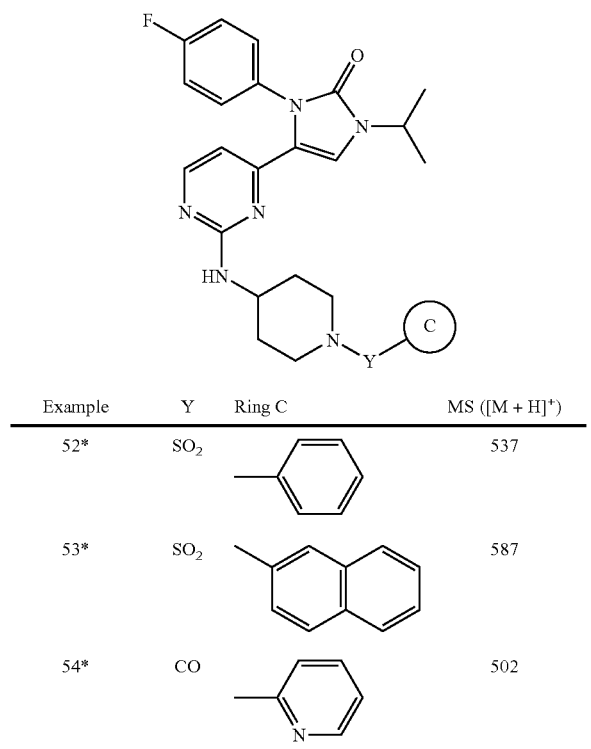

| Example | Y | Ring C | MS ([M + H]+) |
|---|---|---|---|
| 52* | SO₂ | (phenyl) | 537 |
| 53* | SO₂ | (naphthyl) | 587 |
| 54* | CO | (pyridyl) | 502 |

*monohydrochloride

Example 55

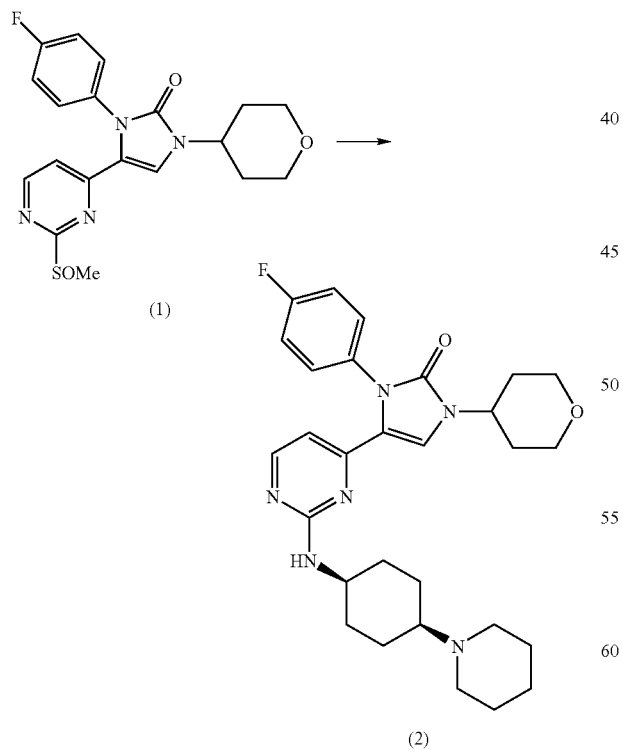

Compound (1) which can be prepared by the same method as described in WO 03/035638 and Compound (4) of Refer-ence example 1 were treated in the same manner as in Example 1 to give Compound (2).
MS: 521 ([M+H]+)

Example 56

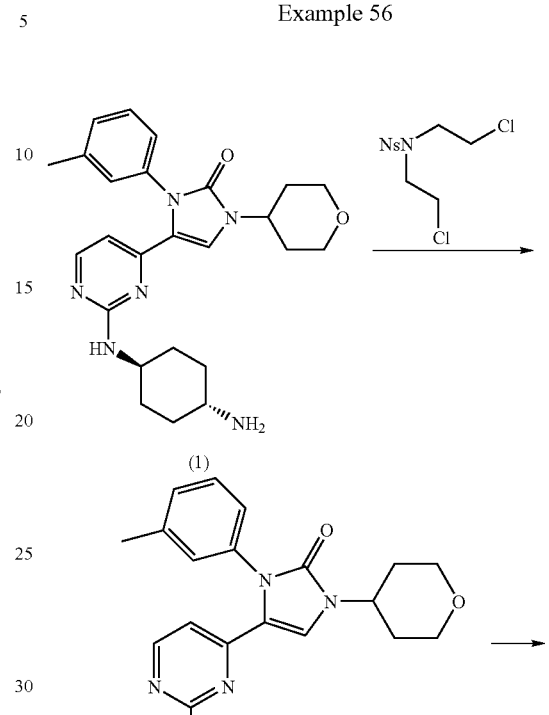

(1) In accordance with the method described in Tetrahedron Lett., 1995, 6373-74, etc., 1.1 g of Compound (1) (which can be prepared by the same method as described in WO 03/035638), 900 mg of N,N-bis-(2-chloroethyl)-2-nitro-benzenesulfonamide, 860 mg of potassium carbonate and 345 mg of sodium iodide were dissolved in a mixed solvent of 7.5 ml of ethanol and 1.9 ml of water, and the mixture was stirred under microwave irradiation at 150° C. for 75 minutes. After concentration under reduced pressure, water was added to the residue, the mixture was extracted with chloroform, and dried over anhydrous sodium sulfate. After concentration under reduced pressure, the residue was purified by silica gel column chromatography (chloroform:methanol=93:7) to give 578 mg of Compound (2) as pale yellow powder. MS: 703 ([M+H]+)

(2) In 3 ml of DMF were dissolved 550 mg of Compound (2), 216 mg of potassium carbonate and 97 mg of thiophenol, and the mixture was stirred at room temperature for an hour. Saturated aqueous sodium bicarbonate solution was added to the reaction mixture, and the resulting mixture was extracted with chloroform, and dried over anhydrous magnesium sulfate. After concentration under reduced pressure, the residue was purified by silica gel column chromatography (chloroform:methanol=93:7) to give 338 mg of Compound (3) as pale yellow powder. MS: 518 ([M+H]+)

Example 57

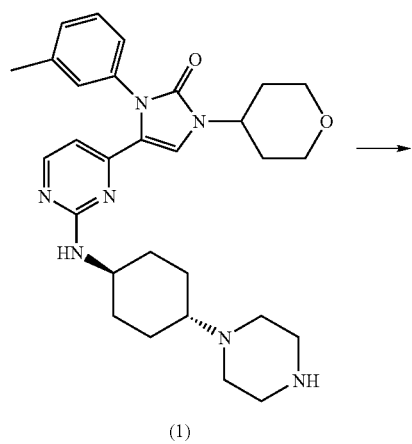

(1)

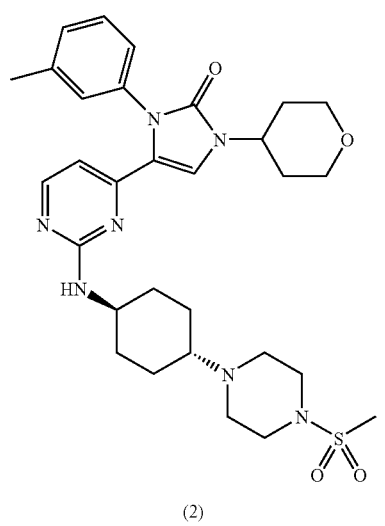

(2)

To 2 ml of dichloromethane solution obtaining 52 mg of Compound (1) was added dropwise 14 mg of methanesulfonyl chloride, and the mixture was stirred at room temperature for 15 minutes. Saturated aqueous sodium bicarbonate solution was added to the reaction mixture, and the resulting mixture was extracted with chloroform, and dried over anhydrous magnesium sulfate. After concentration under reduced pressure, the residue was crystallized from ethyl acetate-diisopropyl ether to give 57 mg of Compound (2) as pale yellow crystals. MS: 596 ([M+H]+)

Example 58

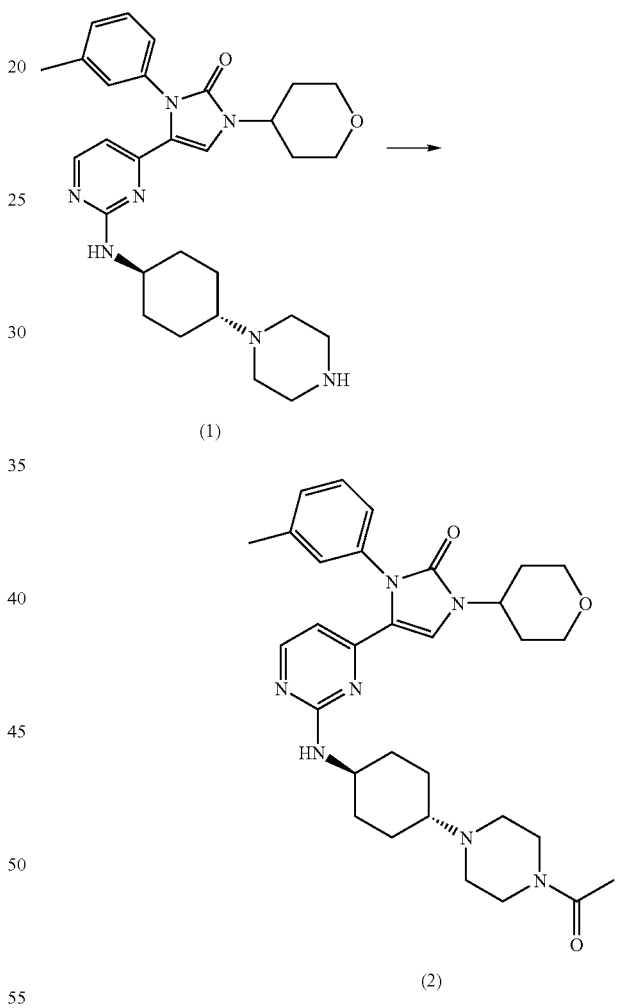

To 2 ml of dichloromethane solution containing 80 mg of Compound (1) was added dropwise 9.4 mg of acetyl chloride, and the mixture was stirred at room temperature for 15 minutes. Saturated aqueous sodium bicarbonate solution was added to the reaction mixture, the resulting mixture was extracted with chloroform, and dried over anhydrous magnesium sulfate. After concentration under reduced pressure, the residue was crystallized from ethyl acetate-diisopropyl ether to give 77 mg of Compound (2) as pale yellow crystals.

MS: 560 ([M+H]+)

Example 59

In 1 ml of methanol were dissolved 52 mg of Compound (1) and 11 mg of sodium cyanoborohydride, then, 10 mg of 1N aqueous hydrochloric acid and 13 mg of formalin were added dropwise to the solution, and the resulting mixture was stirred at room temperature for 40 minutes. After concentration under reduced pressure, aqueous ammonia was added to the residue, the mixture was extracted with chloroform, and dried over anhydrous magnesium sulfate. After concentration under reduced pressure, the residue was purified by silica gel column chromatography (chloroform:methanol=75:25) to give 35 mg of Compound (2) as pale yellow powder. MS: 532 ([M+H]$^+$)

Example 60

To 2 ml of DMF solution containing 52 mg of Compound (1) was added dropwise 19 mg of iodoethane, and the mixture was stirred at room temperature for 5 minutes. After concentration under reduced pressure, water was added to the residue, and the resulting mixture was extracted with chloroform and dried over anhydrous magnesium sulfate. After concentration under reduced pressure, the residue was purified by silica gel column chromatography (chloroform:methanol=97:3) to give 38 mg of Compound (2) as pale yellow powder.

MS: 546 ([M+H]$^+$)

Examples 61 to 83

In the same manner as in the above-mentioned Examples by using Compound (4) obtained in Reference example 1 and corresponding starting compounds, the following compounds were prepared.

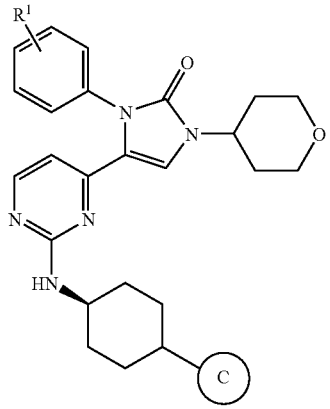
| Example | R¹ | Ring C | MS ([M + H]⁺) |
|---|---|---|---|
| 61 | 4-F | 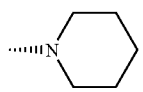 piperidine | 521 |
| 62* | 4-F | 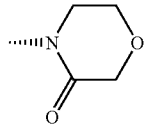 morpholinone | 537 |
| 63* | 3-Me | 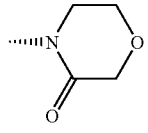 morpholinone | 533 |
| 64* | 3-Cl | 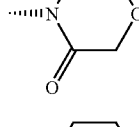 morpholinone | 553 |
| 65 | 4-F | 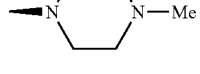 N-Me piperazine | 536 |
| 66 | 4-F | 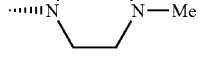 N-Me piperazine | 536 |
| 67 | 4-F | 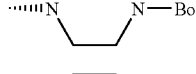 N-Boc piperazine | 622 |
| 68 | 4-F | 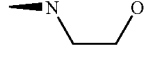 morpholine | 523 |
| 69 | 4-F | 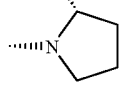 prolinol | 537 |
| 70 | 4-F | 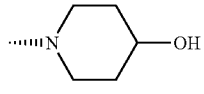 4-hydroxypiperidine | 537 |
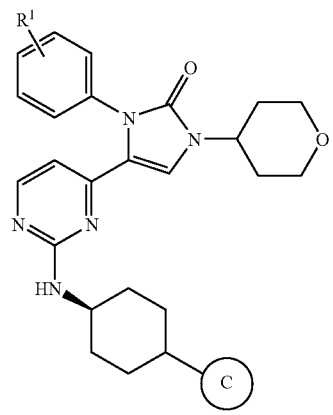
| Example | R¹ | Ring C | MS ([M + H]⁺) |
|---|---|---|---|
| 71 | 4-F | 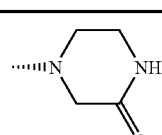 piperazinone | 536 |
| 72 | 4-F | 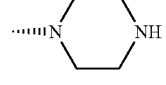 piperazine | 522 |
*monohydrochloride
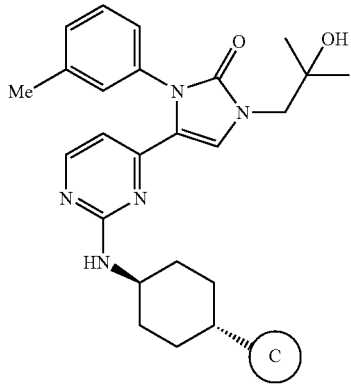
| Example | Ring C | MS ([M + H]⁺) |
|---|---|---|
| 73 | 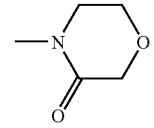 N-Me morpholinone | 521 |
| 74 | 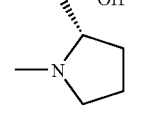 N-Me prolinol | 521 |
| 75 | 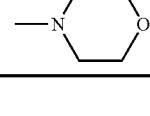 N-Me morpholine | 507 |

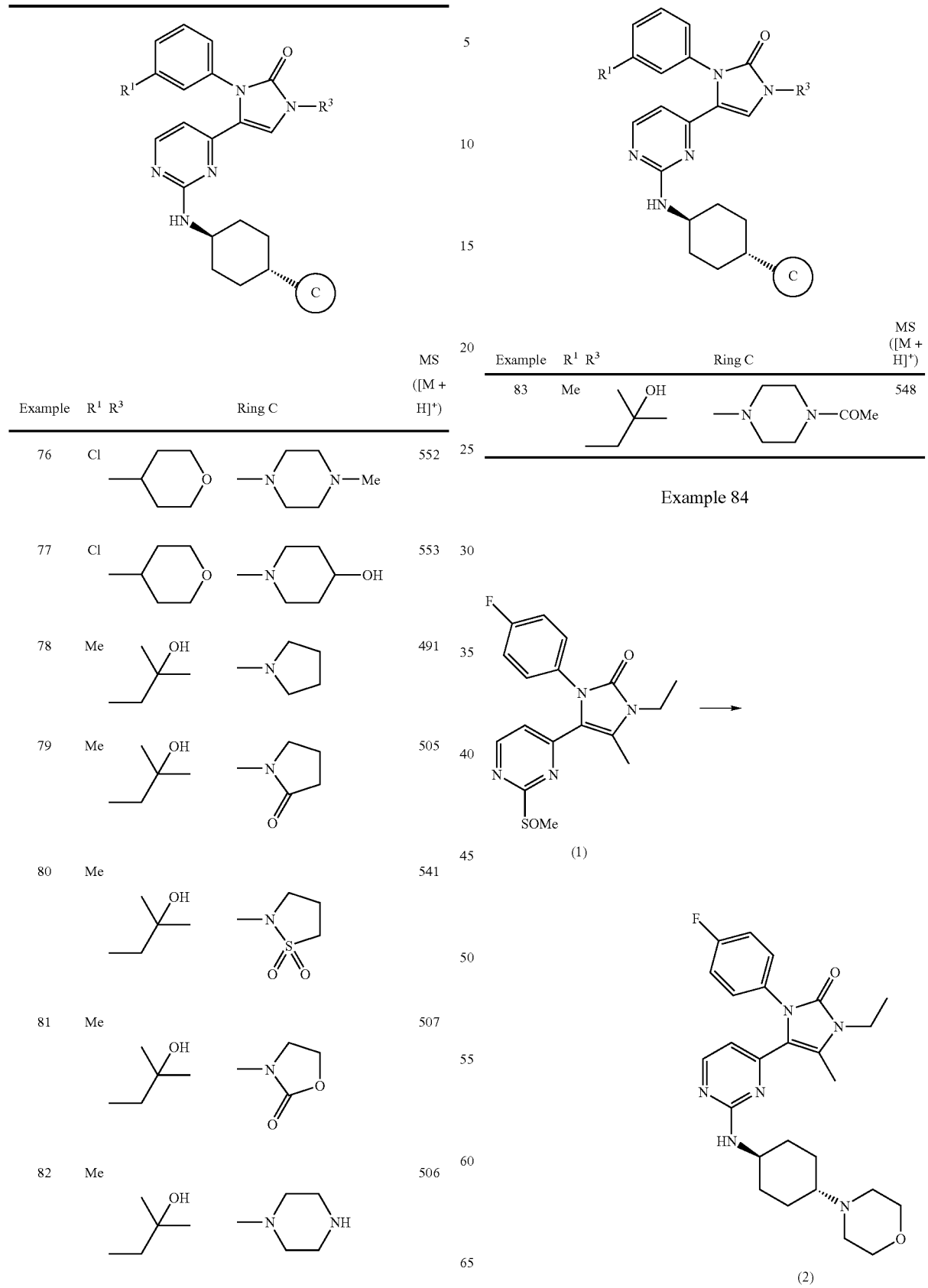

In 2.5 ml of 1,4-dioxane were dissolved 90 mg of Compound (1) which is prepared by reference example 4 and 64 mg of trans-4-morpholin-4-yl-cyclohexylamine, and the mixture was stirred at 90° C. for 144 hours. After cooling by allowing to stand, Saturated aqueous sodium bicarbonate solution was added to the reaction mixture, the resulting mixture was extracted with chloroform and dried over anhydrous magnesium-sulfate. After concentration under reduced pressure, the residue was purified by NH-silica gel column chromatography (hexane:ethyl acetate=50:50→0:100). After concentration under reduced pressure, the residue was crystallized from ethyl acetate to, give 44 mg of Compound (2) as pale yellowish crystals.

MS: 481 ([M+H]$^+$)

Example 85

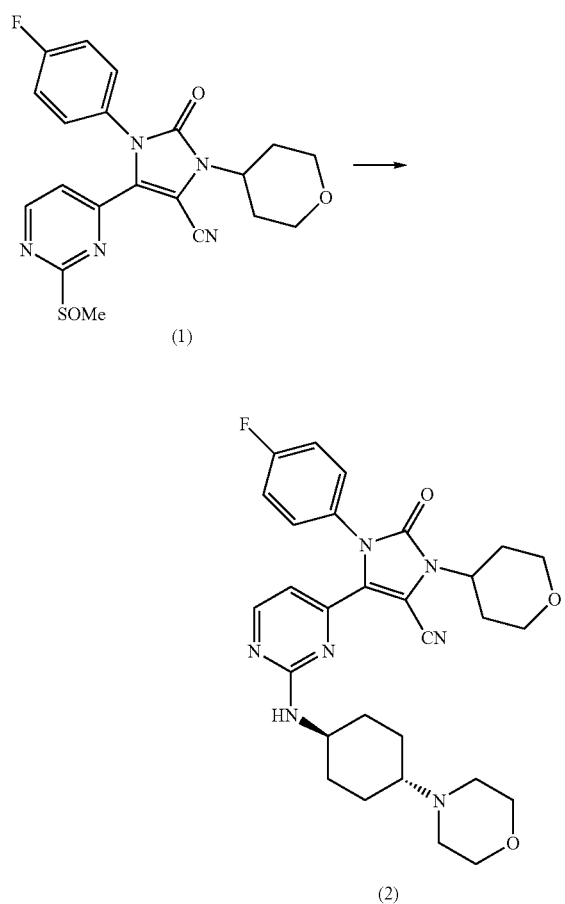

In the same manner as in example 84, 214 mg of Compound (1), which was prepared by reference example 5, was reacted and treated to give 172 mg of Compound (2) as colorless crystals.

MS: 548 ([M+H]$^+$)

Example 86

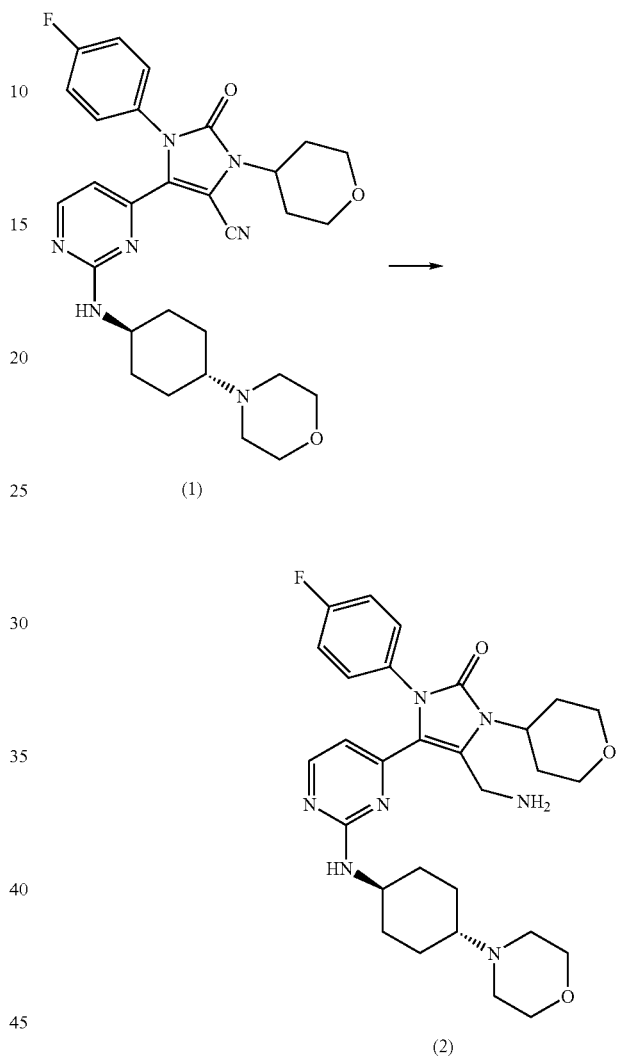

Raney-Ni was added to a solution of 141 mg of Compound (1) in 7N ammonia-methanol at room temperature, and the mixture was stirred at room temperature for 20 hours under hydrogen flow. After removing the catalyst, the filtrate was concentrated under reduced pressure. Chloroform was added to the residue and the mixture was dried over anhydrous sodium sulfate. After concentration under reduced pressure, the crude product was purified by NH silica gel column chromatography (chloroform:methanol=19:1) and crystallized from chloroform-ethyl acetate to give 80.0 mg of Compound (2) as colorless crystals.

MS: 552 ([M+H]$^+$)

Examples 87 to 136

The following compounds were prepared by carrying out a reaction and a treatment in the same manner as in the above-mentioned Examples.

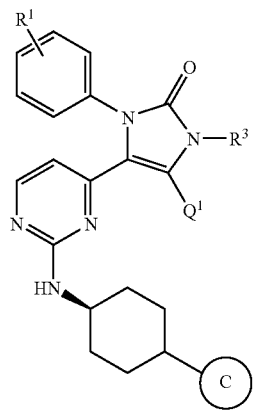

| Example | R¹ | Ring C | Q¹ | R³ | MS ([M + H]⁺) |
|---|---|---|---|---|---|
| 87 | 3-Me | ·····N⟨piperazine⟩N—Me | H | tetrahydropyran-4-yl | 532 |
| 88 | 4-F | ·····N⟨piperidine⟩OH | CN | tetrahydropyran-4-yl | 562 |
| 89 | 4-F | ·····N⟨pyrrolidine⟩CH₂OH | CN | tetrahydropyran-4-yl | 562 |
| 90 | 4-F | ·····N⟨morpholinone⟩ | CN | tetrahydropyran-4-yl | 562 |
| 91 | 4-F | ·····N⟨morpholinone⟩ | CH₂NH₂ | tetrahydropyran-4-yl | 566 |
| 92 | 3-Me | ·····N⟨morpholine⟩ | CN | Et | 488 |
| 93 | 3-Me | ·····N⟨morpholinone⟩ | CN | Et | 502 |
| 94 | 3-Me | ·····N⟨piperidine⟩OH | H | tetrahydropyran-4-yl | 533 |
| 95 | 4-F | ·····N⟨piperazinone⟩N—Me | H | tetrahydropyran-4-yl | 550 |

-continued
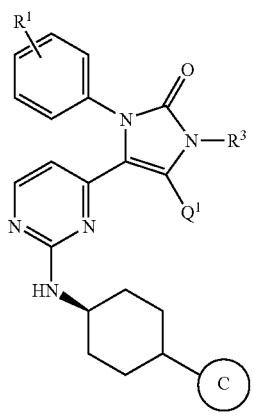
| Example | R¹ | Ring C | Q¹ | R³ | MS ([M + H]⁺) |
|---|---|---|---|---|---|
| 96 | 4-F | (azepane-N) | H | (tetrahydropyran-4-yl) | 535 |
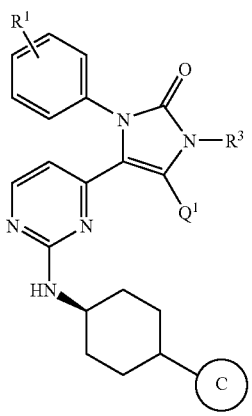
| Example | R¹ | Ring C | Q¹ | R³ | MS ([M + H]⁺) |
|---|---|---|---|---|---|
| 97 | 3-Cl | (piperidine-N) | H | (tetrahydropyran-4-yl) | 537 |
| 98 | 3-Me | (2-hydroxymethylpyrrolidine-N) | H | (tetrahydropyran-4-yl) | 533 |
| 99 | 3-Me | (piperidine-N) | H | (tetrahydropyran-4-yl) | 517 |
| 100 | 4-F | (4-acetylpiperazine-N) | Me | (tetrahydropyran-4-yl) | 564 |

-continued

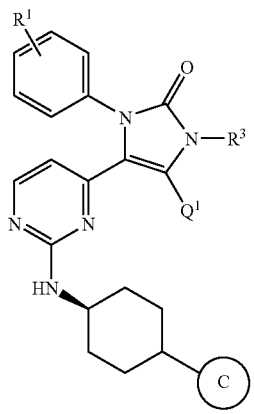

| Example | R¹ | Ring C | Q¹ | R³ | MS ([M + H]⁺) |
|---|---|---|---|---|---|
| 101 | 4-F | piperazine-N-SO₂Me | Me | tetrahydropyran | 600 |
| 102 | 4-F | piperazine-N-COOMe | Me | tetrahydropyran | 580 |
| 103 | 4-F | isothiazolidine 1,1-dioxide | Me | tetrahydropyran | 571 |
| 104 | 4-F | 3-oxomorpholine | Me | Et | 495 |
| 105 | 4-F | 4-hydroxypiperidine | Me | Et | 495 |
| 106 | 4-F | 2-(hydroxymethyl)pyrrolidine | Me | Et | 495 |
| 107 | 3-Me | 3-oxomorpholine | Me | tetrahydropyran | 547 |
| 108 | 3-Me | morpholine | Me | tetrahydropyran | 533 |
| 109 | 3-Me | isothiazolidine 1,1-dioxide | Me | tetrahydropyran | 567 |

| Example | Q¹ | Ring C | MS ([M + H]⁺) |
|---|---|---|---|
| 110 | Me | (4-methyl-3-oxomorpholine) | 505 |
| 111 | Me | (1,4-dimethyl-2-oxopiperazine) | 518 |
| 112 | Me | (1,4-dimethylpiperazine) | 504 |
| 113 | Me | (1-methylpiperidine) | 489 |
| 114 | Me | ((1-methylpyrrolidin-2-yl)methanol) | 505 |

| Example | R¹ | R³ | Q¹ | Ring C | MS ([M + H]⁺) |
|---|---|---|---|---|---|
| 115 | 4-F | 4-methyltetrahydropyran | Me | 4-methyl-3-oxomorpholine | 551 |

-continued

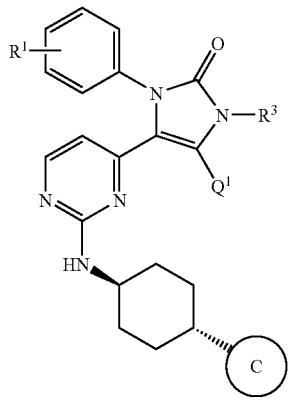

| Example | R¹ | R³ | Q¹ | Ring C | MS ([M + H]⁺) |
|---|---|---|---|---|---|
| 116 | 4-F | tetrahydropyran-4-yl | Me | piperidin-1-yl | 535 |
| 117 | 3-Me | tetrahydropyran-4-yl | Me | piperazin-1-yl | 532 |
| 118 | 3-Me | tetrahydropyran-4-yl | Me | 4-methylpiperazin-1-yl | 546 |
| 119 | 3-Me | tetrahydropyran-4-yl | Me | (2S)-2-(hydroxymethyl)pyrrolidin-1-yl | 547 |
| 120 | 3-Me | tetrahydropyran-4-yl | Me | 4-hydroxypiperidin-1-yl | 547 |
| 121 | 3-Me | tetrahydropyran-4-yl | Me | 3-oxopiperazin-1-yl | 546 |
| 122 | 3-Me | isobutyl | Me | 1,1-dioxoisothiazolidin-2-yl | 525 |
| 123 | 3-Me | isobutyl | Me | morpholin-4-yl | 491 |
| 124 | 4-F | tetrahydropyran-4-yl | Me | morpholin-4-yl | 537 |
| 125 | 3-Me | tetrahydropyran-4-yl | Me | 4-acetylpiperazin-1-yl | 574 |

-continued
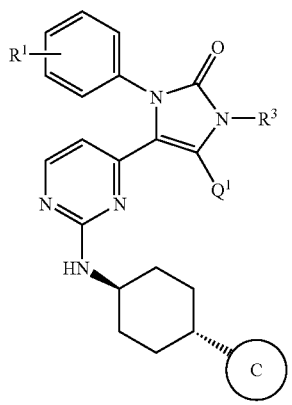
| Example | R¹ | R³ | Q¹ | Ring C | MS ([M + H]⁺) |
|---|---|---|---|---|---|
| 126 | 3-Me | 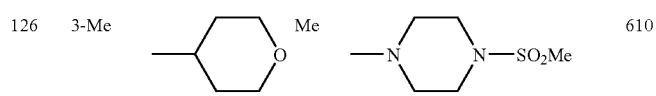 | Me | | 610 |
| 127 | 3-Me | 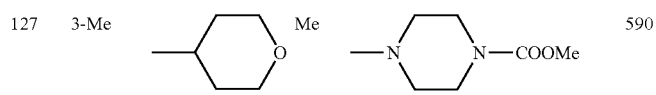 | Me | | 590 |
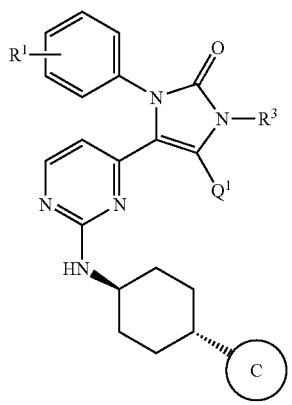
| Example | R¹ | R³ | Q¹ | Ring C | MS ([M + H]⁺) |
|---|---|---|---|---|---|
| 128 | 4-F | 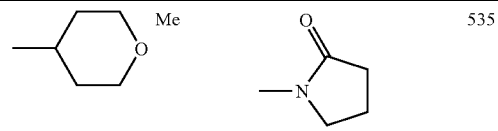 | Me | | 535 |
| 129 | 4-F | 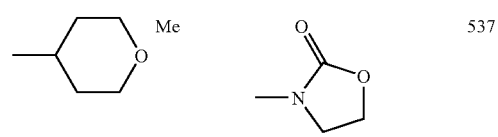 | Me | | 537 |

-continued
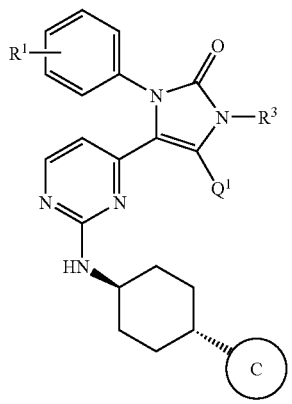
| Example | R¹ | R³ | Q¹ | Ring C | MS ([M + H]⁺) |
|---|---|---|---|---|---|
| 130 | 3-Me | isobutyl | Me | N-methyl-2-pyrrolidinone | 489 |
| 131 | 3-Me | isobutyl | Me | N-methyl-2-oxazolidinone | 491 |
| 132 | 3-Me | tetrahydropyran-4-yl | Me | piperidin-1-yl | 531 |
| 133 | 3-Me | 2-hydroxy-2-methylbutyl | Me | 3-oxomorpholin-4-yl | 535 |
| 134 | 4-F | tetrahydropyran-4-yl | Me | 1,4-dimethyl-2-oxopiperazin-4-yl | 564 |
| 135 | 4-F | tetrahydropyran-4-yl | Me | 4-methylpiperazin-1-yl | 550 |
| 136 | 4-F | tetrahydropyran-4-yl | H | 2-oxopiperidin-1-yl | 535 |

The following compounds are prepared by carrying out a reaction and a treatment in the same manner as in the above-mentioned Examples.
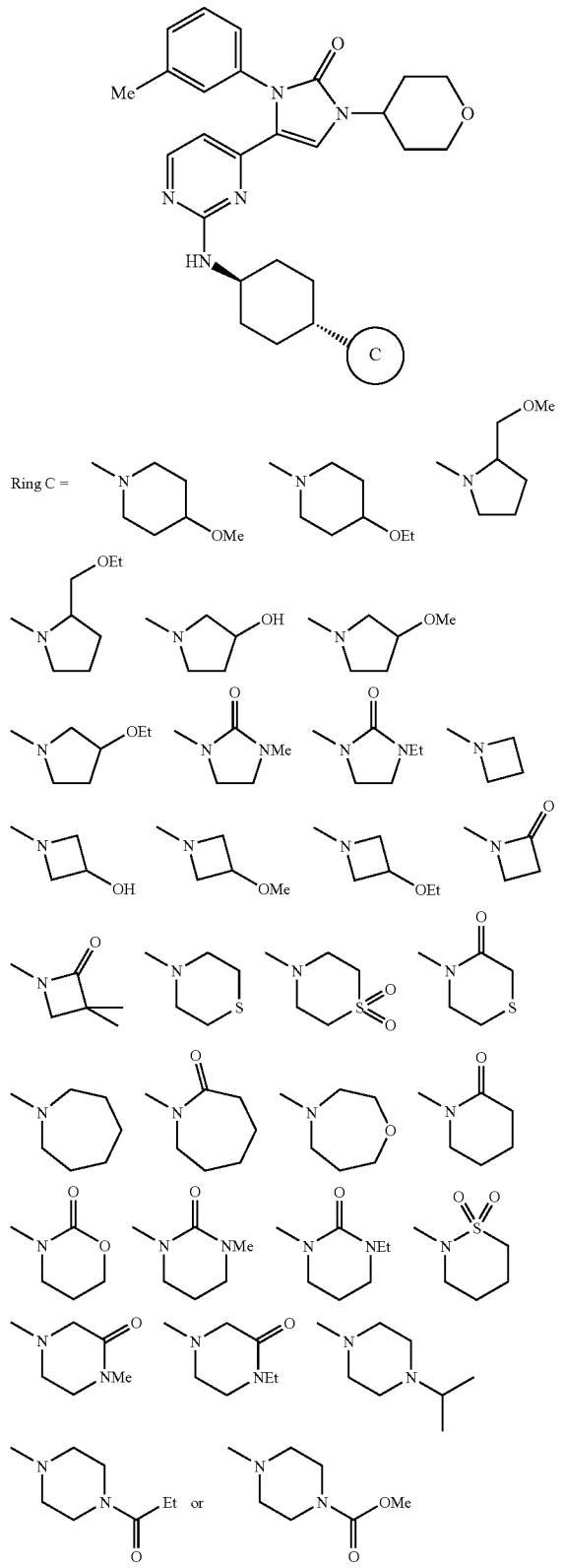
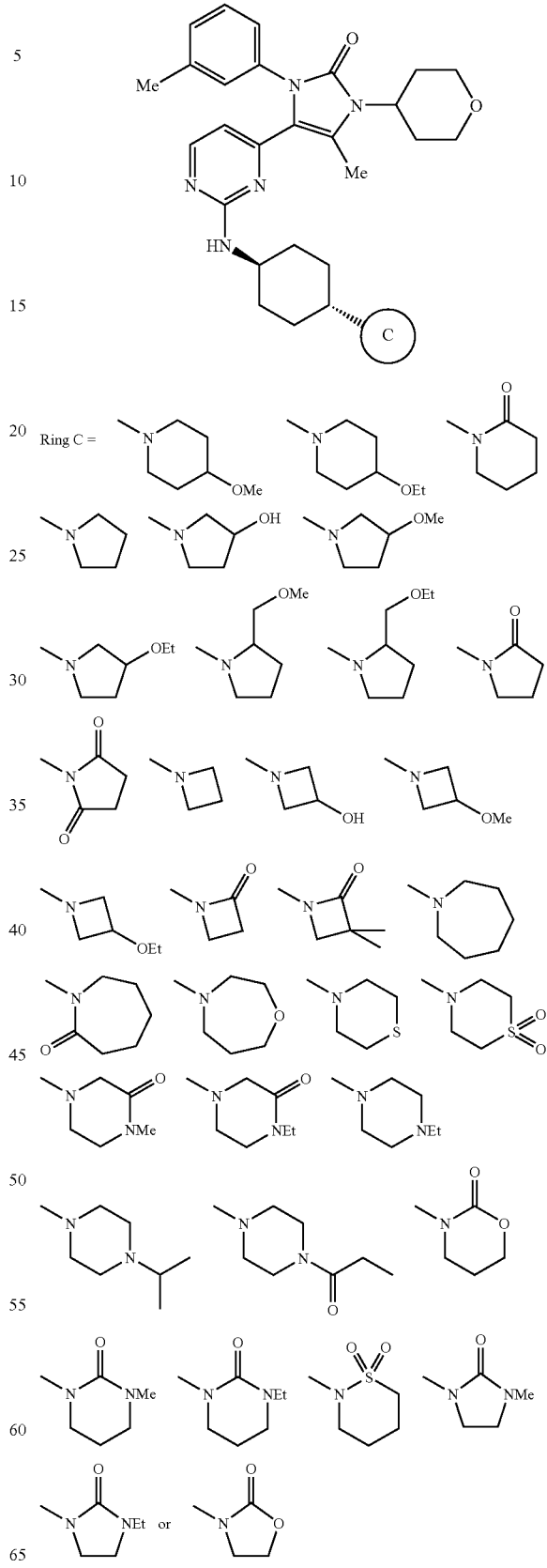

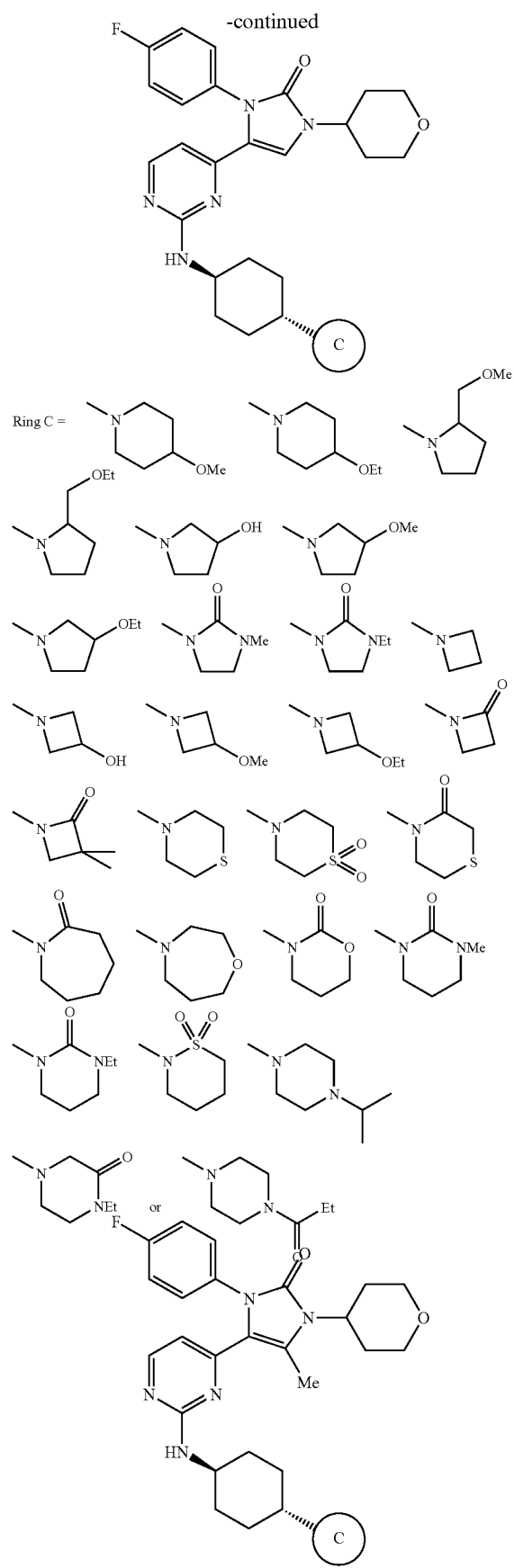
The following compound (I-1) to compound (I-69) are prepared by carrying out a reaction and a treatment in the same manner as in the above-mentioned Examples.

-continued
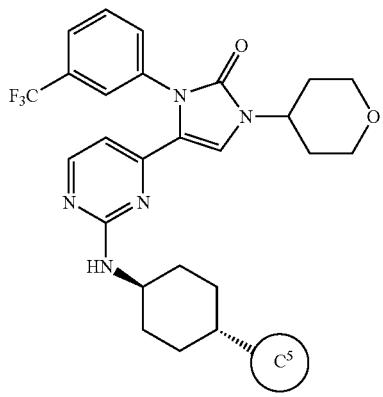 (I-1)
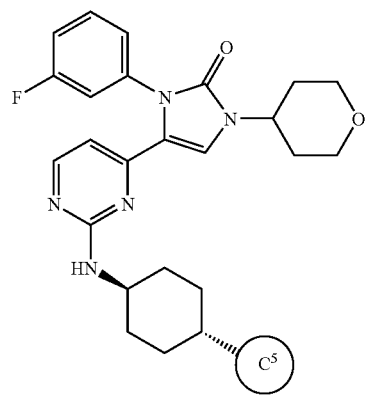 (I-2)
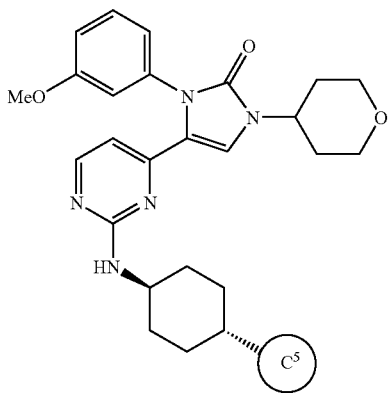 (I-3)
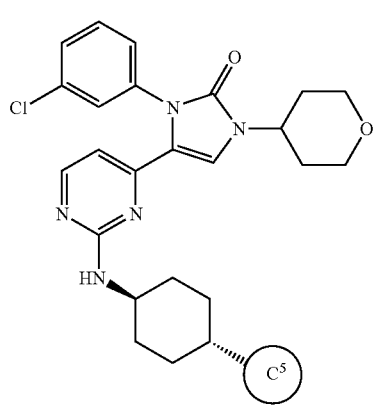 (I-4)
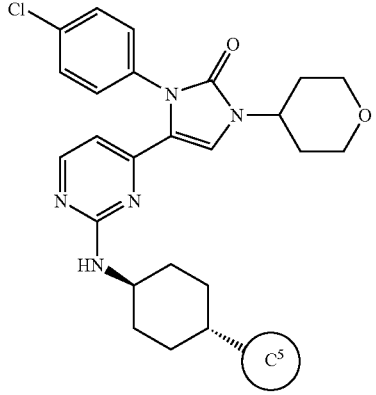 (I-5)
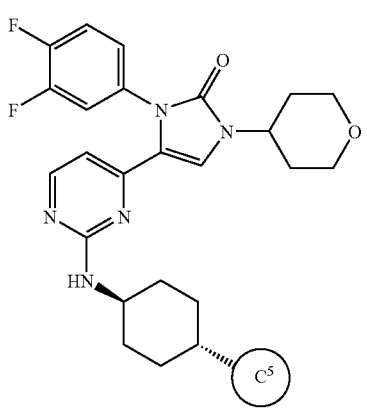 (I-6)
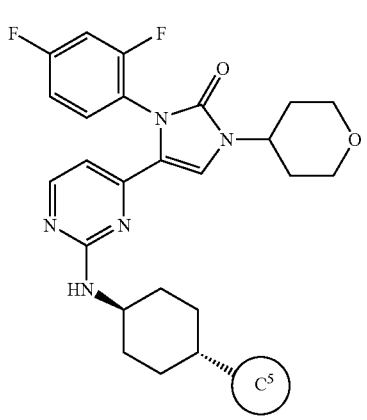 (I-7)
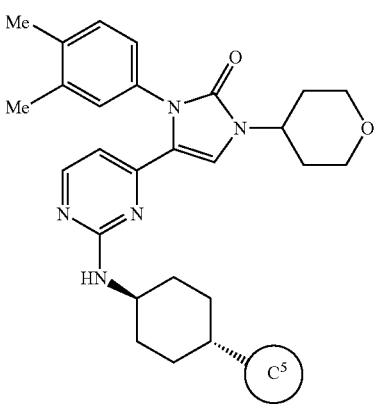 (I-8)

-continued
(I-9) 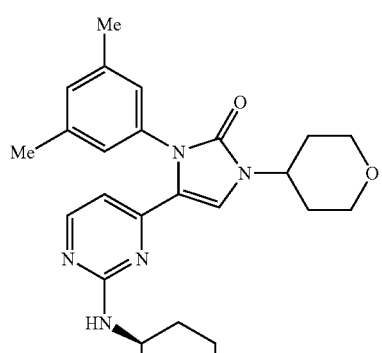
(I-10) 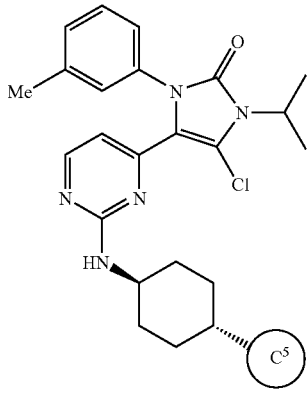
(I-11) 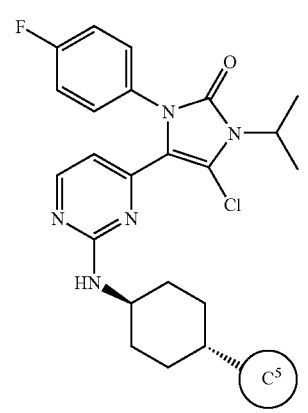
(I-12) 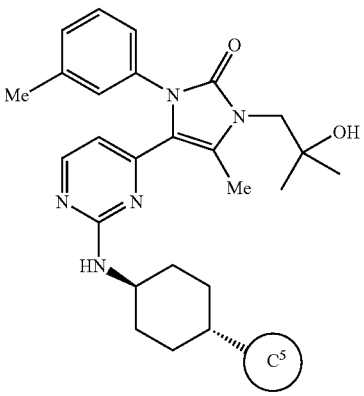
-continued
(I-13) 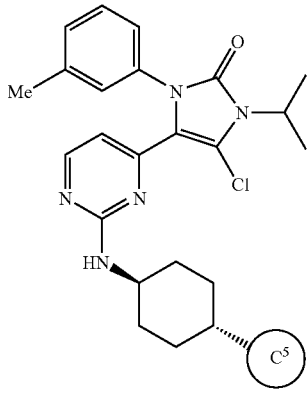
(I-14) 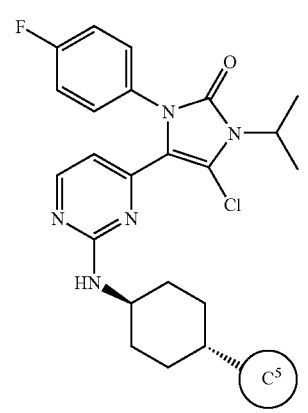
(I-15) 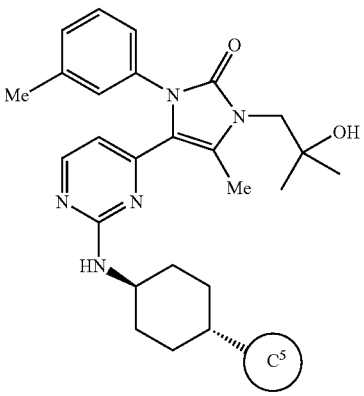
(I-16) 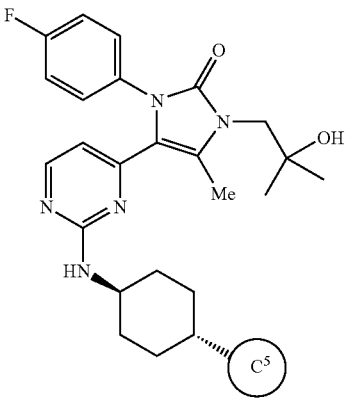

-continued
(I-17)
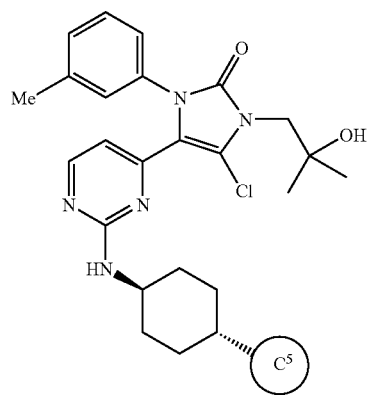
(I-18)
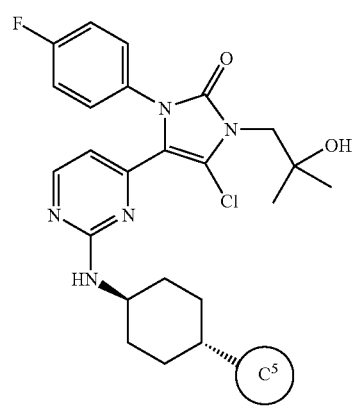
(I-19)
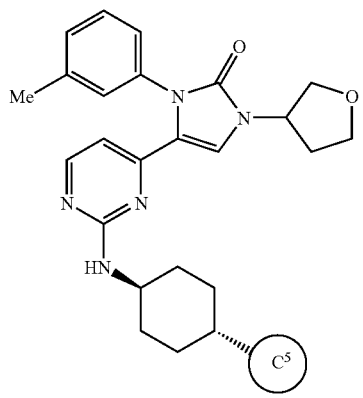
(I-20)
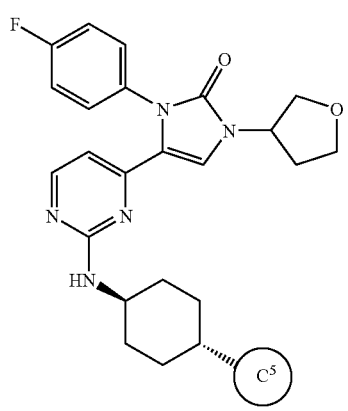
-continued
(I-21)
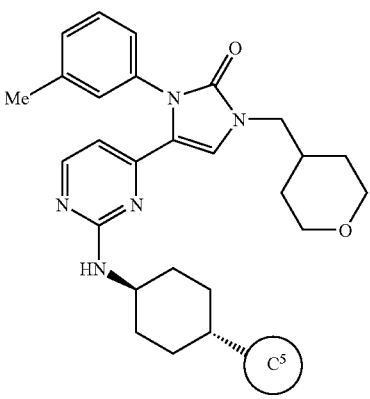
(I-22)
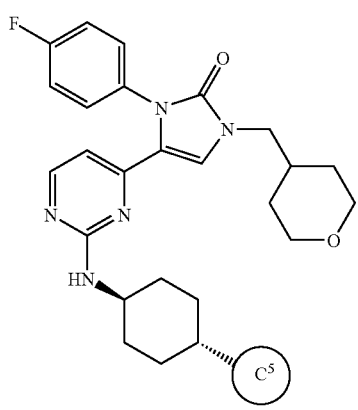
(I-23)
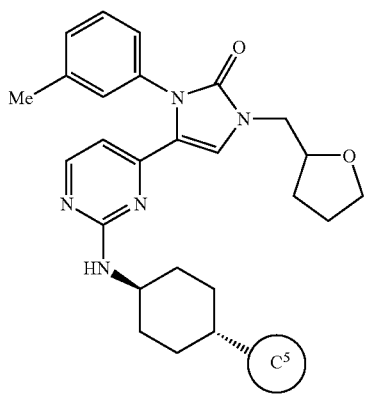
(I-24)
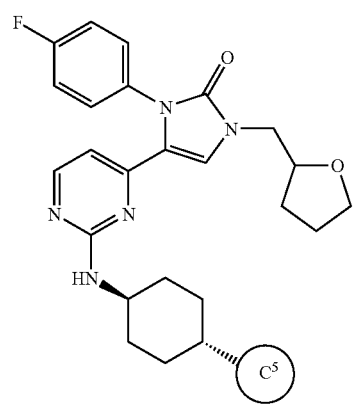

-continued
(I-25)
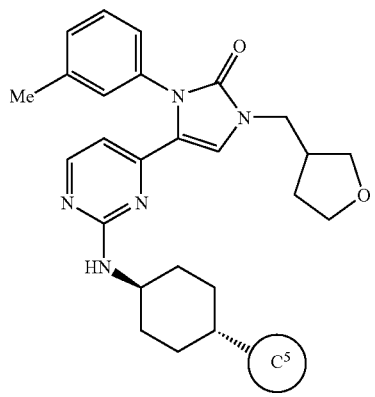
(I-26)
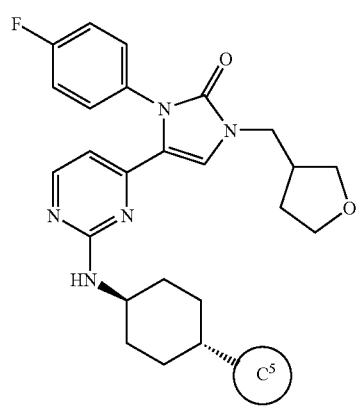
(I-27)
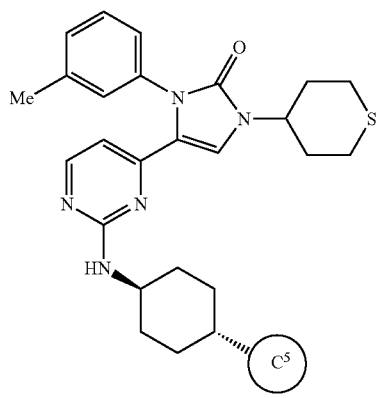
(I-28)
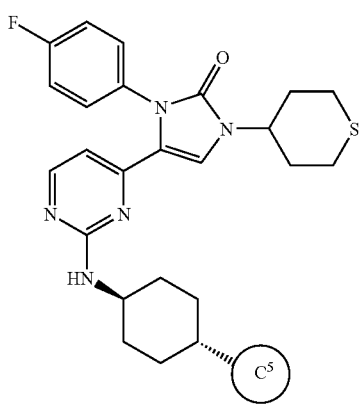
-continued
(I-29)
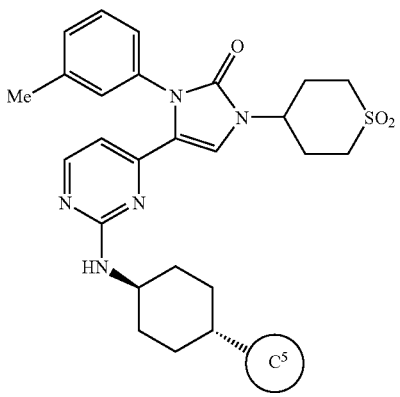
(I-30)
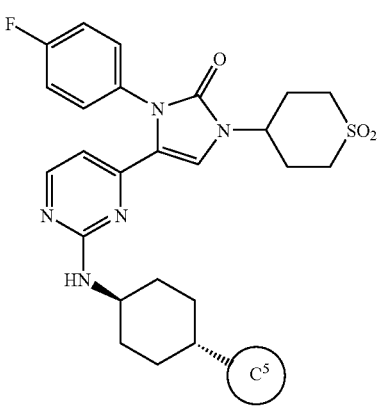
(I-31)
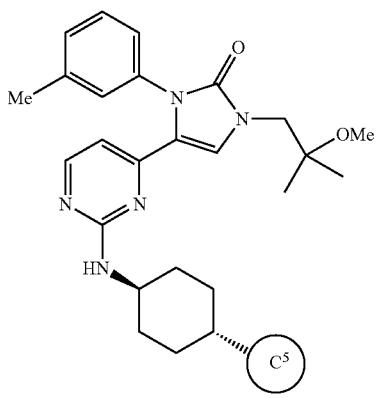
(I-32)
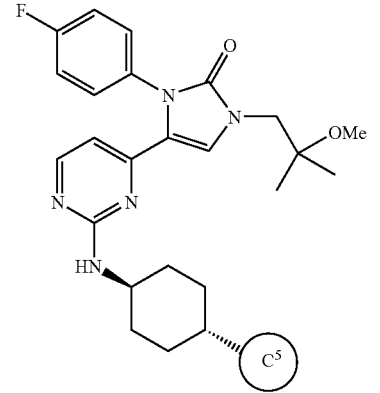

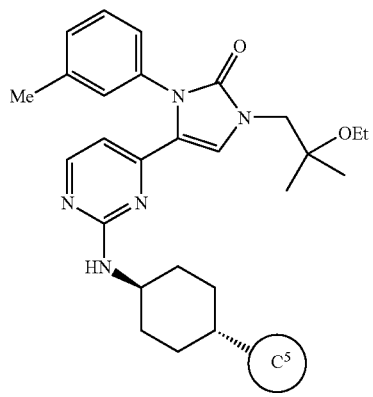 (I-33)
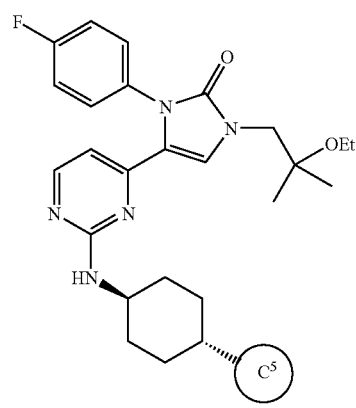 (I-34)
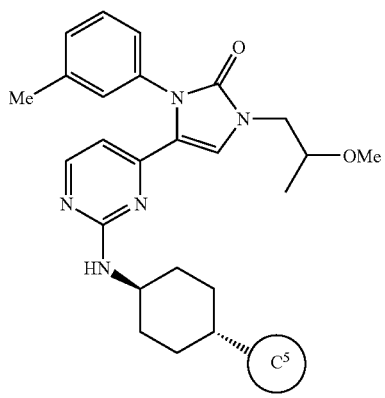 (I-35)
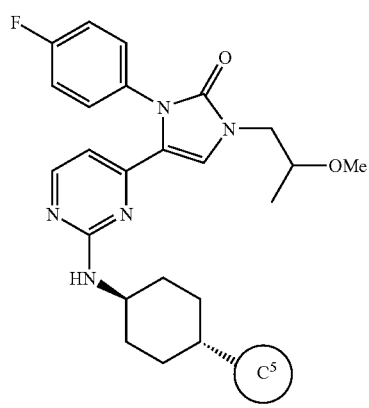 (I-36)
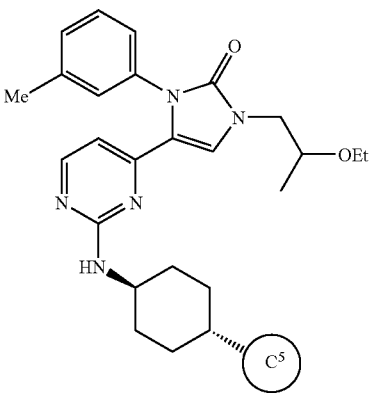 (I-37)
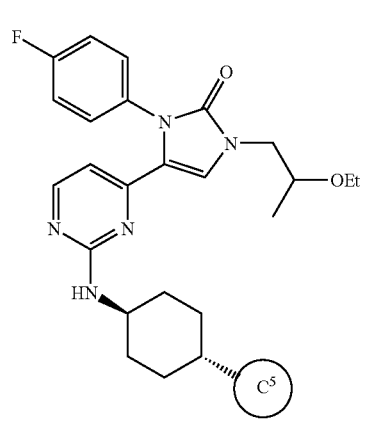 (I-38)
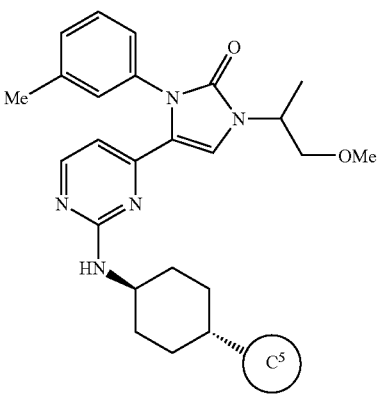 (I-39)
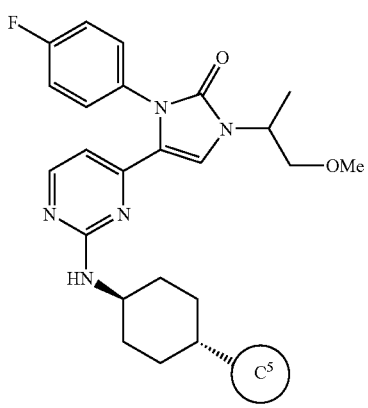 (I-40)

-continued
(I-41)
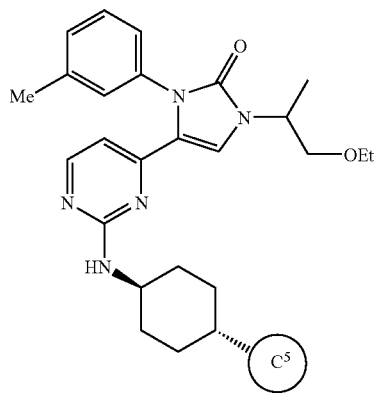
(I-42)
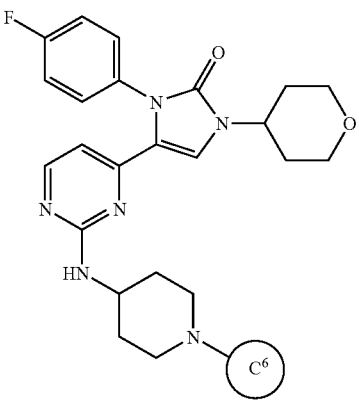
(I-43)
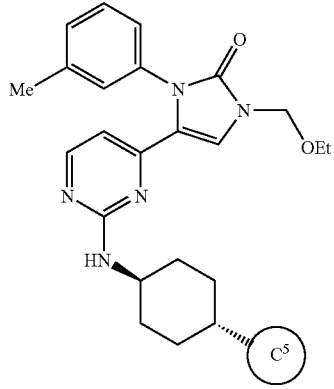
(I-44)
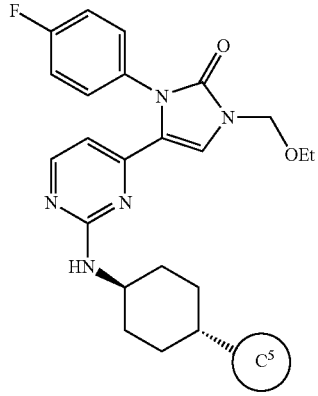
-continued
(I-45)
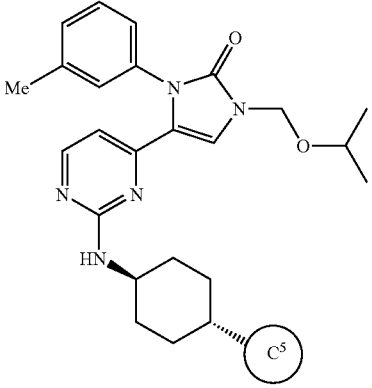
(I-46)
(I-47)
(I-48)

-continued
(I-49) 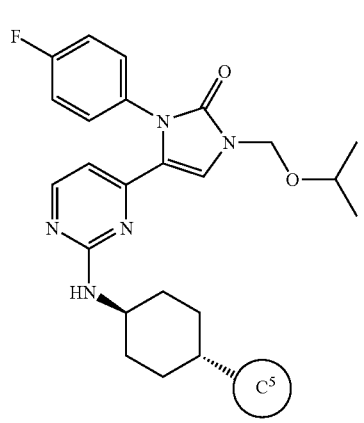
(I-50) 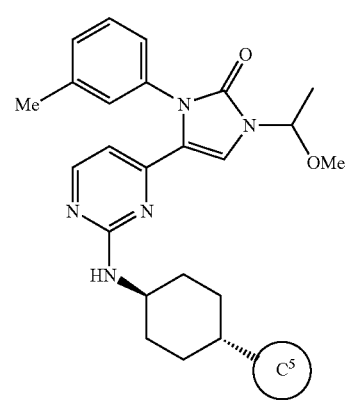
(I-51) 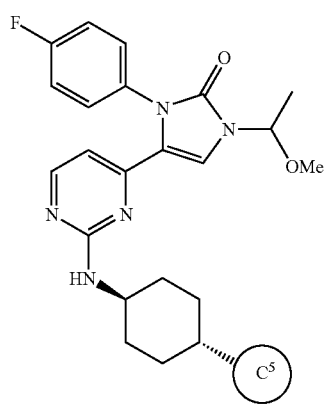
(I-52) 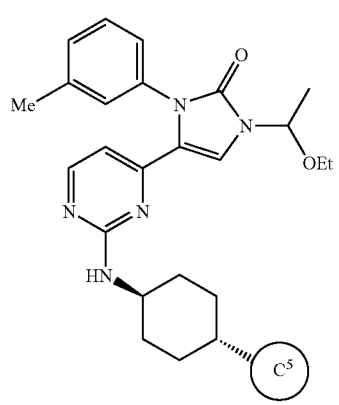
-continued
(I-53) 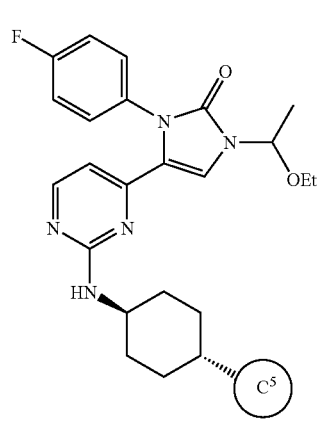
(I-54) 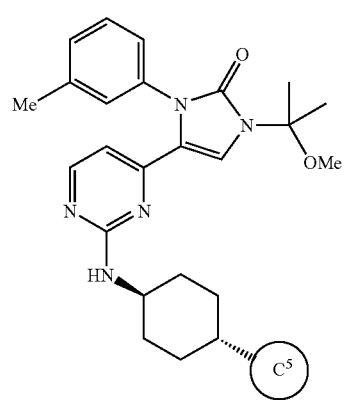
(I-55) 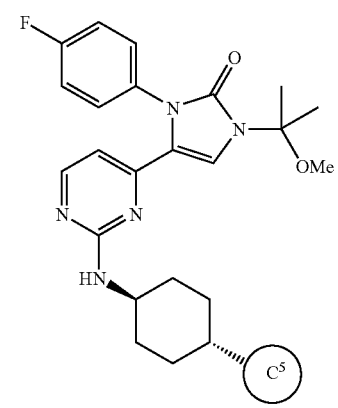
(I-56) 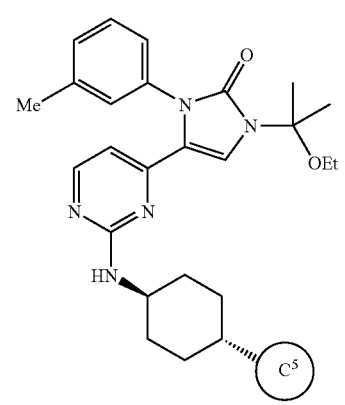

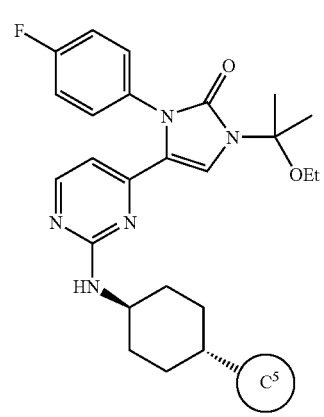
(I-57)
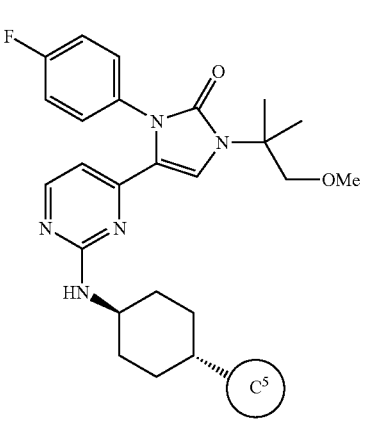
(I-61)
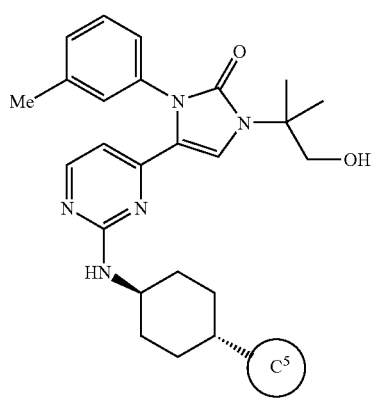
(I-58)
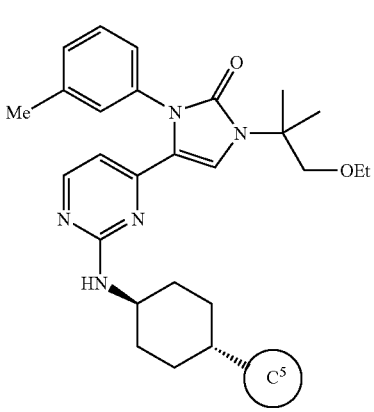
(I-62)
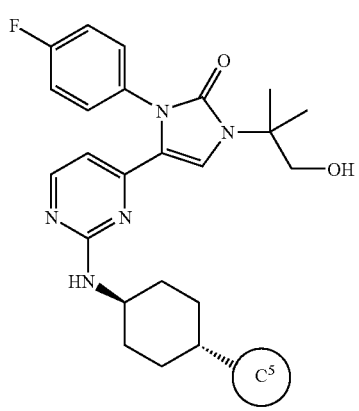
(I-59)
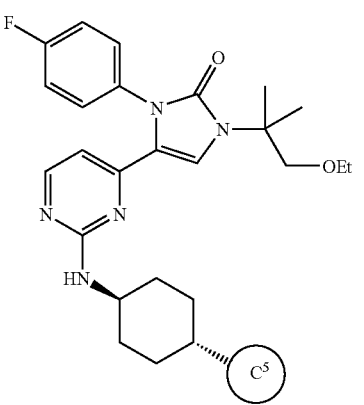
(I-63)
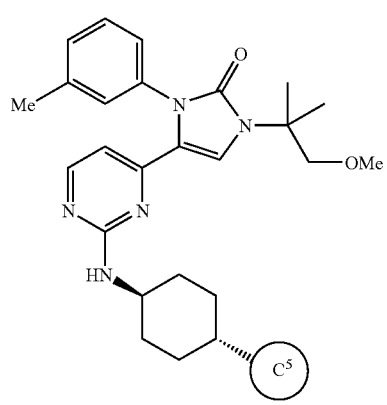
(I-60)
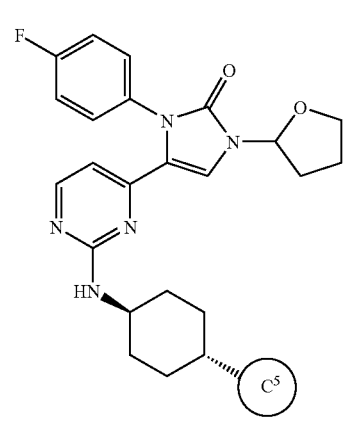
(I-64)

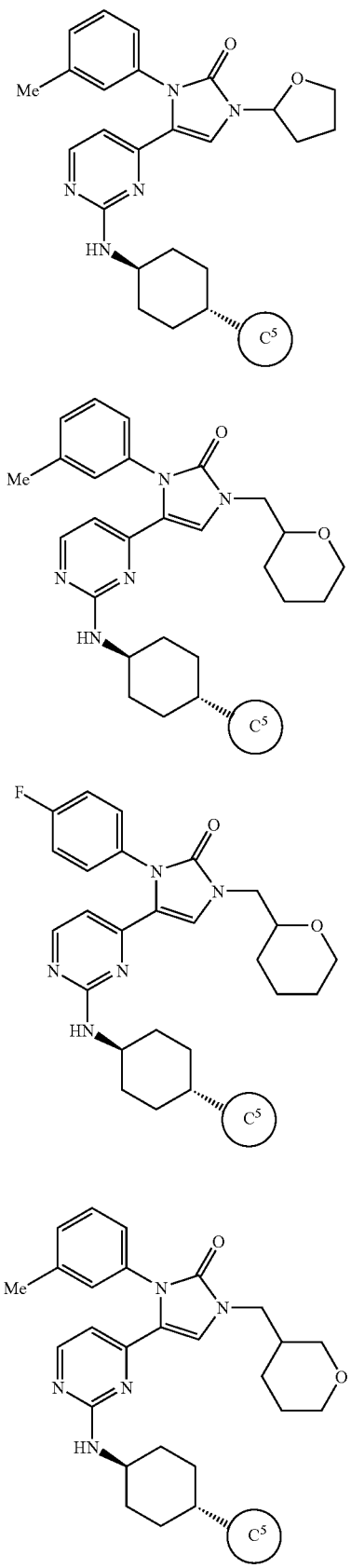
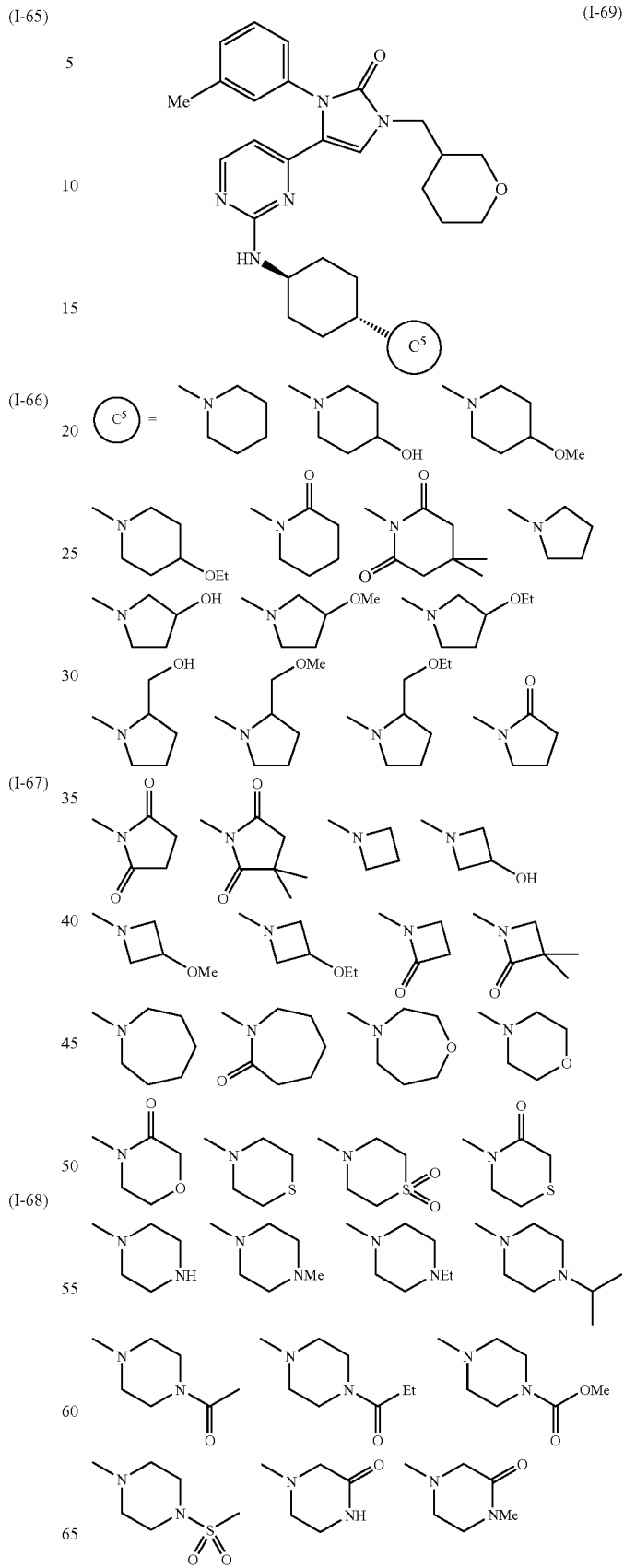

-continued

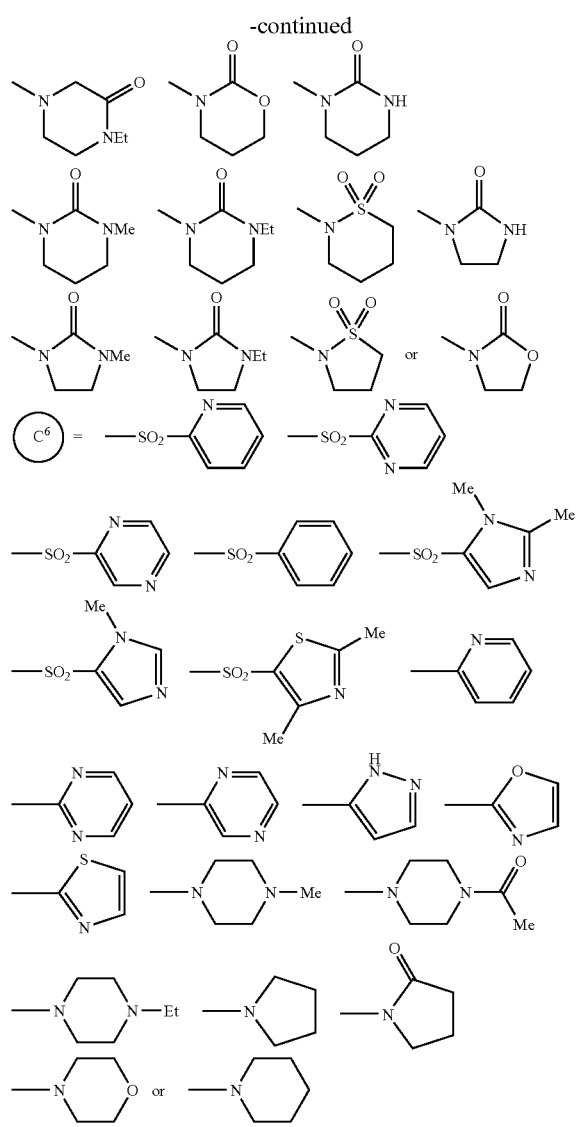

Reference Example 1

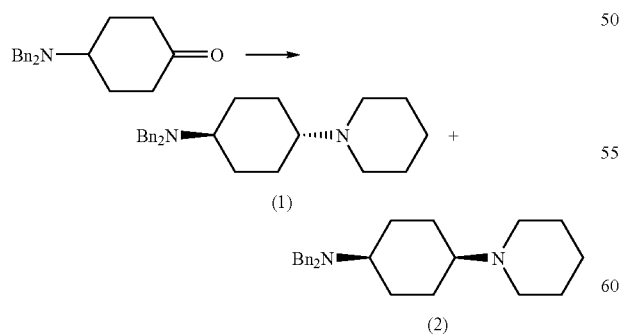

(1) A mixture of 10 g of 4-dibenzylaminocyclohexanone, 3.19 g of piperidine, 2.93 ml of acetic acid and 100 ml of 1,2-dichloroethane was stirred at room temperature for 20 minutes, then, 8.67 g of sodium triacetoxyborohydride was added to the mixture and the resulting mixture was stirred overnight. After saturated aqueous sodium bicarbonate solution was added to the reaction mixture, the resulting mixture was stirred for an hour. The organic layer was separated and dried over anhydrous magnesium sulfate. After concentration under reduced pressure, the residue was purified by NH silica gel column chromatography (hexane:ethyl acetate=10:1) to give 3.10 g of Compound (1) and 6.37 g of Compound (2) as colorless solid.

Compound (1): MS: 363 ([M+H]$^+$)
Compound (2): MS: 363 ([M+H]$^+$)

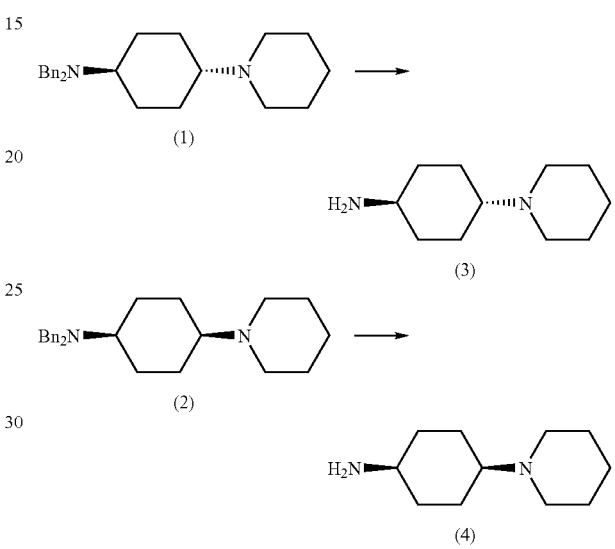

(2) In a mixed solvent of 20 ml of methanol and 10 ml of THF was dissolved 2.92 g of Compound (1), 0.8 g of 10% palladium carbon was added to the solution, and the mixture was stirred at room temperature overnight under hydrogen flow. Insoluble materials were removed by filtration, the filtrate was concentrated under reduced pressure to give 1.30 g of Compound (3) as colorless solid. MS: 183 ([M+H]$^+$)

Compound (2) was reacted and treated in the same manner as mentioned above to give 1.30 g of Compound (4) as pale yellowish oily substance. MS: 183 ([M+H]$^+$)

Reference Example 2

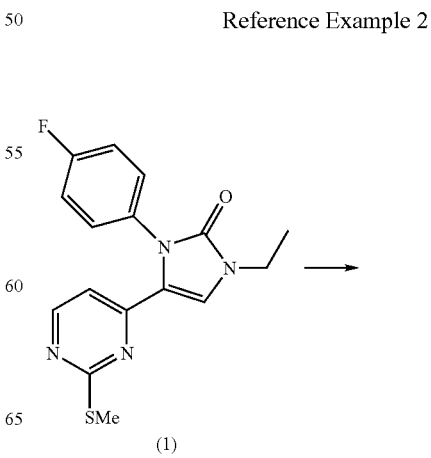

(1)

-continued

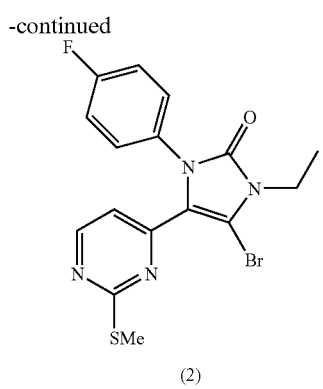

(2)

In 400 ml of chloroform was dissolved 33.0 g of Compound (1) which can be prepared by the same method as described in WO 03/035638, 36.5 g of N-bromosuccinimide was added thereto and the mixture was stirred at room temperature for 7 hours. To the reaction mixture was added 10% aqueous sodium thiosulfate solution, the mixture was extracted with chloroform and the extract was dried over anhydrous magnesium sulfate. After concentration under reduced pressure, the residue was purified by silica gel column chromatography (hexane:ethyl acetate=67:33→62:38) to give 16.7 g of Compound (2) as pale yellowish crystals.

MS: 409, 411 ([M+H]$^+$)

Reference Example 3

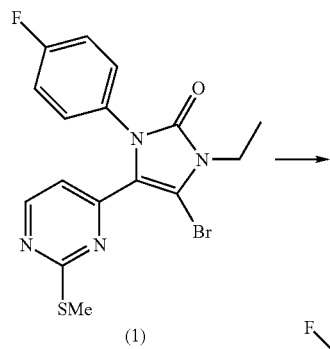

(1)

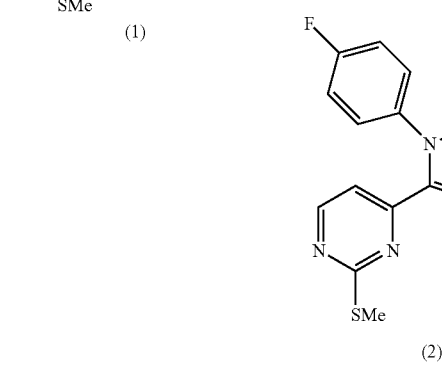

(2)

In 1,4-dioxane were suspended 6.1 g of Compound (1), 1.4 g of methylboronic acid, 613 mg of [1,1'-bis(diphenyl-phosphino)ferrocene]dichloropalladium methylene chloride complex and 9.8 g of cesium carbonate, and the mixture was stirred at 80° C. for 13 hours. After cooling by allowing to stand, water was added to the reaction mixture, the resulting mixture was extracted with ethyl acetate and the extract was dried over anhydrous magnesium sulfate. After concentration under reduced pressure, the residue was purified by silica gel column chromatography (hexane:ethyl acetate=50:50→10:90). After concentration under reduced pressure, the residue was crystallized from isopropyl ether to give 4.5 g of Compound (2) as pale yellowish crystals.

MS: 345 ([M+H]$^+$)

Reference Example 4

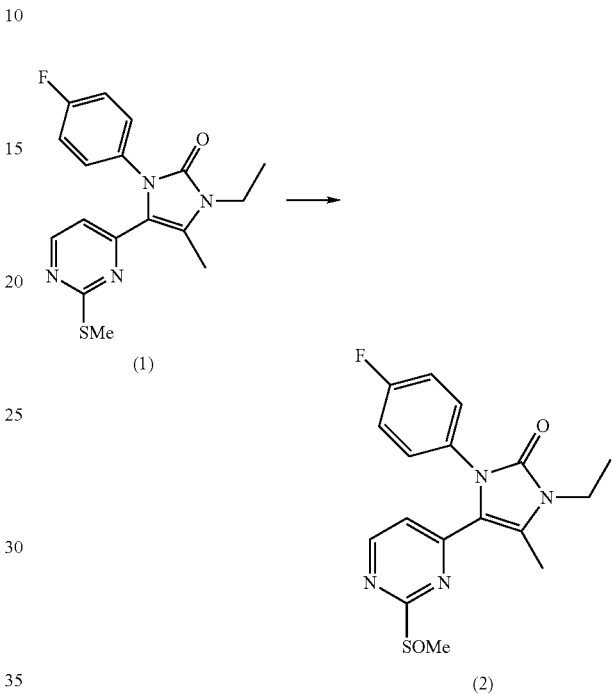

In 40 ml of chloroform was dissolved 3.4 g of Compound (1), 3.9 g of m-chloroperbenzoic acid was dropwise added thereto and the mixture was stirred for 5 minutes under ice-cooling. The mixture was stirred at room temperature for 45 minutes, and to the reaction solution were added 10% aqueous sodium thiosulfate solution and saturated aqueous sodium bicarbonate solution. The mixture was extracted with chloroform and dried over anhydrous magnesium sulfate. After concentration under reduced pressure, the residue was purified by silica gel column chromatography (chloroform:methanol=99:1→94:6) to give 3.0 g of Compound (2) as a pale yellowish powder.

MS: 361 ([M+H]$^+$)

Reference Example 5

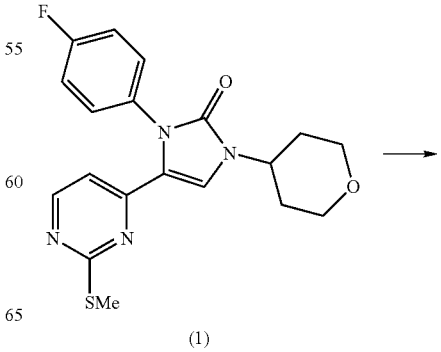

(1)

-continued

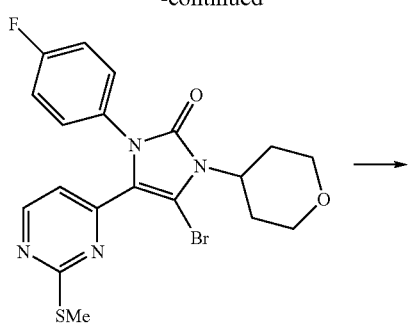

(2)

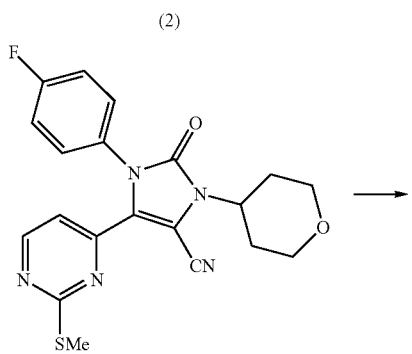

(3)

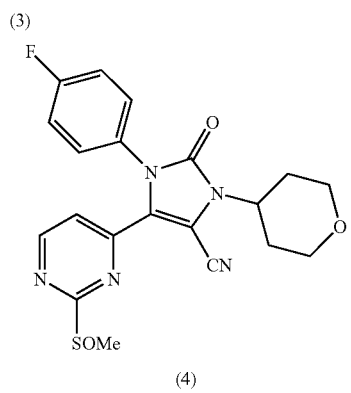

(4)

(1) Compound (1) was reacted and treated in the same manner as in Reference example 2 to give Compound (2) as pale yellowish crystals.

MS: 465, 467 ([M+H]$^+$)

(2) To a solution of 20.94 g of Compound (2) in 180 ml of DMF was added 2.65 g of sodium cyanide at room temperature and the mixture was stirred at 90° C. for 26 hours. After cooling by allowing to stand, saturated aqueous sodium bicarbonate solution was added to the reaction solution. The mixture was extracted with ethyl acetate and dried over anhydrous magnesium sulfate. After concentration under reduced pressure, the obtained crude product was crystallized from ethyl acetate-diethyl ether to give 12.85 g of Compound (3) as pale yellowish crystals.

MS: 412 ([M+H]$^+$)

(3) Compound (3) was reacted and treated in the same manner as in Reference example 4 to give Compound (4) as colorless crystals.

MS: 428 ([M+H]$^+$)

Experimental Example 1

(Pharmacological Test): Inhibitory Effects on Lipo-Polysaccharide (LPS) Induced TNF-α Production in Rat (In Vivo)

This test is a method to assess the inhibitory effects of the compounds of the present invention against TNF-α production induced by LPS in rats.

Rats (LEW/Crj, 6-8 weeks-old, female, available from Charles River Japan, Inc.) were administered with a test compounds (5 mg/kg, p.o.) dissolved by 0.5% methylcellulose, and 0.2% PEG-60 hydrogenated castor oil (HCO60, available from NIKKO CHEMICALS, Co., Ltd.), and after 30 minutes, LPS (*E. coli* 0111:B4, available from SIGMA, the final concentration was adjusted to 0.16 mg/ml by a phosphate buffered physiological saline solution, 6.25 ml/kg, i.p.) was inoculated to rats. After 90 minutes, blood was collected from abdominal vein under diethyl ether anesthesia. The collected blood was centrifuged at 3000 g, and serum was recovered. TNF-α in the serum was measured by ELISA (rat TNF-α ELISA Development Kits, available from genzyme TECHNE).

As a result, as shown in the following table, the following compounds of Examples of the present invention inhibited significantly production of TNF-α.

TABLE 1

| Example | Inhibition on TNF-α production(%) |
|---------|-----------------------------------|
| 10      | 100                               |
| 14      | 97.1                              |

INDUSTRIAL APPLICABILITY

The compound or a pharmaceutically acceptable salt thereof of the present invention has an excellent p38 MAP kinase inhibitory activity, so that an agent for prophylaxis or treatment of diseases to which p38 MAP kinase pertains can be provided.

The invention claimed is:

1. A compound of the formula [I]:

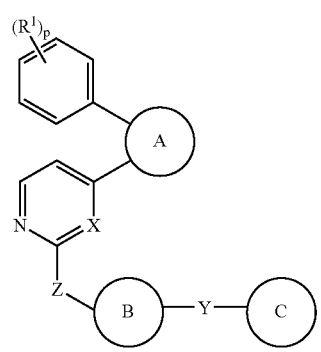

[I]

wherein R$^1$ is
(a) hydrogen,
(b) a halogen,
(c) nitro, (d) an alkyl optionally substituted by 1 to 3 substituent(s) selected from a halogen, hydroxy and amino,
(e) an alkoxy optionally substituted by 1 to 3 substituent(s) selected from hydroxy and amino,
(f) an amino optionally substituted by 1 or 2 substituent(s) selected from (i) an alkyl which may be substituted by 1 to 3 groups independently selected from the group consisting of an alkoxy, amino and carboxy, and (ii) an alkanoyl,
(g) a carbamoyl optionally substituted by alkyl(s),
(h) hydroxy or
(i) cyano,
p is 1 or 2, provided that when p is 2, two R¹s may be the same or different from each other,
Z is —NH—,
Ring A is a ring selected from the following formulae:

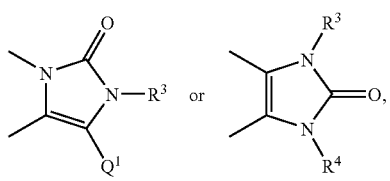

R³ and R⁴ may be the same or different from each other, and each is (CH₂)ₙ—Rᴬ,
Rᴬ is
(a) hydrogen,
(b) an alkyl optionally substituted by 1 to 3 substituent(s) selected from (i) alkynyl, (ii) cyano, (iii) alkoxy, (iv) hydroxy, (v) amino which may be substituted by 1 or 2 substituent(s) independently selected from the group consisting of alkyl, alkanoyl and alkylsulfonyl, (vi) carboxy, (vii) alkoxycarbonyl, (viii) carbamoyl which may be substituted by 1 or 2 alkyl(s), (ix) phenyl and (x) naphthyl,
(c) an alkoxyalkyl,
(d) a cycloalkyl optionally substituted by 1 to 3 substituent(s) selected from (1) hydroxy, (2) alkoxy which may be substituted by 1 to 3 alkoxy(s), (3) amino which may be substituted by the same or different 1 or 2 group(s) independently selected from the groups consisting of (i) alkyl, (ii) alkanoyl, (iii) alkoxycarbonyl, (iv) carbamoyl which may be substituted by 1 or 2 alkyl(s), and (v) alkylsulfonyl, (4) carboxy, (5) alkyl which may be substituted by a group selected from the group consisting of hydroxy, alkoxy and amino, (6) carbamoyl which may be substituted by alkyl(s),
(e) a phenyl optionally substituted by 1 to 3 group(s) selected from (1) a halogen, (2) nitro, (3) alkyl which may be substituted by the same or different 1 to 3 group(s) selected from the group consisting of a halogen, hydroxy, amino, carboxy and phenylsulfonyl, (4) alkenyl, (5) cyano, (6) hydroxy, (7) alkoxy which may be substituted by the same or different 1 to 3 group(s) independently selected from the group consisting of a halogen, carboxy, alkoxycarbonyl, carbamoyl, phenyl and morpholinylcarbonyl, (8) amino which may be substituted by the same or different 1 or 2 group(s) independently selected from the groups of (i) alkyl, (ii) alkanoyl, (iii) carbamoyl which may be substituted by the same or different 1 or 2 group(s) independently selected from the group consisting of alkyl and cycloalkyl, and (iv) alkylsulfonyl, (9) alkanoyl, (10) carboxy, (11) alkoxycarbonyl, (12) carbamoyl which may be substituted by one or two group(s) which may be the same or different from each other independently selected from the groups consisting of (i) alkyl which may be substituted by 1 to 3 hydroxy(s), and (ii) cycloalkyl, (13) alkylthio, (14) alkylsulfinyl, (15) alkylsulfonyl, (16) phenyl, (17) tetrazolyl, (18) heterocyclic group-substituted carbonyl, whose heterocyclic group is selected from the group consisting of furyl, tetrahydrofuryl, tetrahydropyranyl, tetrahydrothiapyranyl, thienyl, tetrahydrothienyl, thiazolyl, isothiazolyl, tetrahydroisothiazolyl, oxazolyl, isoxazolyl, oxadiazolyl, tetrazolyl, pyrrolyl, pyrrolidinyl, pyrrolinyl, imidazolidinyl, imidazolinyl, pyrazolidinyl, pyridyl, pyridazinyl, pyrimidinyl, hexahydropyrimidinyl, pyrazinyl, triazinyl, piperidyl, pyrazolyl, piperazinyl, morpholinyl, dioxanyl, imidazolyl, triazolyl, pyrazolinyl, thiazinyl, and tetrahydrothiazinyl, and the heterocyclic group may be substituted by the same or different 1 to 3 group(s) independently selected from the group consisting of alkyl and alkoxycarbonyl, or
(f) a heterocyclic group selected from the group consisting of furyl, tetrahydrofuryl, tetrahydropyranyl, tetrahydrothiapyranyl, thienyl, tetrahydrothienyl, thiazolyl, isothiazolyl, tetrahydroisothiazolyl, oxazolyl, isoxazolyl, oxadiazolyl, tetrazolyl, pyrrolyl, pyrrolidinyl, pyrrolinyl, imidazolidinyl, imidazolinyl, pyrazolidinyl, pyridyl, pyridazinyl, pyrimidinyl, hexahydropyrimidinyl, pyrazinyl, triazinyl, piperidyl, pyrazolyl, piperazinyl, morpholinyl, dioxanyl, imidazolyl, triazolyl, pyrazolinyl, thiazinyl, and tetrahydrothiazinyl, and which is optionally substituted by 1 to 3 substituent(s) selected from (1) a halogen, (2) nitro, (3) alkyl which may be substituted by a group selected from the group consisting of (i) hydroxy, (ii) alkoxy, (iii) carbamoyl optionally substituted by alkyl, and (iv) carboxy, (4) cyano, (5) hydroxy, (6) amino, (7) alkanoyl, (8) carboxy, (9) alkoxycarbonyl, (10) carbamoyl which may be substituted by 1 or 2 alkyl(s), (11) alkylsulfonyl, (12) phenyl and (13) oxo, n is 0 or an integer of 1 to 4, Q¹ is (a) hydrogen, (b) a halogen, (c) cyano, (d) an alkyl optionally substituted by an amino which may be substituted by an alkyl or an alkanoyl, or (e) a heterocyclic group selected from the group consisting of pyrrolidine, piperidine and homopiperidine, and which is optionally substituted by an alkyl, an alkanoyl, an alkoxycarbonyl or an alkylsulfonyl, Ring B is a cyclohexyl ring, X is N, Y is a single bond, SO₂ or CO, Ring C is a C₆₋₁₄ monocyclic, dicyclic or tricyclic aromatic hydrocarbon ring or a heterocyclic ring selected from the following formulae:

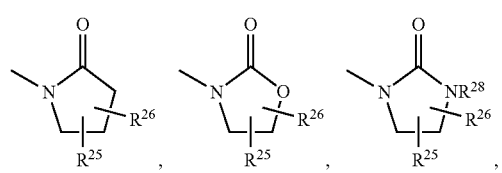

-continued

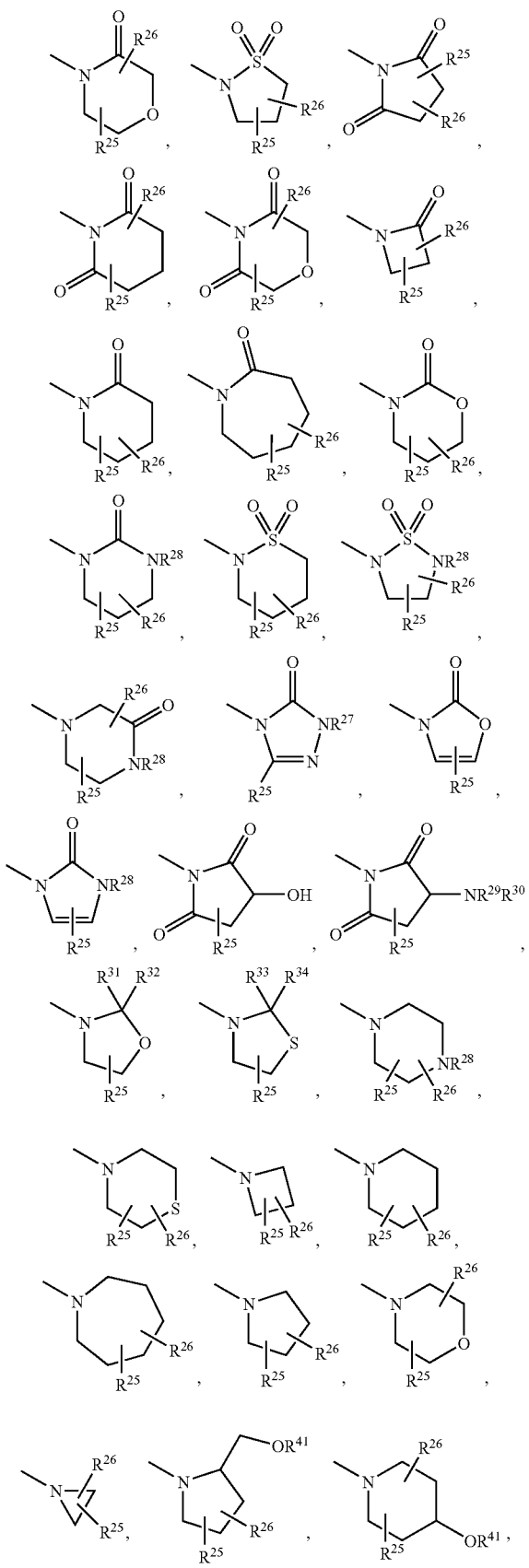

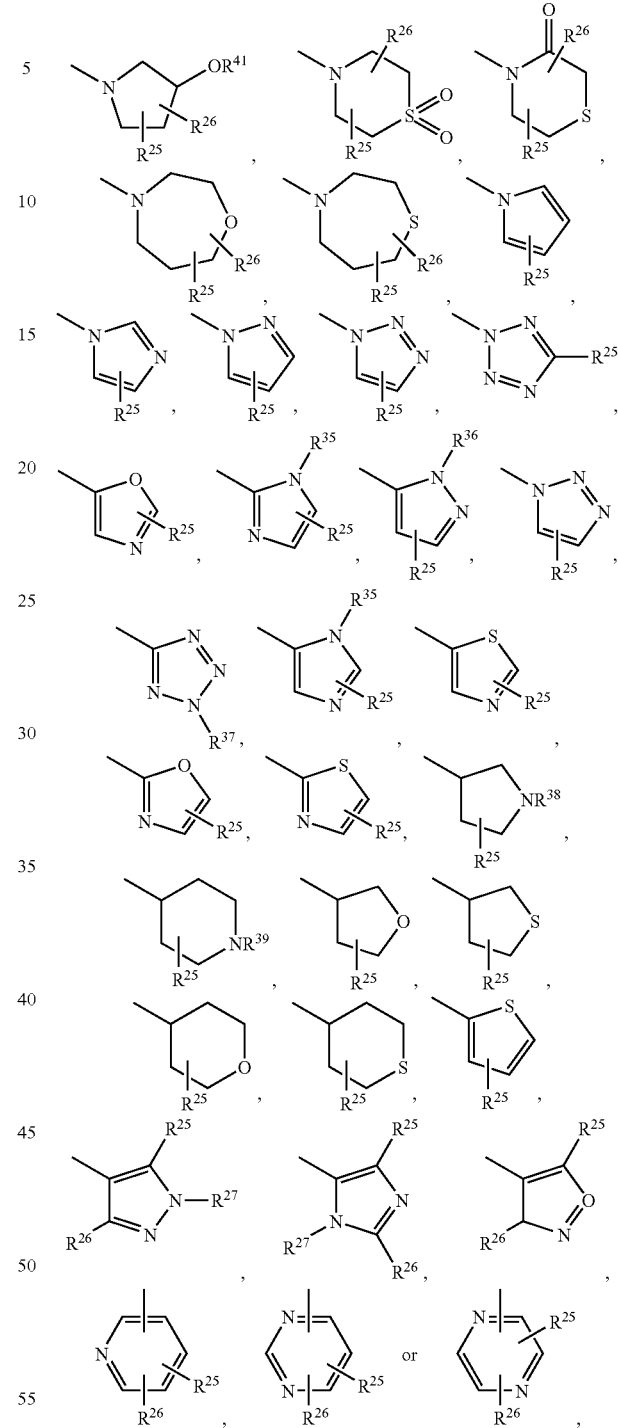

wherein $R^{25}$, $R^{26}$, $R^{31}$ to $R^{37}$ and $R^{41}$ may be the same or different from each other, and each is hydrogen, an alkyl, hydroxy, an alkoxy or an alkoxyalkyl, $R^{27}$ to $R^{30}$, $R^{38}$ and $R^{39}$ may be the same or different from each other, and each is hydrogen, an alkyl or an amino-protective group, or a pharmaceutically acceptable salt thereof.

2. The compound or a pharmaceutically acceptable salt thereof according to claim 1, wherein Ring A is

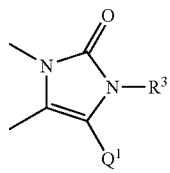

wherein $R^3$ and $Q^1$ have the same meanings as defined in claim 1.

3. The compound or a pharmaceutically acceptable salt thereof according to claim 1, wherein Y is a single bond.

4. The compound or a pharmaceutically acceptable salt thereof according to claim 1, wherein Ring C is the following groups

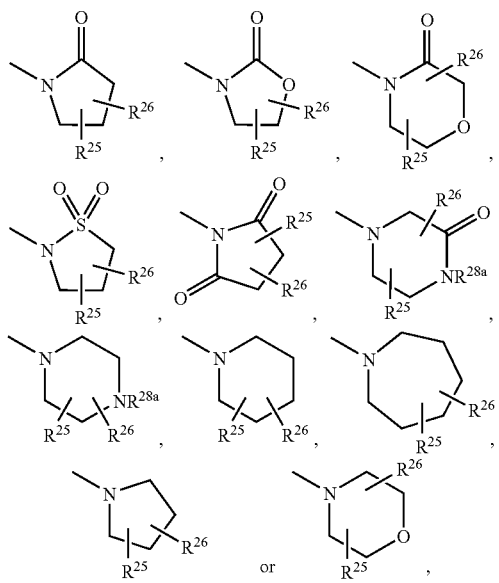

wherein $R^{25}$ and $R^{26}$ may be the same or different from each other, and each is hydrogen, an alkyl, hydroxy, an alkoxy or an alkoxyalkyl, and $R^{28a}$ is hydrogen, an alkyl, an alkanoyl, an alkoxycarbonyl or an alkylsulfonyl.

5. The compound or a pharmaceutically acceptable salt thereof according to claim 1, wherein $R^1$ is a halogen or an optionally substituted alkyl.

6. The compound or a pharmaceutically acceptable salt thereof according to claim 1, wherein $R^1$ is chlorine, fluorine, methyl or trifluoromethyl.

7. The compound or a pharmaceutically acceptable salt thereof according to claim 1, wherein p is 1, and the binding position of $R^1$ is 4-position or 3-position.

8. The compound or a pharmaceutically acceptable salt thereof according to claim 1, wherein p is 1, and the binding position of $R^1$ is 3-position.

9. The compound or a pharmaceutically acceptable salt thereof according to claim 1, wherein $R^A$ is
(a) an alkyl optionally substituted by 1 to 3 substituent(s) selected from (i) alkynyl, (ii) cyano, (iii) alkoxy, (iv) hydroxy, (v) amino which may be substituted by 1 or 2 substituent(s) independently selected from the group consisting of an alkyl, alkanoyl and alkylsulfonyl, (vi) carboxy, (vii) alkoxycarbonyl, (viii) carbamoyl which may be substituted by 1 or 2 alkyl(s), (ix) phenyl and (x) naphthyl,
(b) a monocyclic, dicyclic or tricyclic heterocyclic group containing 1 to 4 hetero atoms independently selected from nitrogen atom, oxygen atom and sulfur atom, and a part or whole portion of which may be saturated, and which is optionally substituted by 1 to 3 substituent(s) selected from (i) halogen, (ii) nitro, (iii) alkyl which may be substituted by a group selected from the group consisting of hydroxy, alkoxy, carbamoyl optionally substituted by alkyl, and carboxy, (iv) cyano, (v) hydroxy, (vi) amino, (vii) alkanoyl, (viii) carboxy, (ix) alkoxycarbonyl, (x) carbamoyl which may be substituted by 1 or 2 alkyl(s), (xi) alkylsulfonyl, (xii) phenyl and (xiii) oxo,
(c) phenyl or
(d) a cycloalkyl,
and n is 0 or 1.

10. The compound or a pharmaceutically acceptable salt thereof according to claim 1, wherein $R^A$ is 4-tetrahydropyranyl and n is 0.

11. A compound of the formula:

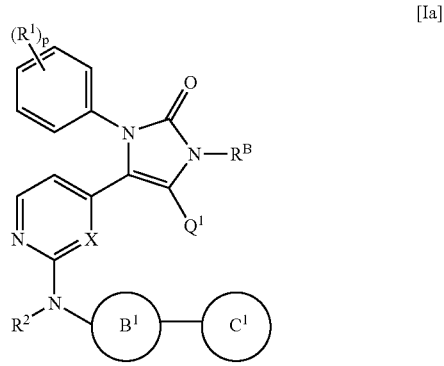

[Ia]

wherein $R^{1a}$ is a halogen or an alkyl optionally substituted by 1 to 3 substituent(s) selected from a halogen, hydroxyl and amino, p is 1 or 2, provided that when p is 2, two $R^{1a}$s may be the same or different from each other, $R^2$ is hydrogen, $R^B$ is (a) an alkyl optionally substituted by 1 to 3 substituent(s) selected from (i) alkynyl, (ii) cyano, (iii) alkoxy, (iv) hydroxy, (v) amino which may be substituted by 1 or 2 substituent(s) independently selected from the group consisting of alkyl, alkanoyl and alkylsulfonyl, (vi) carboxy, (vii) alkoxycarbonyl, (viii) carbamoyl which may be substituted by 1 or 2 alkyl(s), (ix) phenyl and (x) naphthyl, or (b) a heterocyclic group selected from the group consisting of furyl, tetrahydrofuryl, tetrahydropyranyl, tetrahydrothiapyranyl, thienyl, tetrahydrothienyl, thiazolyl, isothiazolyl, tetrahydroisothiazolyl, oxazolyl, isoxazolyl, oxadiazolyl, tetrazolyl, pyrrolyl, pyrrolidinyl, pyrrolinyl, imidazolidinyl, imidazolinyl, pyrazolidinyl, pyridyl, pyridazinyl, pyrimidinyl, hexahydropyrimidinyl, pyrazinyl, triazinyl, piperidyl, pyrazolyl, piperazinyl, morpholinyl, dioxanyl, imidazolyl, triazolyl, pyrazolinyl, thiazinyl, and tetrahydrothiazinyl, which is optionally substituted by 1 to 3 substituent(s) selected from (i) halogen, (ii) nitro, (iii) alkyl which may be substituted by a group selected from the group consisting of hydroxy, alkoxy, carbamoyl optionally substituted by alkyl, and carboxy, (iv) cyano, (v) hydroxy, (vi) amino, (vii) alkanoyl, (viii) carboxy, (ix) alkoxycarbonyl, (x) carbamoyl which may be substituted by 1 or 2 alkyl(s), (xi) alkylsulfonyl, (xii) phenyl and (xiii) oxo, $Q^1$ is (a) hydrogen, (b) a halogen, (c) cyano, (d) an alkyl optionally substituted by an amino which may be substituted by an alkyl or an alkanoyl, or (e) a heterocyclic group selected from the group consisting of pyrrolidine, piperidine and homopiperidine, and which is optionally substituted by an alkyl, an alkanoyl, an alkoxycarbonyl or an alkylsulfonyl, Ring $B^1$ is a cyclohexyl ring, X is N, Ring $C^1$ is a heterocyclic ring selected from the following formulae:

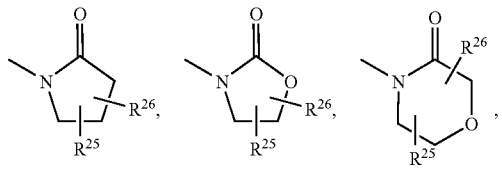

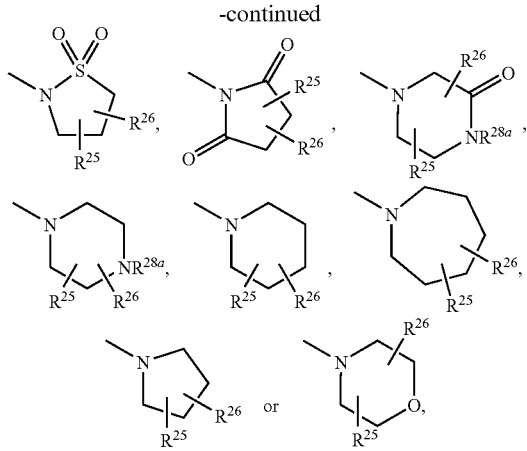

wherein $R^{25}$ and $R^{26}$ may be the same or different from each other, and each is hydrogen, an alkyl, hydroxy, an alkoxy or an alkoxyalkyl, and $R^{28a}$ is hydrogen, an alkyl, an alkanoyl, an alkoxycarbonyl or an alkylsulfonyl, or a pharmaceutically acceptable salt thereof.

* * * * *